United States Patent
Ting et al.

(10) Patent No.: US 12,378,261 B2
(45) Date of Patent: Aug. 5, 2025

(54) ONE-STEP, FAST, 18F-19F ISOTOPIC EXCHANGE RADIOLABELING OF DIFLUORO-DIOXABORININS AND USE OF SUCH COMPOUNDS IN TREATMENT

(71) Applicants: CORNELL UNIVERSITY, Ithaca, NY (US); MEMORIAL SLOAN KETTERING CANCER CENTER, New York, NY (US)

(72) Inventors: Richard Ting, New York, NY (US); Omer Aras, New York, NY (US); Feifei An, New York, NY (US); Nandi Chen, New York, NY (US)

(73) Assignees: Cornell University, Ithaca, NY (US); Memorial Sloan Kettering Cancer Center, New York, NY (US)

( * ) Notice: Subject to any disclaimer, the term of this patent is extended or adjusted under 35 U.S.C. 154(b) by 1074 days.

(21) Appl. No.: 17/057,284

(22) PCT Filed: May 23, 2019

(86) PCT No.: PCT/US2019/033860
§ 371 (c)(1),
(2) Date: Nov. 20, 2020

(87) PCT Pub. No.: WO2019/226962
PCT Pub. Date: Nov. 28, 2019

(65) Prior Publication Data
US 2021/0188880 A1    Jun. 24, 2021

Related U.S. Application Data

(60) Provisional application No. 62/675,519, filed on May 23, 2018.

(30) Foreign Application Priority Data

Apr. 17, 2019   (WO) ................ PCT/US2019/027864

(51) Int. Cl.
*A61K 51/00* (2006.01)
*A61K 9/00* (2006.01)
*A61M 36/14* (2006.01)
*C07F 5/02* (2006.01)

(52) U.S. Cl.
CPC ............ *C07F 5/025* (2013.01); *A61K 9/0019* (2013.01); *C07B 2200/05* (2013.01)

(58) Field of Classification Search
CPC ........ C07F 5/025; C07F 5/022; A61K 9/0019; A61K 45/06; A61K 9/08; A61K 51/0423; C07B 2200/05; C07B 59/00; A61P 35/00
See application file for complete search history.

(56) References Cited

U.S. PATENT DOCUMENTS

| 2013/0189185 A1* | 7/2013 | Li et al. ................ A61K 51/04 424/1.65 |
| 2015/0087937 A1 | 3/2015 | Chongzhao et al. |
| 2017/0089123 A1 | 3/2017 | Canning et al. |

FOREIGN PATENT DOCUMENTS

| WO | WO-2015/034996 | 3/2015 |
| WO | WO-2017/089123 | 6/2017 |
| WO | WO-2018/005732 | 1/2018 |

OTHER PUBLICATIONS

Preston et al. (J. Chem. Soc., Chem. Commun. 1983, 89-90).*
International Search Report and Written Opinion in International Patent Application No. PCT/US2019/033860 dated Jan. 2, 2020 (11 pages).
Laali, et al., "Novel fluorinated curcuminoids and their pyrazole and isoxazole derivatives: Synthesis, structural studies, Computational/Docking and in-vitro bioassay," Journal of Fluorine Chemistry, Feb. 2018, vol. 206, pp. 82-98. https://doi.org/10.1016/j.jfluchem.2017.11.013.
Macedo, et al., "Beta-Diketonate, Beta-Ketoiminate, and Beta-Diiminate Complexes of Difluoroboron," European Journal of Inorganic Chemistry, 2008, Issue 20, pp. 3200-3211 https://doi.org/10.1002/ejic.200800243.
Brown, N. M. D. et al: "Spectroscopy and structure of (1, 3-diketonato)boron difluorides and related compounds", Journals of the Chemical Society. A, Inorganic, Physical and Theoretical Chemistry, Jan. 1, 1969 (Jan. 1, 1969), p. 526.
Costes J P: "Study of redistribution phenomena of fluorine and chlorine monofunctional groups on difunctional, tri and tetracoordinated boron centers", Comptes Rendus Des Seances De L'academie Des Sciences, Serie C: Sciences Chimiques, Jan. 1, 1978 (Jan. 1, 1978), pp. 39-42.

(Continued)

*Primary Examiner* — Michael G. Hartley
*Assistant Examiner* — Melissa J Perreira
(74) *Attorney, Agent, or Firm* — Foley & Lardner LLP

(57) ABSTRACT

A compound according to Formula (I) or a pharmaceutically acceptable salt and/or solvate thereof, wherein $X^1$ and $X^2$ are each independently $^{18}F$ or $^{19}F$; $R^1$ and $R^2$ are each independently alkyl, amine, perfluoroalkyl, alkenyl, alkynyl, aryl, or aralkenyl; and $R^3$ is H, halo, alkyl, alkyl ester, alkenyl, alkynyl, aryl, or aralkenyl; or wherein: $R^1$ and $R^3$ or $R^2$ and $R^3$ join to form a 6-membered cycloalkyl or heterocyclyl; or $R^1$ and $R^3$, $R^2$ and $R^3$, or $R^1$, $R^2$, and $R^3$ join to form a substituted or unsubstituted polycyclic ring, wherein the polycyclic ring comprises fused cycloalkyl, heterocycloalkyl, aryl, or heteroaryl rings.

18 Claims, 42 Drawing Sheets

(56) References Cited

OTHER PUBLICATIONS

Extended European Search Report on EP 19807826.3 DTD Feb. 11, 2022.
Felouat, Abdellah et al: "Synthesis and Photophysical Properties of Difluoroboron Complexes of Curcuminoid Derivatives Bearing Different Terminal Aromatic Units and a meso-Aryl Ring", The Journal of Organic Chemistry, vol. 78, No. 9, May 3, 2013 (May 3, 2013), pp. 4446-4455.
Rao S: "Structure elucidation of the product formed in reaction of curcumin with boron trifluoride etherate", Indian Journal of Chemistry Section B: Organic Chemistry Including Medicinal Chemistry, vol. 27B, No. 10, Jan. 1, 1988 (Jan. 1, 1988), pp. 926-928.
Shapet'ko N N: "N.M.R. of BF2-chelates of .beta.-di- and .beta., .beta.'—tricarbonyl compound", Zhurnal Strukturnoi Khimii, vol. 10, Jan. 1, 1969 (Jan. 1, 1969), pp. 936-938.
Chansaenpak et al., "[18F]-NHC-BF3 adducts as water stable radio-prosthetic groups for PET imaging", Chem. Commun., vol. 51, 2015, pp. 12439-12442, Jan. 1, 2015.
Office Action in EP 19807826.3 Dated Feb. 28, 2023.
Keliher et al., "Efficient Acid-Catalyzed 18F/19F Fluoride Exchange of BODIPY Dyes", ChemMedChem, vol. 9, 2014, pp. 1368-1375, Jul. 1, 2014.

\* cited by examiner

Cur 50 μM

Cur-BF$_2$ 50 μM

Control

ONE-STEP, FAST, 18F-19F ISOTOPIC EXCHANGE RADIOLABELING OF DIFLUORO-DIOXABORININS AND USE OF SUCH COMPOUNDS IN TREATMENT

CROSS-REFERENCE TO RELATED APPLICATIONS

This application is a U.S. National Phase Application under 35 U.S.C. § 371 of International Application No. PCT/US2019/033860, filed May 23, 2019, which claims the benefit of and priority to U.S. Provisional Application No. 62/675,519 filed May 23, 2018, and International Application No. PCT/US2019/027864, filed Apr. 17, 2019, the entire disclosures of each of which are herein incorporated by reference for any and all purposes.

U.S. GOVERNMENT RIGHTS

This invention was made with government support under EB013904 and P30CA008748 awarded by the National Institutes of Health. The government has certain rights in the invention.

FIELD

The present technology relates to difluoro-dioxaborinin compounds and uses of such compounds.

BACKGROUND

In treating diseases such as cancer and others, a means of accurately imaging drug delivery is needed. The current de facto clinical standard is gadolinium-based magnetic resonance imaging (MRI). Contrast surrogate agents, such as gadolinium-diethylenetriamine pentaacetic acid (Gd-DTPA) (Magnavist, Bayer), can be co-infused with a drug to mimic the distribution of therapeutic agents delivered by CED. However, Gd-based contrast agents are not effective therapeutics on their own, and require micromolar quantities to resolve. Gd-DTPA cannot serve as a universal indicator of drug distribution as the diffusive properties of a drug are related to molecular size, mass, hydrogen bonding, and partition coefficient, properties that vary widely between drugs and tracers. Positron emission tomography (PET) can be more sensitive than MR contrast, making PET uniquely useful for tracking chemotherapeutics at nanomolar concentrations. This is clear from recent efforts focused on $^{124}$I-tagged antibodies, which have both a therapeutic effect in tumor-specific antigen targeting, and can be imaged by PET.

PET may be used to immediately diagnose missed drug delivery, which is of paramount importance. Without the ability to image drug delivery, we currently assume that agents are delivered to cancer at adequate doses. This assumption is valid until a clinical indication presents to suggest otherwise (e.g., cancer progression or lack of tumor reduction). This is unacceptable in cancer, as a tumor must progress significantly before drug mis-delivery is realized. PET-guided drug delivery allows for the evaluation of proper drug delivery in real time, so that inadequate intervention can be immediately corrected. Therapeutic, PET labeled imaging agents allow a correlation of therapy with imaging to generate guidelines for proper, missed, or insufficient in vivo drug delivery.

In addition, the NIH has funded the development of advanced [$^{18}$F]-PET and FL imaging equipment. This equipment offers orders-of-magnitude resolution improvements and robotic control over current clinical equipment. Yet, few fluorescent and $^{18}$F-PET tracers are approved for human use. This lack of contrast agents currently limits the use of advanced bioimaging and bioengineering equipment, including the PET/MR scanner and robotic platforms for image-guided surgery.

Accordingly, there is a pressing need for contrast agents suitable for use in bioimaging and bioengineering equipment as described herein.

SUMMARY

In one aspect, the present technology provides a compound according to Formula (I)

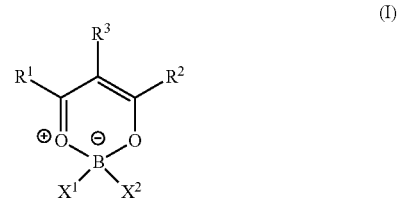

or a pharmaceutically acceptable salt and/or solvate thereof, wherein
  $X^1$ and $X^2$ are each independently $^{18}$F or $^{19}$F;
  $R^1$ and $R^2$ are each independently alkyl, amine, perfluoroalkyl, alkenyl, alkynyl, aryl, or aralkenyl; and
  $R^3$ is H, halo, alkyl, alkyl ester, alkenyl, alkynyl, aryl, or aralkenyl;
  or where:
    $R^1$ and $R^3$ or $R^2$ and $R^3$ join to form a 6-membered cycloalkyl or heterocyclyl; or
    $R^1$ and $R^3$, $R^2$ and $R^3$, or $R^1$, $R^2$, and $R^3$ join to form a substituted or unsubstituted polycyclic ring, wherein the polycyclic ring comprises two or more fused cycloalkyl, heterocycloalkyl, aryl, or heteroaryl rings.

In another aspect, the present technology provides a method that includes administering a compound of Formula (I) as described herein in any embodiment, or a pharmaceutically acceptable salt and/or solvate thereof, to a subject suffering from a cancer. In any embodiment herein, the method includes administering an effective amount of a compound described herein in any embodiment for imaging the cancer.

In a related aspect, the present technology provides a method for inhibiting the proliferation of one or more cancer cells, where the method includes contacting the one or more cancer cells with a compound of Formula (I) as described herein in any embodiment, or a pharmaceutically acceptable salt and/or solvate thereof.

In yet another aspect, the present technology provides a method for treating cancer in a subject, wherein the method includes administering to the subject in need thereof a therapeutically effective amount of a compound of Formula (I) as described herein in any embodiment, or a pharmaceutically acceptable salt and/or solvate thereof.

BRIEF DESCRIPTION OF THE FIGURES

FIG. 1A provides a kinetic analysis of rapid, room temperature (21° C.) $^{18}$F-$^{19}$F difluoro-dioxaborinin isotopic exchange on DK-1. FIG. 1B provides an analysis of isotopic exchange RCY as a function of starting [$^{18}$F]-fluoride ion activity. FIG. 1C provides DK-1 specific activity as a function of DK-1 quantity. FIG. 1D provides HPLC characterization of DK-1 radiosynthetic purity, and proof of isotopic exchange.

FIG. 3C shows the PET/MRI imaging of rabbit sentinel (popliteal) lymph nodes (there are 2 sentinel nodes) using [$^{18}$F]-6F-Cur-BF$_2$. A 200 μCi dose of [$^{18}$F]-6F-Cur-BF$_2$ and Magnevist (MRI contrast agent) were injected into the right rear paw of rabbit. The injection site (bottom arrow) and sentinel lymph node (popliteal, upper arrows) are visible at 5 min. FIGS. 3D-3F show popliteal (sentinel) lymph node imaging 2 hours post injection into the back paw with a Pre-Clinical IVIS. Optical/Computed Tomography In Vivo Imaging System (Excitation filter centered at 430 nm and emission filter centered at 520 nm. Exposure time=1 s). FIG. 3D shows overlaid imaging of fluorescence imaging and bright field image on the mouse. FIG. 3E shows the overlay imaging of fluorescence imaging and bright field image on the mouse with skin removed around the lymph node. FIG. 3F shows over-exposed imaging of FIG. 3E. White arrows in FIGS. 3D-3F indicate the lymph nodes.

DETAILED DESCRIPTION

Figure 1A:
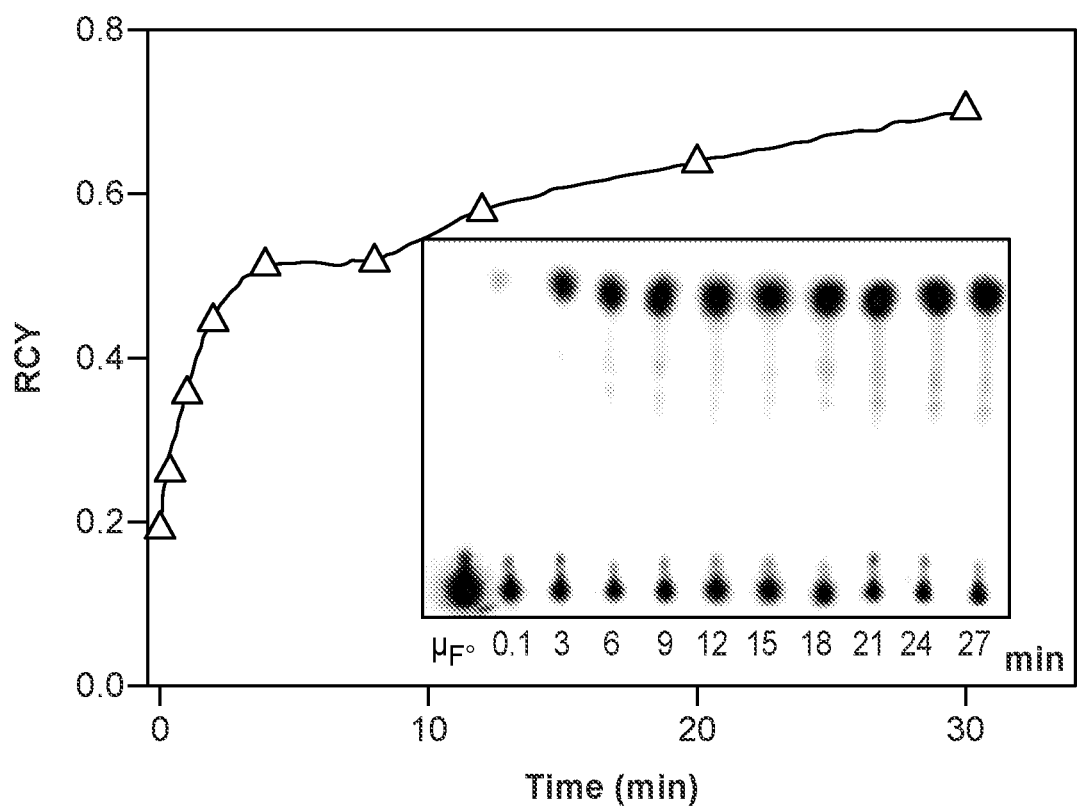
FIGS. 1A-D illustrate the rapid, room temperature radiolabeling of difluoro-dioxaborinin, DK-1, according to the working examples.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

As used herein, $C_m$-$C_n$, such as $C_1$-$C_{12}$, $C_1$-$C_8$, or $C_1$-$C_6$ when used before a group refers to that group containing m to n carbon atoms.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Alkyl groups may be substituted or unsubstituted. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like. Another example of a substituted alkyl group includes perfluoroalkyl, where all hydrogen atoms of the alkyl group are replaced by fluorine.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1] hexane, adamantyl, decalinyl, and the like. Cycloalkyl groups may be substituted or unsubstituted. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 16 carbon atoms, 4 to 12 carbon atoms, and typically 4 to 10 carbon atoms. Cycloalkylalkyl groups may be substituted or unsubstituted. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, among others. Alkenyl groups may be substituted or unsubstituted. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. Cycloalkenyl groups may be substituted or unsubstituted. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl.

Cycloalkenylalkyl groups are alkyl groups as defined above in which a hydrogen or carbon bond of the alkyl group is replaced with a bond to a cycloalkenyl group as defined above. Cycloalkenylalkyl groups may be substituted or unsubstituted. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to —C≡CH, —C≡CCH$_3$, —CH$_2$C≡CCH$_3$, —C≡CCH$_2$CH(CH$_2$CH$_3$)$_2$, among others. Alkynyl groups may be substituted or unsubstituted. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Aryl groups may be substituted or unsubstituted. The phrase "aryl groups" includes groups containing fused rings, such as fused aromatic-aliphatic ring systems (e.g., indanyl, tetrahydronaphthyl, and the like). Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 10 carbon atoms. Aralkyl groups may be substituted or unsubstituted. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3] dioxolyl. The phrase also includes bridged polycyclic ring systems containing a heteroatom such as, but not limited to, quinuclidyl. Heterocyclyl groups may be substituted or unsubstituted. Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Heteroaryl groups may be substituted or unsubstituted. Thus, the phrase "heteroaryl groups" includes fused ring compounds as well as includes heteroaryl groups that have other groups bonded to one of the ring members, such as alkyl groups. Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Heterocyclylalkyl groups may be substituted or unsubstituted. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Heteroaralkyl groups may be substituted or unsubstituted. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene. Such groups may further be substituted or unsubstituted.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Alkoxy groups may be substituted or unsubstituted. Representative substituted alkoxy groups may be substituted one or more times with substituents such as those listed above.

The terms "alkanoyl" and "alkanoyloxy" as used herein can refer, respectively, to —C(O)-alkyl and —O—C(O)-alkyl groups, where in some embodiments the alkanoyl or alkanoyloxy groups each contain 2-5 carbon atoms. Similarly, the terms "aryloyl" and "aryloyloxy" respectively refer to —C(O)-aryl and —O—C(O)-aryl groups.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylic acid" as used herein refers to a compound with a —C(O)OH group. The term "carboxylate" as used herein refers to a —C(O)O— group. A "protected carboxylate" refers to a —C(O)O-G where G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, NY, (3rd Edition, 1999) which can be added or removed using the procedures set forth therein and which is hereby incorporated by reference in its entirety and for any and all purposes as if fully set forth herein.

The term "ester" as used herein refers to —COOR$^{70}$ groups. R$^{70}$ is a substituted or unsubstituted alkyl, cycloalkyl, alkenyl, alkynyl, aryl, aralkyl, heterocyclylalkyl or heterocyclyl group as defined herein.

The term "amide" (or "amido") includes C- and N-amide groups, i.e., —C(O)NR$^{71}$R$^{72}$, and —NR$^{71}$C(O)R$^{72}$ groups, respectively. R$^{71}$ and R$^{72}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H). In some embodiments, the amide is —NR$^{71}$C(O)—(C$_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., —NR$^{73}$C(O)OR$^{74}$ and —OC(O)NR$^{73}$R$^{74}$ groups, respectively. R$^{73}$ and R$^{74}$ are independently a substituted or unsubstituted alkyl, alkenyl, alkynyl, cycloalkyl, aryl, aralkyl, heterocyclylalkyl, or heterocyclyl group as defined herein. R$^{73}$ may also be H.

The term "amine" (or "amino") as used herein refers to —NR$^{75}$R$^{76}$ groups, wherein R$^{75}$ and R$^{76}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH$_2$, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$^{78}$R$^{79}$ and —NR$^{78}$SO$_2$R$^{79}$ groups, respectively. R$^{78}$ and R$^{79}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$). In some embodiments herein, the sulfonamido is —NHSO$_2$-alkyl and is referred to as the "alkylsulfonylamino" group.

The term "thiol" refers to —SH groups, while sulfides include —SR$^{80}$ groups, sulfoxides include —S(O)R$^{81}$ groups, sulfones include —SO$_2$R$^{82}$ groups, and sulfonyls include —SO$_2$OR$^3$. R$^{80}$, R$^{81}$, R$^{82}$, and R$^{83}$ are each independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to —NR$^{84}$—C(O)—NR$^{85}$R$^{86}$ groups. R$^{84}$, R$^{85}$, and R$^{86}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR$^{87}$)NR$^{88}$R$^{89}$ and —NR$^{87}$C(NR$^{88}$)R$^{89}$, wherein R$^{87}$, R$^{88}$, and R$^{89}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NR$^{90}$C(NR$^{91}$)NR$^{92}$R$^{93}$, wherein R$^{90}$, R$^{91}$, R$^{92}$ and R$^{93}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R$^{94}$)=C(R$^{95}$)NR$^{96}$R$^{97}$ and —NR$^{94}$C(R$^{95}$)=C(R$^{96}$)R$^{97}$, wherein R$^{94}$, R$^{95}$, R$^{96}$ and R$^{97}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxyl" as used herein can refer to —OH or its ionized form, —O$^-$.

The term "imide" refers to —C(O)NR$^{98}$C(O)R$^{99}$, wherein R$^{98}$ and R$^{99}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR$^{100}$(NR$^{101}$) and —N(CR$^{100}$R$^{101}$) groups, wherein R$^{100}$ and R$^{101}$ are each independently hydrogen or a substituted or unsubstituted alkyl, cycloalkyl, alkenyl, alkynyl, aryl aralkyl, heterocyclyl or heterocyclylalkyl group as defined herein, with the proviso that R$^{100}$ and R$^{101}$ are not both simultaneously hydrogen.

The term "nitro" as used herein refers to an —NO$_2$ group.

The term "trifluoromethyl" as used herein refers to —CF$_3$.

The term "trifluoromethoxy" as used herein refers to —OCF$_3$.

The term "azido" refers to —N$_3$.

The term "trialkyl ammonium" refers to a —N(alkyl)$_3$ group. A trialkylammonium group is positively charged and thus typically has an associated anion, such as halogen anion.

The term "trifluoromethyldiazirido" refers to

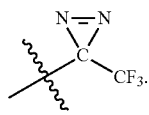

The term "isocyano" refers to —NC.
The term "isothiocyano" refers to —NCS.
The term "pentafluorosulfanyl" refers to —SF$_5$.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid).

When the compound of the present technology has an acidic group, such as for example, a carboxylic acid group, it can form salts with metals, such as alkali and earth alkali metals (e.g., Na$^+$, Li$^+$, K$^+$, Ca$^{2+}$, Mg$^{2+}$, Zn$^{2+}$), ammonia or organic amines (e.g. dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

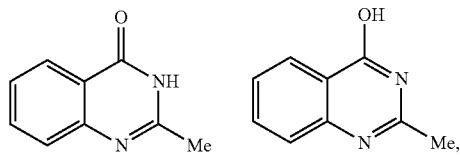 [SMILES: Cc1nc2ccccc2c(=O)[nH]1 ; Cc1nc(O)c2ccccc2n1]

As another example, guanidines may exhibit the following isomeric forms in protic organic solution, also referred to as tautomers of each other:

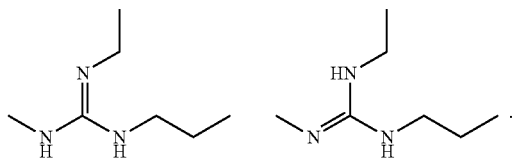

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

As used herein, the term "subject" may include, but is not limited to, a mammal such as a human, a non-human primate, a dog, a cat, a horse, a sheep, a goat, a cow, a rabbit, a pig, a rat and a mouse. In a cancer-afflicted human subject, for example, the subject may be newly diagnosed, or relapsed and/or refractory, or in remission.

As used herein, "treating" or "treatment" of a subject suffering with a disorder (e.g., cancer) may include, but is not limited to, (i) slowing, stopping or reversing the disorder's progression, (ii) slowing, stopping or reversing the progression of the disorder's symptoms, (iii) reducing the likelihood of the disorder's recurrence, and/or (iv) reducing the likelihood that the disorder's symptoms will recur. In a preferred embodiment, treating a subject suffering with a disorder may include (i) reversing the disorder's progression, ideally to the point of eliminating the disorder, and/or (ii) reversing the progression of the disorder's symptoms, ideally to the point of eliminating the symptoms, and/or (iii) reducing or eliminating the likelihood of relapse.

"Pharmaceutically acceptable carriers" are well known to those skilled in the art. For example, injectable drug delivery systems include solutions, suspensions, gels, microspheres and polymeric injectables, and may include excipients such as solubility-altering agents (e.g., ethanol, propylene glycol and sucrose) and polymers (e.g., polycaprylactones and PLGA's). Likewise, oral delivery systems include, for example, tablets and capsules. These may include excipients such as binders (e.g., hydroxypropylmethyl-cellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

As used herein, the term "cancer" may include, but is not limited to, bladder cancer, squamous cell carcinoma including head and neck cancer, pancreatic ductal adenocarcinoma (PDA), pancreatic cancer, breast cancer, fibrosarcoma, mesothelioma, renal cell carcinoma, lung carcinoma, thyoma, prostate cancer, colorectal cancer, ovarian cancer, acute myeloid leukemia, thymus cancer, brain cancer, skin cancer, eye cancer, retinoblastoma, melanoma, intraocular melanoma, oral cavity and oropharyngeal cancers, gastric cancer, cervical cancer, kidney cancer, liver cancer, esophageal cancer, testicular cancer, gynecological cancer, thyroid cancer, acquired immune deficiency syndrome (AIDS)-related cancers (e.g., lymphoma and Kaposi's sarcoma), viral-induced cancer, glioblastoma, glioma, hematological neoplasms, non-small-cell lung cancer, chronic myelocytic leukemia, diffuse large B-cell lymphoma, follicle center lymphoma, hepatitis C virus infection, hepatocellular carcinoma, Hodgkin's disease, metastatic colon cancer, multiple myeloma, non-Hodgkin's lymphoma, indolent non-Hodgkin's lymphoma, small-cell lung cancer, chronic lymphocytic leukemia, B-cell acute lymphoblastic leukemia (ALL), mature B-cell ALL, follicular lymphoma, mantle cell lymphoma, primary central nervous system lymphoma, or Burkitt's lymphoma.

Throughout this disclosure, various publications, patents, and published patent specifications are referenced by an identifying citation. Also within this disclosure are Arabic numerals referring to referenced citations, the full bibliographic details of which are provided after the Examples. The disclosures of these publications, patents, and published patent specifications are hereby incorporated by reference into the present disclosure to more fully describe the present technology.

The Present Technology

The present technology provides a general class of $[^{18/19}F]$-PET/FL agents. The advantages of fusing $^{18/19}F$-PET and FL chemistries include, for example, reduced time and cost in new contrast development. In a two-for-one strategy, the regulatory approval (safety) of a single molecular agent will simultaneously clear both PET and FL imaging modalities for in vivo use. In employing reagents with shared $[^{18/19}F]$-PET/FL molecular structures, resulting methodologies for conjugation, radiochemistry, and post-radiolabeling chromatography will be shared. Translational costs will be reduced, specifically GMP synthesis and toxicological assessment (vs. cost of developing independent, stand-alone PET or FL probes).

A combined PET/FL probe may be advantageous over co-injected mixtures of stand-alone PET or FL contrast agents, in that differences in blood clearance, nonspecific tissue accumulation, ligand affinity, and receptor saturation do not need to be addressed. The agents (i.e., compounds of the present technology) are useful in image-guided surgery. PET and FL are additionally useful together, where: (1) PET allows for pre-surgical planning by distinguishing disseminated (oligometastatic disease) from localized cancer; (2) FL allows for intra-operative surgical guidance, where the extent of a resection is clearly demarcated; and (3) FL allows for margin and node confirmation in triplicate i.e., by the surgeon—in vivo observation of unresected margins in the open surgical site and ex vivo in FL/gamma scintillated analysis of resected tissue, and by the pathologist—ex vivo in FL frozen section intraoperative consult. The present technology improves the efficacy of cancer management by providing persisting, cancer-specific contrast that is useful to multiple specialists on tumor boards (radiologists, urologists, and pathologists) and allows additional FL histology, and FL-assisted cell sorting of resolved cells following surgery.

In a cell-imaging embodiment, fluorescence allows post-surgical fluorescence activated cell sorted (FACS) isolation of cells with characteristics that are selected due to assistance from the subject agents.

Accordingly, the compounds and uses thereof of the present technology provide a number of advantages, which are described herein in greater detail and may include, without limitation: having a low molecular weight, and may cross the blood brain barrier; possessing tailorable optical properties spanning from ultraviolent to orange wavelength, to near-infrared; having a very high specific activity (>1 Ci/μmol) with a relatively low starting dose (<20 mCi); rapid radiolabeling, which may be completed within 10 min and proceeds at room temperature; $[^{18}F]$-labeled compounds as described herein may be used for clinical sentinel lymph node imaging; dynamic PET imaging may be used to determine sentinel node status; and the compounds may be employed for lymph node imaging, pre-targeting, cancer imaging, fluorescence guided surgery, brain imaging, hemorrhage imaging, cellular imaging, PET/MR imaging, PET/CT imaging, and PET/fluorescence imaging.

In view of the above, the present technology provides agents that are $BF_2$-modified β-diketone-containing small molecules. [The SMILES (Simplified Molecular-Input Line-Entry System) code for this moiety where R is variable is O=C([R])/C=C([R])\O.] β-diketone-containing small molecules may include, but are not limited to, anticancer drugs (e.g., doxorubicin and daunorubicin), antibiotics (e.g., tetracycline and glycylcycline), or natural products (e.g., emodin and curcumin). Specifically, these $BF_2$-modified agents (i.e., difluoro-dioxaborinins) include β-diketone-containing small molecules wherein the β-diketone moiety is conjugated to $BF_2$ so that the boron atom is bound to each keto oxygen atom and to each fluorine atom.

Compounds and Compositions of the Present Technology (Also Referred to Herein as "$[^{18/19}F]$—$BF_2$ Agents")

In one aspect, the present technology provides a compound according to Formula (I)

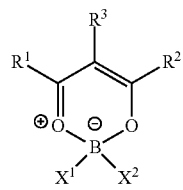

(I)

or a pharmaceutically acceptable salt and/or solvate thereof, wherein $X^1$ and $X^2$ are each independently $^{18}F$ or $^{19}F$;

$R^1$ and $R^2$ are each independently alkyl, amine, perfluoroalkyl, alkenyl, alkynyl, aryl, or aralkenyl; and $R^3$ is H, halo, alkyl, alkyl ester, alkenyl, alkynyl, aryl, or aralkenyl;

or where:

$R^1$ and $R^3$ or $R^2$ and $R^3$ join to form a 6-membered cycloalkyl or heterocyclyl; or $R^1$ and $R^3$, $R^2$ and $R^3$, or $R^1$, $R^2$, and $R^3$ join to form a substituted or unsubstituted polycyclic ring, wherein the polycyclic ring comprises fused cycloalkyl, heterocycloalkyl, aryl, or heteroaryl rings.

In any embodiment herein, $X^1$ and $X^2$ may be $^{18}F$. In any embodiment herein, $X^1$ may be $^{18}F$ and $X^2$ may be $^{18}F$ or $^{19}F$. In any embodiment herein, $X^1$ may be $^{18}F$ and $X^2$ may be $^{19}F$. In any embodiment herein, $X^1$ and $X^2$ may be $^{19}F$. In any embodiment herein, $X^1$ may be $^{18}F$ or $^{19}F$ and $X^2$ may be $^{18}F$. In any embodiment herein, $X^1$ may be $^{18}F$ or $^{19}F$ and $X^2$ may be $^{19}F$. In any embodiment herein, $R^1$ and $R^2$ may each independently be an alkyl, an alkenyl, an aryl, or a —CH=CH-aryl. For example, in any embodiment herein, $R^1$ and $R^2$ may each independently be a —CH=CH-aryl.

In any embodiment herein, the aryl of the —CH=CH-aryl may be a substituted or unsubstituted phenyl. For example, in any embodiment herein, the aryl may be an unsubstituted phenyl. In any embodiment herein, the aryl may be a substituted phenyl. For example, in any embodiment herein, the phenyl may be represented by Formula (II):

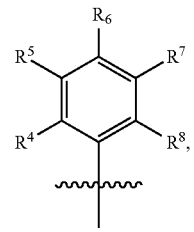

(II)

where each of $R^4$, $R^5$, $R^6$, $R^7$, and $R^8$ may each independently be an H, halo, hydroxyl, $C_1$-$C_6$ alkyl, $C_1$-$C_6$ alkoxy, or —O(O)CR$^9$, where $R^9$ may be substituted or unsubstituted $C_1$-$C_3$ alkyl or aryl, or $R^9$ may be represented by a structure of Formula (III):

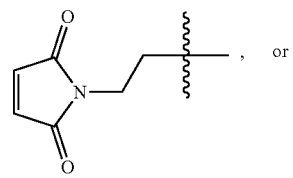

(III)

Formula (IV)

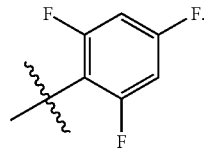

(IV)

In any embodiment herein, $R^4$, $R^7$, and $R^8$ may each independently be H. In any embodiment herein, $R^5$ and $R^6$ may each independently be a hydroxyl or a $C_1$-$C_6$ alkoxy. For example, in any embodiment herein, $R^5$ may be a $C_1$-$C_6$ alkoxy. In any embodiment herein, $R^5$ may be a $C_1$-$C_3$ alkoxy. For example, $R^5$ may be methoxy, ethoxy, n-propoxy, or isopropoxy. In any embodiment herein, $R^5$ may be methoxy. In any embodiment herein, $R^6$ may be hydroxyl. In any embodiment herein, $R^5$ may be a $C_1$-$C_6$ alkoxy, $R^6$ may be hydroxyl, and $R^4$, $R^7$, and $R^8$ may each independently be H. In any embodiment herein, $R^6$ may be a —C(O)OR$^9$. In any embodiment herein, $R^9$ may be a structure of Formula (III). In any embodiment herein, $R^9$ may be a structure of Formula (IV).

In any embodiment herein, $R^3$ may be H, alkyl, or alkyl ester. In any embodiment herein, $R^3$ may be H. In any embodiment herein, $R^3$ may be a $C_1$-$C_6$ alkyl. For example, in any embodiment herein, $R^3$ may be methyl, ethyl, n-propyl, n-butyl, n-pentyl, n-hexyl, isopropyl, iso-butyl, sec-butyl, tert-butyl, neopentyl, isopentyl, or 2,2-dimethylpropyl. In any embodiment herein, $R^3$ may be methyl or ethyl. In any embodiment herein, $R^3$ may be alkyl ester. For example, in any embodiment herein, $R^3$ may be —R$^{10}$C(O)OR$^{11}$, where $R^{10}$ and $R^{11}$ may each independently be $C_1$-$C_6$ alkyl. In any embodiment herein, $R^3$ may be —CH$_2$CH$_2$C(O)OCH$_2$CH$_3$.

For example, in any embodiment, the compound of Formula (I), or a pharmaceutically acceptable salt and/or solvate thereof may be Curcumin-$BF_2$. In any embodiment herein, in the Curcumin-$BF_2$ molecule, each fluorine atom may each independently be $^{18}F$ or $^{19}F$, so that each Curcumin-$BF_2$ molecule may include two $^{18}F$ atoms, two $^{19}F$ atoms, or one $^{18}F$ atom and one $^{19}F$ atom.

In any embodiment herein, $R^1$ and $R^3$ may join form a 6-membered cycloalkyl or heterocyclyl. In any embodiment herein, $R^2$ and $R^3$ may join to form a 6-membered cycloalkyl or heterocyclyl. For example, in any embodiment herein, $R^1$ and $R^3$ may join to form a 6-membered cycloalkyl and $R^2$ may be a $C_1$-$C_6$ alkyl. In any embodiment herein, $R^1$ and $R^3$ may join to form a 6-membered cycloalkyl and $R^2$ may be a $C_1$-$C_3$ alkyl (e.g., methyl, ethyl, or propyl). For example, in any embodiment herein, $R^1$ and $R^3$ may join to form a 6-membered cycloalkyl and $R^2$ may be a methyl.

In any embodiment herein, $R^1$ and $R^3$ may join to form a substituted or unsubstituted polycyclic ring, where the polycyclic ring may include fused cycloalkyl rings, aryl rings, or combinations thereof. In any embodiment herein, $R^2$ and $R^3$ may join to form a substituted or unsubstituted polycyclic ring, where the polycyclic ring may include fused cycloalkyl rings, aryl rings, or combinations thereof. In any embodiment herein, $R^1$ may be an amine. In any embodiment herein, $R^2$ may be an amine. In any embodiment herein, $R^1$ and $R^3$ may join to form a substituted or unsubstituted polycyclic ring that may include fused cycloalkyl and aryl rings, and $R^2$ may be an amine. In any embodiment herein, $R^2$ and $R^3$ may join to form a substituted and unsubstituted polycyclic ring that may include fused cycloalkyl and aryl rings, and $R^1$ may be an amine.

For example, in any embodiment herein, the compound of Formula (I), or a pharmaceutically acceptable salt and/or solvate thereof, may be tetraglycerine-$BF_2$ or glycylcycline-$BF_2$. In any embodiment herein, in the tetraglycerine-$BF_2$ or glycylcycline-$BF_2$ molecule, each fluorine atom is independently $^{18}F$ or $^{19}F$, so that each tetraglycerine-$BF_2$ or glycylcycline-$BF_2$ molecule contains two $^{18}F$ atoms, two $^{19}F$ atoms, or one $^{18}F$ atom and one $^{19}F$ atom.

In any embodiment herein, $R^1$, $R^2$, and $R^3$ may join to form a substituted or unsubstituted polycyclic ring, where the polycyclic ring may include fused cycloalkyl rings, aryl rings, or combinations thereof. For example, in any embodiment herein, the compound of Formula (I), or a pharmaceutically acceptable salt and/or solvate thereof, may be emodin-$BF_2$, doxorubicin-$BF_2$, or daunorubicin-$BF_2$. In any embodiment herein, in the emodin-$BF_2$, doxorubicin-$BF_2$, or daunorubicin-$BF_2$ molecule, each fluorine atom may each independently be $^{18}F$ or $^{19}F$, so that each emodin-$BF_2$, doxorubicin-$BF_2$, or daunorubicin-$BF_2$ molecule may include two $^{18}F$ atoms, two $^{19}F$ atoms, or one $^{18}F$ atom and one $^{19}F$ atom.

Figure 12:
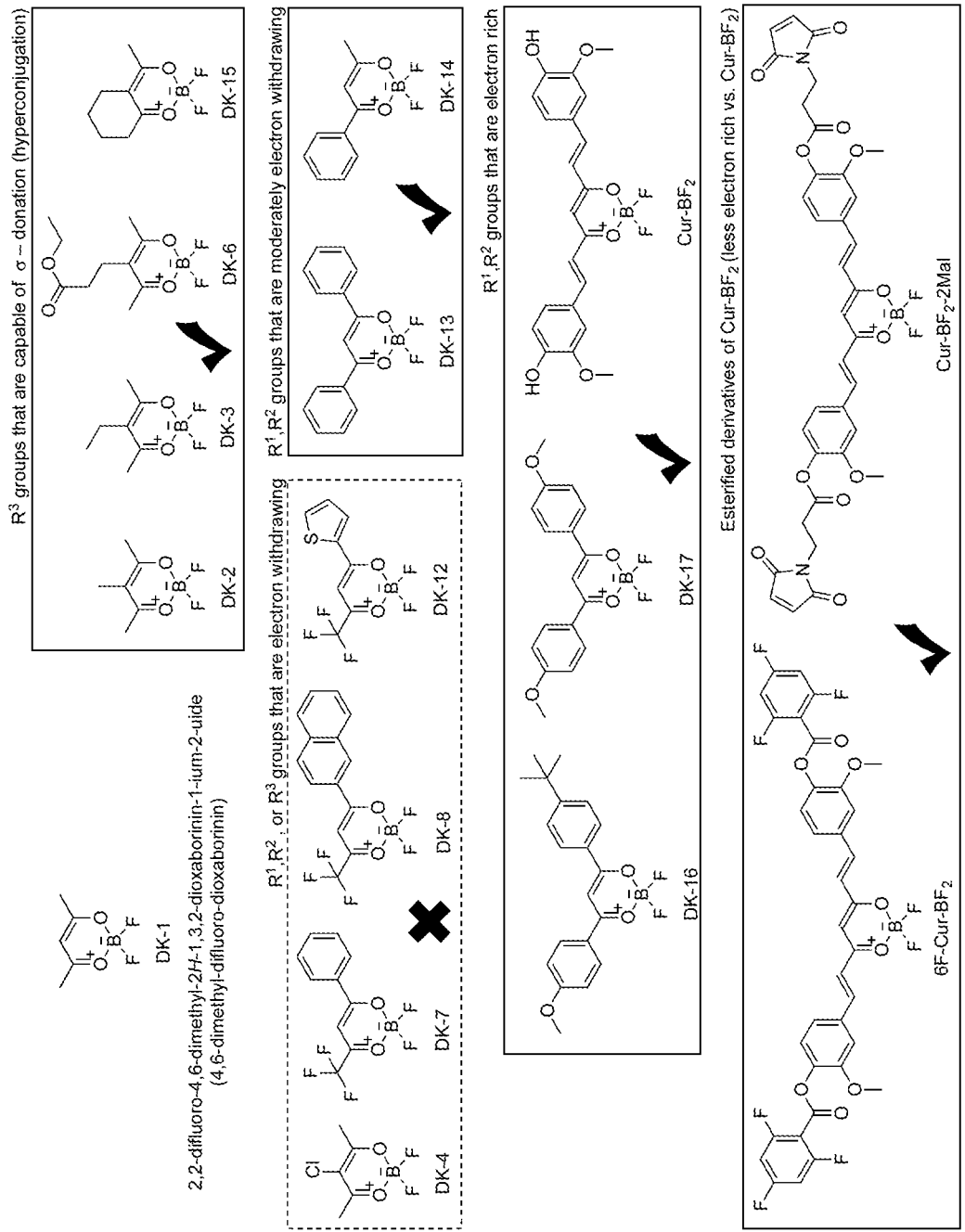
FIG. 12 is a schematic illustration showing structures for difluoro-dioxaborinins (DK-1, DK-2, DK-3, DK-4, DK-6, DK-7, DK-8, DK-12, DK-13, DK-14, DK-15, DK-16, DK-17, Cur-BF$_2$, 6F-Cur-BF$_2$, and Cur-BF$_2$-2Mal).

In any embodiment herein, the compound of Formula (I), or pharmaceutically acceptable salt and/or solvate thereof, may be selected from DK-1, DK-2, DK-3, DK-4, DK-6, DK-7, DK-8, DK-12, DK-13, DK-14, DK-15, DK-16, DK-17, Cur-$BF_2$, 6F-Cur-$BF_2$, or Cur-$BF_2$-2Mal as shown in FIG. 12.

The compound of Formula (I) as described herein in any embodiment, or a pharmaceutically acceptable salt and/or solvate thereof, may exhibit excellent stability upon administration to a subject. In any embodiment herein, the compound of Formula (I) as described herein in any embodiment, or a pharmaceutically acceptable salt and/or solvate thereof, may exhibit no or substantially no detectable degradation during the first 24 hours after administration to a subject in need thereof. As defined herein, "substantially no" detectable degradation refers to the compound of Formula (I), or a pharmaceutically acceptable salt and/or solvate thereof, exhibiting no greater than about 50% of detectable degradation during the first 24 hours after administration to a subject in need thereof. For example, in any embodiment herein, the compound of Formula (I), or a pharmaceutically acceptable salt and/or solvate thereof, may exhibit no greater than about 50%, about 45%, about 40%, about 35%, about 30%, about 25%, about 20%, about 15%, about 10%, about 9%, about 8%, about 7%, about 6%, about 5%, about 4%, about 3%, about 2% about 1%, about 0.5%, about 0.1%, about 0.01%, or any range including and/or in between any two of the preceding, of detectable degradation during the first 24 hours after administration to a subject in need thereof.

In an aspect, the present technology provides a pharmaceutical composition that includes a compound of Formula (I) as described herein in any embodiment, or a pharmaceutically acceptable salt and/or solvate thereof, and one or more pharmaceutically acceptable carriers. In any embodiment herein, the compound of Formula (I), or a pharmaceutically acceptable salt and/or solvate thereof, may be selected from Curcumin-$BF_2$, emodin-$BF_2$, doxorubicin-$BF_2$, daunorubicin-$BF_2$, glycylcycline-$BF_2$, tetracycline-$BF_2$, or a combination of any two or more thereof. In any embodiment herein, the compound of Formula (I), or a pharmaceutically acceptable salt and/or solvate thereof, may be Curcumin-$BF_2$. In any embodiment herein, the compound of Formula (I), or a pharmaceutically acceptable salt and/or solvate thereof, may be doxorubicin-$BF_2$.

The agents, i.e., the compound of Formula (I) as described herein in any embodiment or a pharmaceutically acceptable salt and/or solvate thereof, permit visualizing the delivery and localization of said agent in a subject's body. For example, in any embodiment herein, a pharmaceutical composition that includes a β-diketone-containing compound (i.e., a compound of Formula (I), such as doxorubicin-$BF_2$, daunorubicin-$BF_2$, Curcumin-$BF_2$, etc.) may be used to visualize the delivery and localization of the β-diketone-containing compound in a subject's body. In any embodiment herein, the pharmaceutical composition may include a therapeutically effective amount of a compound of Formula (I) as described herein in any embodiment, or a pharmaceutically acceptable salt and/or solvate thereof. In any embodiment herein, the pharmaceutical composition may include an imaging effective amount of a compound of Formula (I) as described herein in any embodiment, or a pharmaceutically acceptable salt and/or solvate thereof.

In any embodiment herein, the pharmaceutical composition may further include a non-$BF_2$ modified counterpart to the compound of Formula (I), or a pharmaceutically acceptable salt and/or solvate thereof. Such non-$BF_2$ modified counterparts may be represented by a structure of Formula (V):

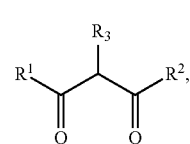 (V)

or a pharmaceutically acceptable salt and/or solvate thereof, wherein $R^1$, $R^2$, and $R^3$ are as defined herein in any embodiment.

To illustrate by way of example and without limitation, the pharmaceutical composition as described herein may include a β-diketone-containing anticancer drug (e.g., doxorubicin-$BF_2$) by itself or admixed with the non-$BF_2$ modified counterpart of the anticancer drug (e.g., doxorubicin). For example, the doxorubicin-BF$_2$ may be admixed with doxorubicin when administered to a subject to form the pharmaceutical composition.

Methods of the Present Technology

In a related aspect, the present technology provides a method comprising administering a compound of Formula (I) as described herein in any embodiment, or a pharmaceutically acceptable salt and/or solvate thereof, to a subject suffering from a cancer. In any embodiment, the method may include administering a pharmaceutical composition as described herein in any embodiment.

As used herein, the term "administer" or "administering", with respect to an agent (i.e., a compound of Formula (I), or a pharmaceutically acceptable salt and/or solvate thereof, or a pharmaceutical composition as described herein in any embodiment) refers to delivering the agent to a subject's body via any known method. Specific methods of administration include, but are not limited to, intravenous, oral, intramuscular, subcutaneous, and intra-tumoral administration. For example, in any embodiment herein, the administering may include intravenous administration. In any embodiment herein, the subject may be a human.

For example, in any embodiment herein, the method may include administering an effective amount of the compound of Formula (I) as described herein in any embodiment, or a pharmaceutically acceptable salt and/or solvate thereof, for imaging the cancer. In any embodiment, the method may include administering a pharmaceutical composition as described herein in any embodiment, for imaging cancer.

In any embodiment herein, the method may include visualizing any cancer tissue regardless of location in the body of the subject. Suitable tissues include, but are not limited to, breast cancer tissue, lymphatic tumor tissue, brain tumor tissue, lung tumor tissue, or colon tumor tissue.

In any embodiment herein, the method further includes, subsequent to the administering, detecting one or more of positron emission, gamma rays from positron emission and annihilation, and Cerenkov radiation due to positron emission. Such imaging, as described herein in any embodiment of the present technology includes, but is not limited to, PET imaging, fluorescence imaging, or fluorescence-based "optical" imaging (e.g., imaging with the naked eye).

The methods may further include administering the effective amount of the compound of Formula (I) as described herein in any embodiment, or a pharmaceutically acceptable salt and/or solvate thereof, for imaging the cancer in conjunction with one or more additional cancer treatment processes or procedures. Suitable cancer treatment processes or procedures may include, but are not limited to, tissue biopsy, surgical procedures, pathology analysis, histology analysis, tumor status determinations, monitoring progress of cancer therapy, monitoring the progress of cancer surgery, or any combination of two or more thereof.

For example, the methods for imaging cancer as described herein in any embodiment may include one or more of the following:
  (i) performing an agent-targeted (i.e., targeted with a compound of Formula (I), or a pharmaceutically acceptable salt and/or solvate thereof) tissue biopsy (optionally ultrasound-guided) via PET imaging, fluorescence imaging, and/or optical imaging according to the methods described herein in any embodiment;
  (ii) performing a surgical procedure (optionally ultrasound-guided) on a tumor (e.g., removing a tumor, such as a breast tumor, a lymphatic tumor, a brain tumor, a lung tumor, or a colon tumor) while employing PET imaging, fluorescence imaging, and/or optical imaging according to the methods described herein in any embodiment;
  (iii) performing a pathology and/or histology analysis (which analysis may include, for example, a tumor margin analysis) of a tissue sample (e.g., a tumor sample, such as a breast tumor sample, a lymphatic tumor sample, a brain tumor sample, a lung tumor sample, or a colon tumor sample) via PET imaging, fluorescence imaging, and/or optical imaging according to the methods described herein in any embodiment; (iv) determining the status (e.g., size, location, and/or stage) of a tumor (e.g., a tumor, such as a breast tumor, a lymphatic tumor, a brain tumor, a lung tumor, or a colon tumor) via PET imaging, fluorescence imaging, and/or optical imaging according to the methods described herein in any embodiment;
  (v) monitoring the progress of cancer therapy (e.g., the pharmaceutical treatment of a tumor-afflicted subject, such as a subject afflicted with a breast tumor, a lymphatic tumor, a brain tumor, a lung tumor, or a colon tumor) via PET imaging, fluorescence imaging, and/or optical imaging according to the methods described herein in any embodiment; and/or
  (vi) monitoring the progress of cancer surgery (e.g., the surgical removal of a tumor, such as a breast tumor, a lymphatic tumor, a brain tumor, a lung tumor, or a colon tumor) via PET imaging, fluorescence imaging, and/or optical imaging (including pre-op monitoring, post-op monitoring, and monitoring during surgery).

In any embodiment herein, the methods for imaging cancer as described herein may include administering the compound of Formula (I), or a pharmaceutically acceptable salt and/or solvate thereof, to a subject at a concentration (i.e., activity) ranging from about 0.01 mCi to about 10 mCi. Suitable concentrations (i.e., activity) may include about 0.01 mCi, about 0.02 mCi, about 0.03 mCi, about 0.04 mCi, about 0.05 mCi, about 0.06 mCi, about 0.07 mCi, about 0.08 mCi, about 0.09 mCi, about 0.1 mCi, about 0.2 mCi, about 0.3 mCi, about 0.4 mCi, about 0.5 mCi, about 0.6 mCi, about 0.7 mCi, about 0.8 mCi, about 0.9 mCi, about 1.0 mCi, about 1.5 mCi, about 2.0 mCi, about 2.5 mCi, about 3.0 mCi, about 3.5 mCi, about 4.0 mCi, about 4.5 mCi, about 5.0 mCi, about 5.5 mCi, about 6.0 mCi, about 6.5 mCi, about 7.0 mCi, about 7.5 mCi, about 8.0 mCi, about 8.5 mCi, about 9.0 mCi, about 9.5 mCi, about 10.0 mCi, or any range including and/or in between any two of the preceding values. For example, in any embodiment herein, the concentration may be from about 0.01 mCi to about 5 mCi, about 0.1 mCi to about 5 mCi, about 0.5 mCi to about 5 mCi, about 1 mCi to about 5 mCi, about 1 mCi to about 10 mCi, about 5 mCi to about 10 mCi, or any range including and/or in between any two of the preceding values.

In any embodiment herein, the methods for imaging cancer as described herein may include administering the compound of Formula (I), or a pharmaceutically acceptable salt and/or solvate thereof, to a subject at mass that may be less than about 100 mmol (or 100 mg). For example, in any embodiment herein, the mass may be about 0.001 nmol to about 99 mmol. Suitable mass amounts may include, but are not limited to, about 0.01 nmol, about 0.01 nmol, about 0.1 nmol, about 1 nmol, about 10 nmol, about 50 nmol, about 100 nmol, about 200 nmol, about 300 nmol, about 400 nmol, about 500 nmol, about 600 nmol, about 700 nmol, about 800 nmol, about 900 nmol, about 1 mmol, 5 mmol, about 10 mmol, about 15 mmol, about 20 mmol, about 25 mmol, about 30 mmol, about 35 mmol, about 40 mmol, about 45 mmol, about 50 mmol, about 55 mmol, about 60 mmol, about 65 mmol, about 70 mmol, about 75 mmol, about 80 mmol, about 85 mmol, about 90 mmol, about 95 mmol, about 100 mmol, or any range including and/or in between any two of the preceding values.

In any embodiment herein, the method may include administering the compound of Formula (I), or a pharmaceutically acceptable salt and/or solvate thereof, to a subject prior to, or during, a PET scan. In any embodiment herein, the administering may be prior to a PET scan. In any embodiment herein, the administering may be during a PET scan.

In any embodiment herein, upon administering to a subject (such as a human), the compound of Formula (I), or a pharmaceutically acceptable salt and/or solvate thereof, may be visible under the PET scanner for a duration of about 0 min to about 8 h post-administration. Suitable durations include, but are not limited to, about 0.5 min, about 1 min, about 5 min, about 10 min, about 15 min, about 30 min, about 45 min, about 1 h, about 1.5 h, about 2 h, about 2.5 h, about 3 h, about 3.5 h, about 4 h, about 4.5 h, about 5 h, about 5.5 h, about 6 h, about 6.5 h, about 7 h, about 7.5 h, about 8 h, or any range including and/or in between any two of the preceding values. If not physiologically removed, upon administering to a subject, the compound of Formula (I), or a pharmaceutically acceptable salt and/or solvate thereof, may be visible at the site of interest in the fluorescence mode for at least about 24 hours post-injection. In any embodiment herein, upon administering to a subject, the compound of Formula (I), or a pharmaceutically acceptable salt and/or solvate thereof, may be used to visualize dynamic processes.

In one particular embodiment, the method may include following general human dosing, where the method may include: administering the compound of Formula (I) as described herein in any embodiment, or a pharmaceutically acceptable salt and/or solvate thereof, at a concentration (i.e., activity) ranging from about 0.1 to about 10 mCi, and mass that may be less than about 100 mmol (or 100 mg), wherein the compound may be administered intravenously, orally, intra-tumorally, or injected in relevant fatty tissue prior to, or during, a PET scan. In any embodiment herein, the co-injected, residual $[^{18/19}F]$—$BF_2$ agent (i.e., a compound of Formula (I), or a pharmaceutically acceptable salt and/or solvate thereof) may be visible under the PET scanner from 0 min to about 8 hours post-injection and may be used to visualize dynamic processes. If not physiologically removed, the co-injected or residual $[^{18/19}F]$—$BF_2$ may be visible at the site of interest in the fluorescence mode for at least about 24 hours post-injection.

Figure 9A:
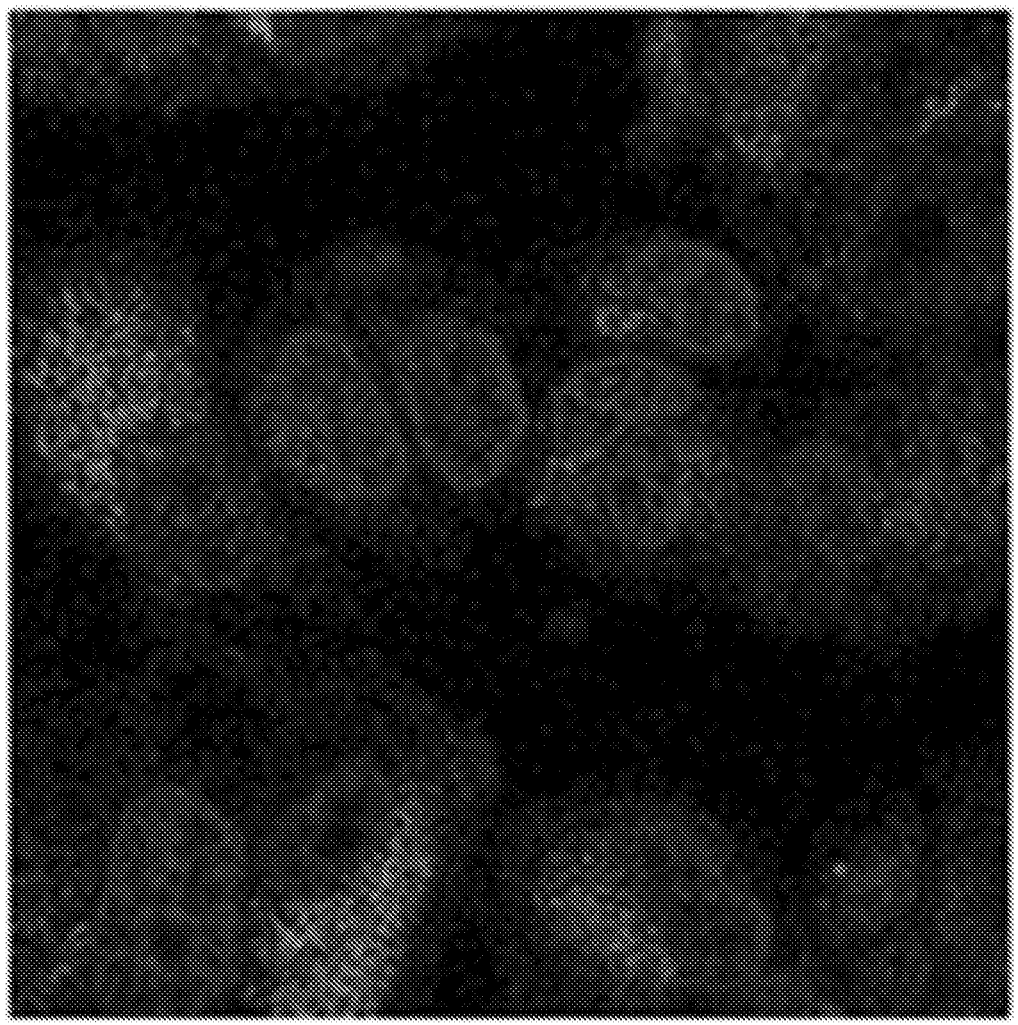
FIGS. 9A-C illustrate the labeling of MCF7 breast cancer cells with curcumin (FIG. 9A), Cur-BF$_2$ (FIG. 9B), and DAPI nuclear stain (FIG. 9C), according to the working examples.
Figure 9B:
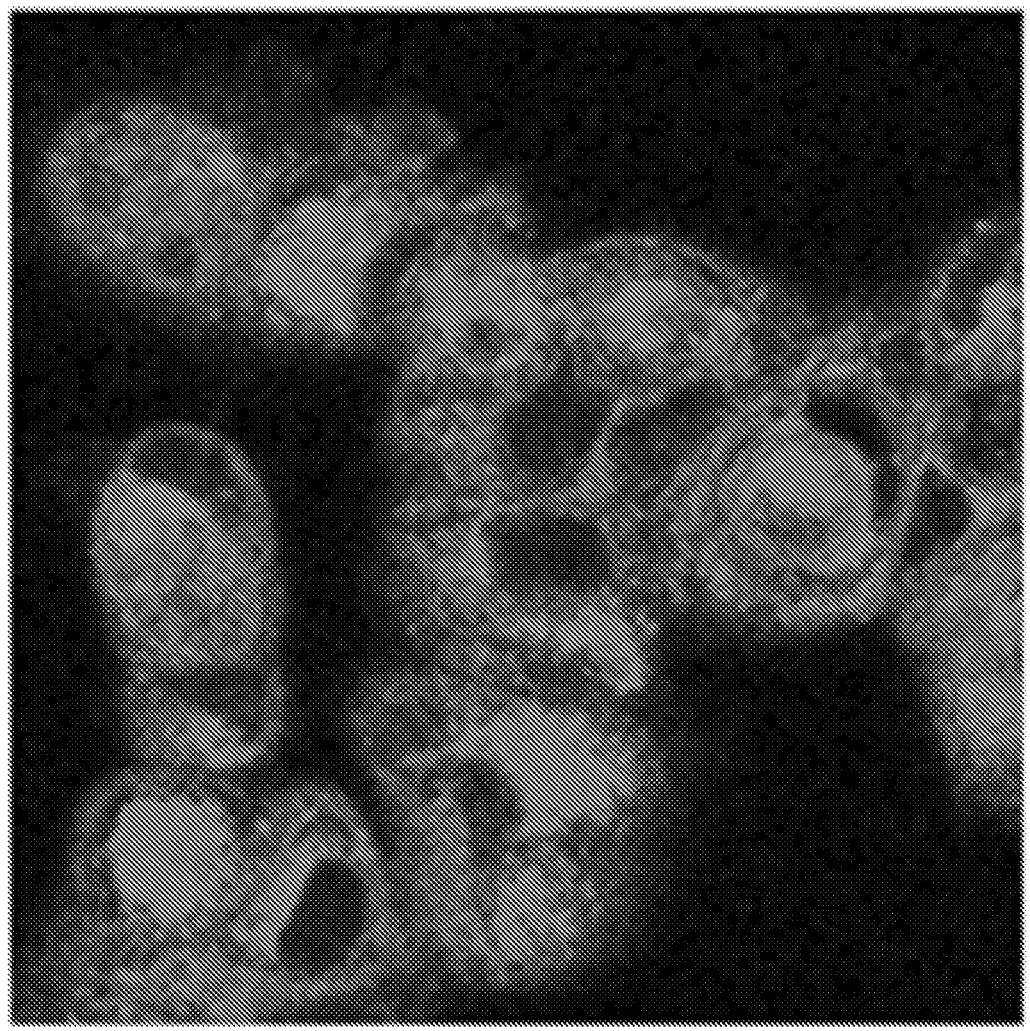
Figure 9C:
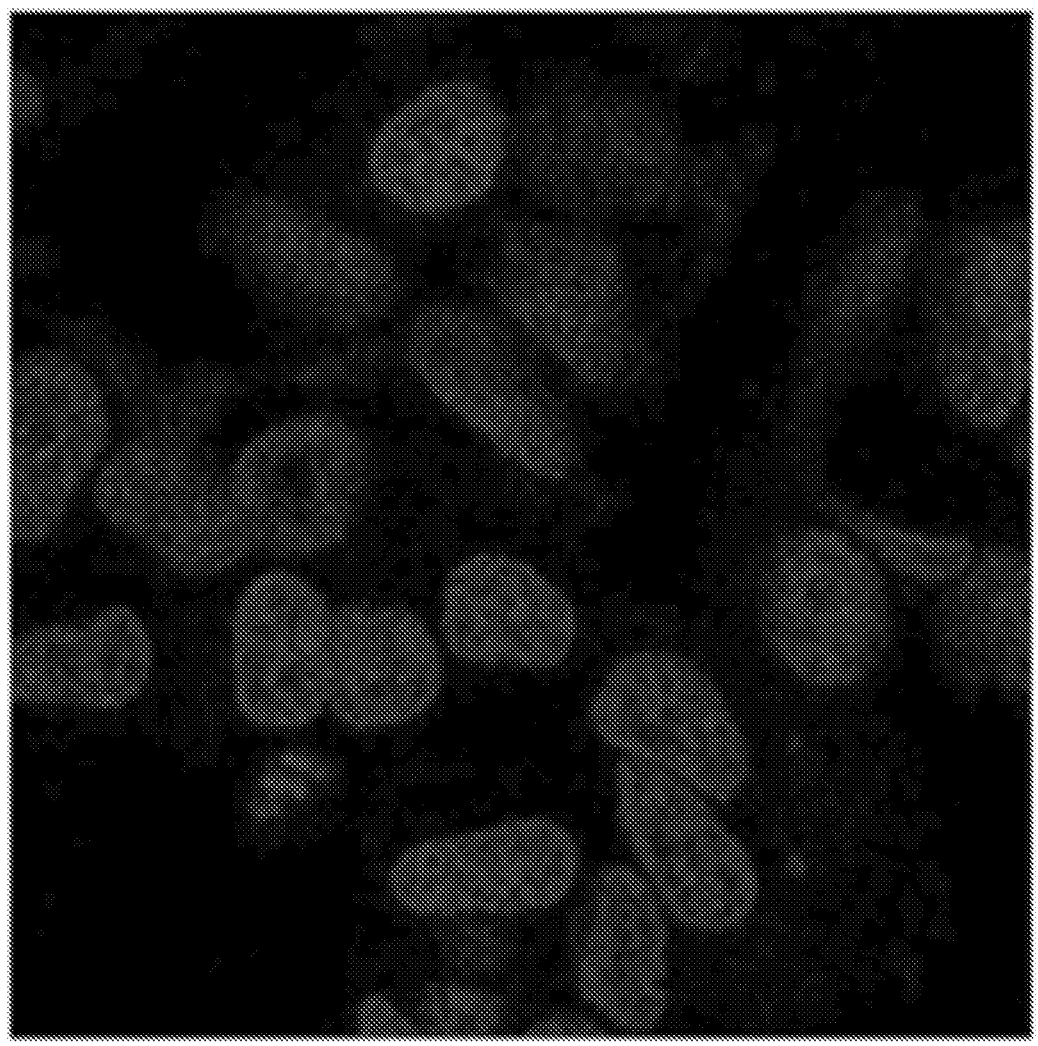
Figure 10A:
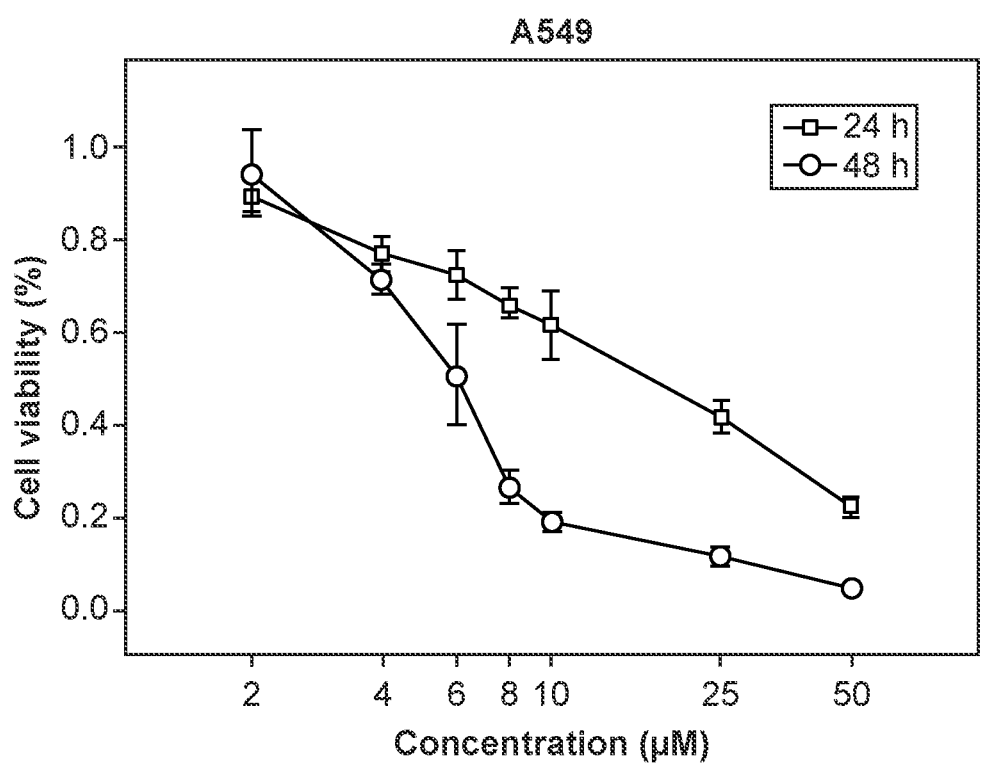
FIGS. 10A-E illustrate inhibition of cell proliferation (IC$_{50}$, MTS) by Cur-BF$_2$ on cancer cell lines A549 (FIG. 10A), HeLa (FIG. 10B), HCT116 (FIG. 10C), MDA-MB-231 (FIG. 10D), and MCF-7 (FIG. 10E), according to the working examples.
Figure 10B:
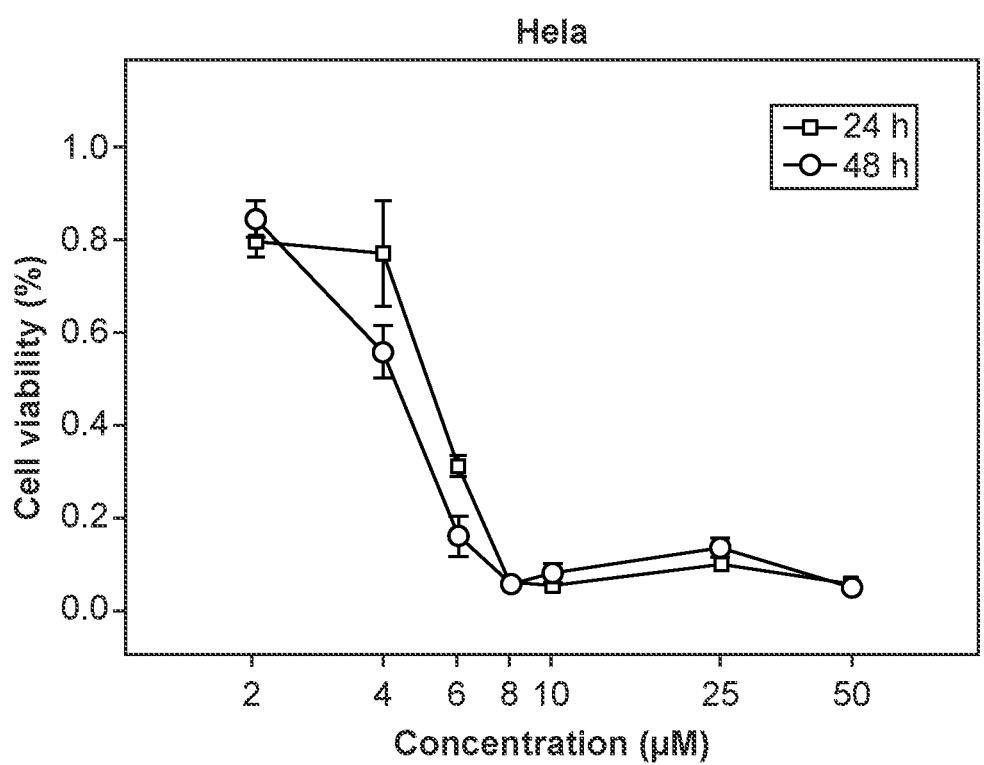
Figure 10C:
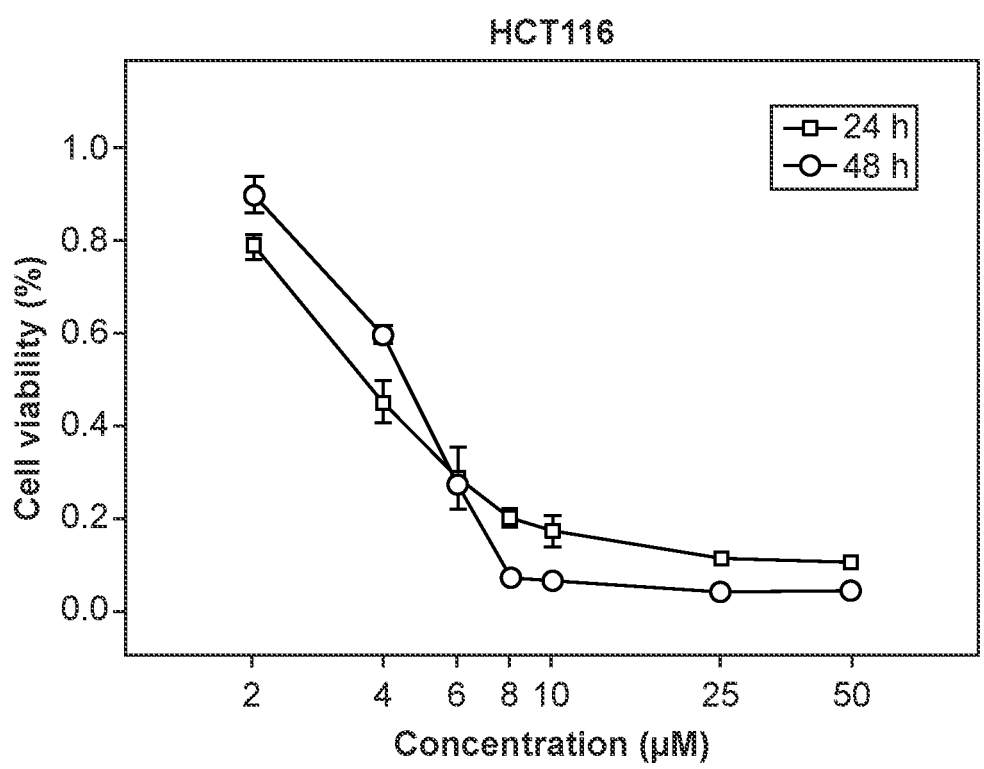
Figure 10D:
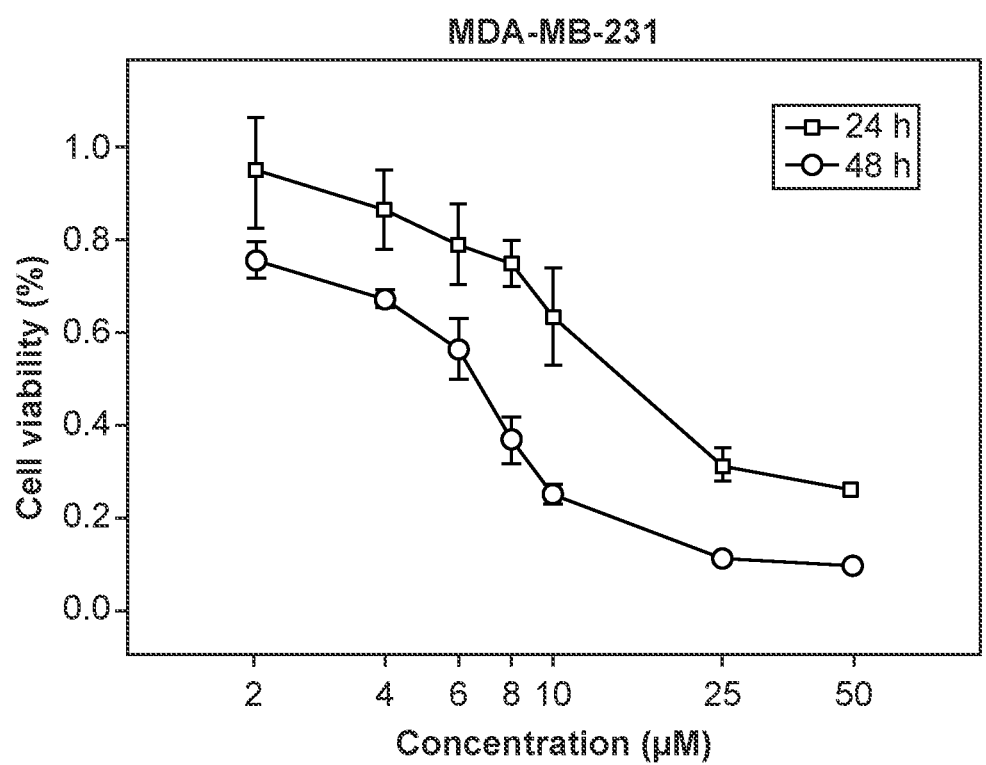
Figure 10E:
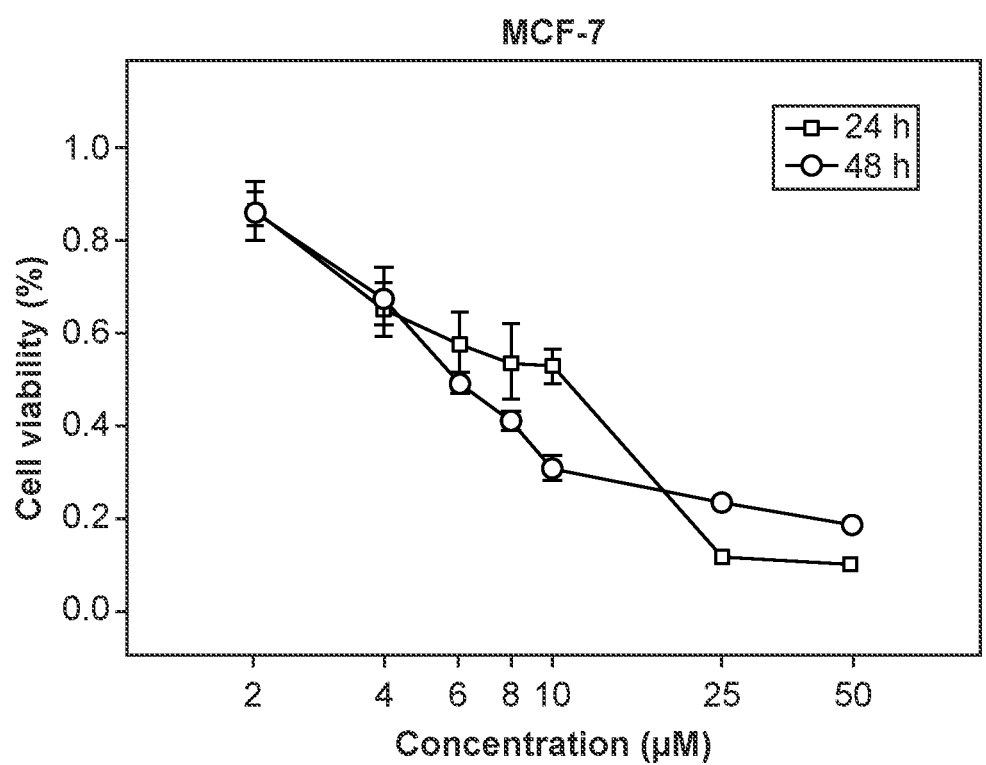
Figure 11A:
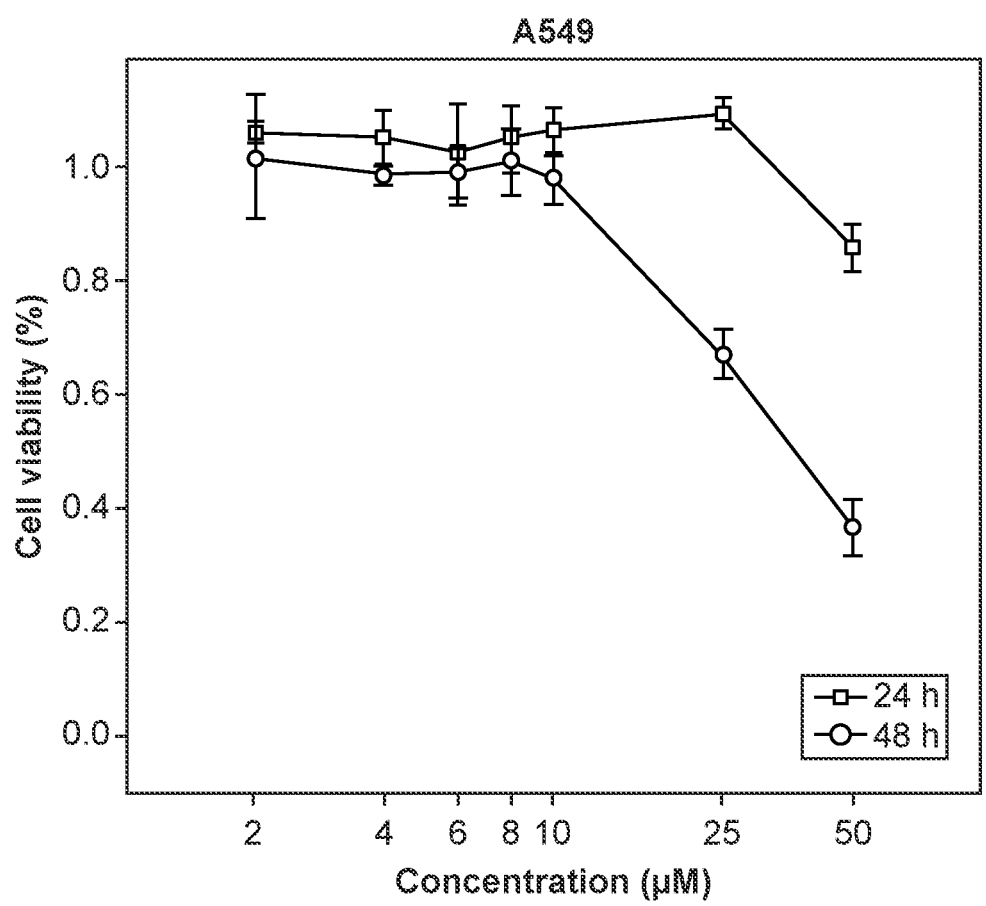
FIGS. 11A-E provide the results of inhibition of cell proliferation (IC$_{50}$, MTS) by control on cancer cell lines A549 (FIG. 11A), HeLa (FIG. 11B), HCT116 (FIG. 11C), MDA-MB-231 (FIG. 111D), and MCF-7 (FIG. 11E), according to the working examples.
Figure 11B:
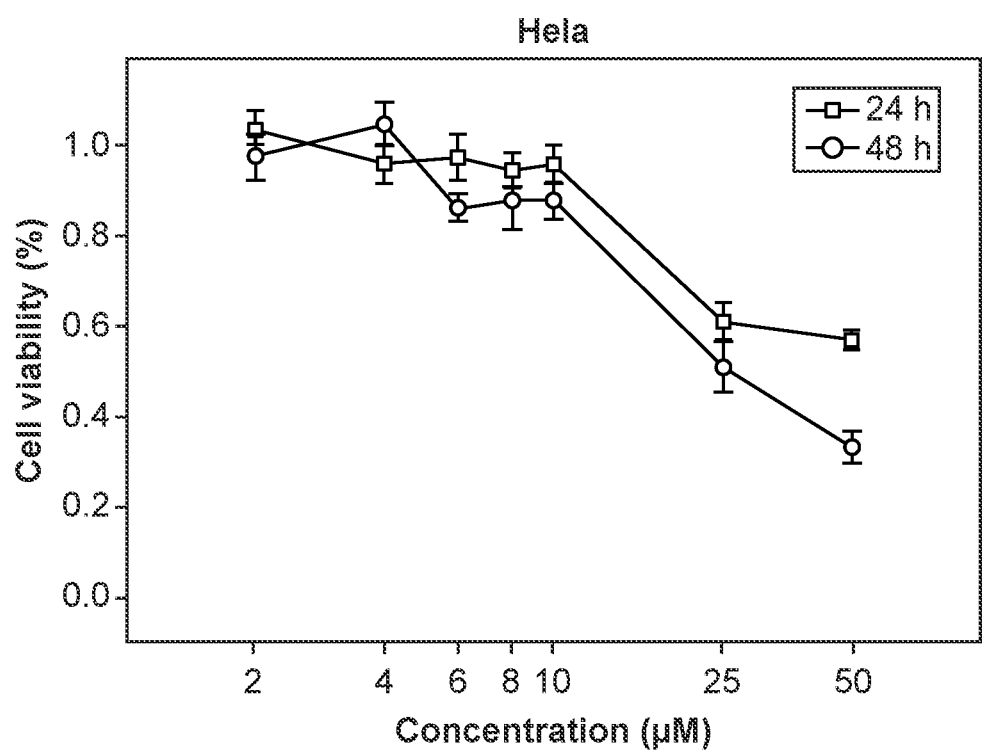
Figure 11C:
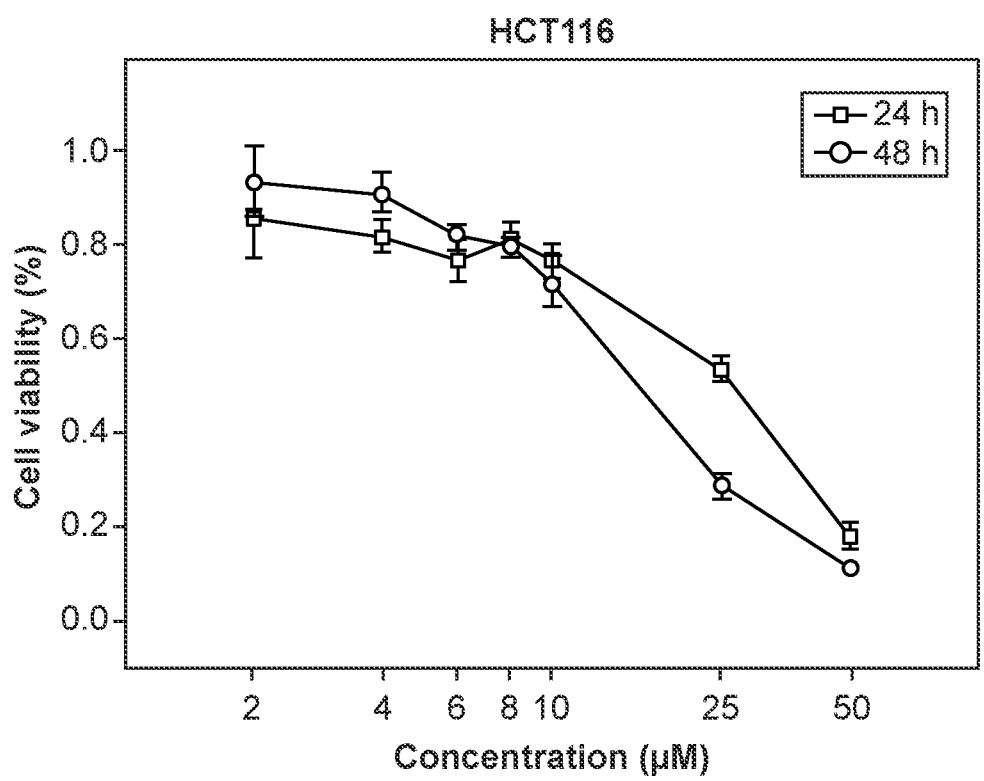
Figure 11D:
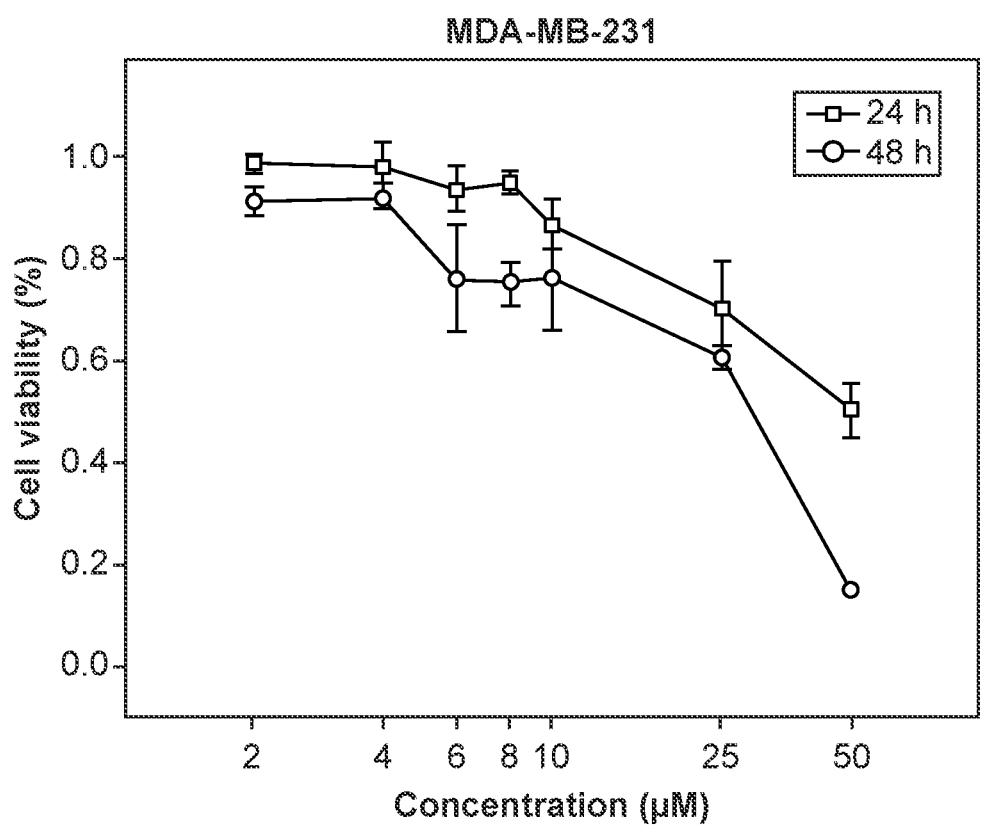
Figure 11E:
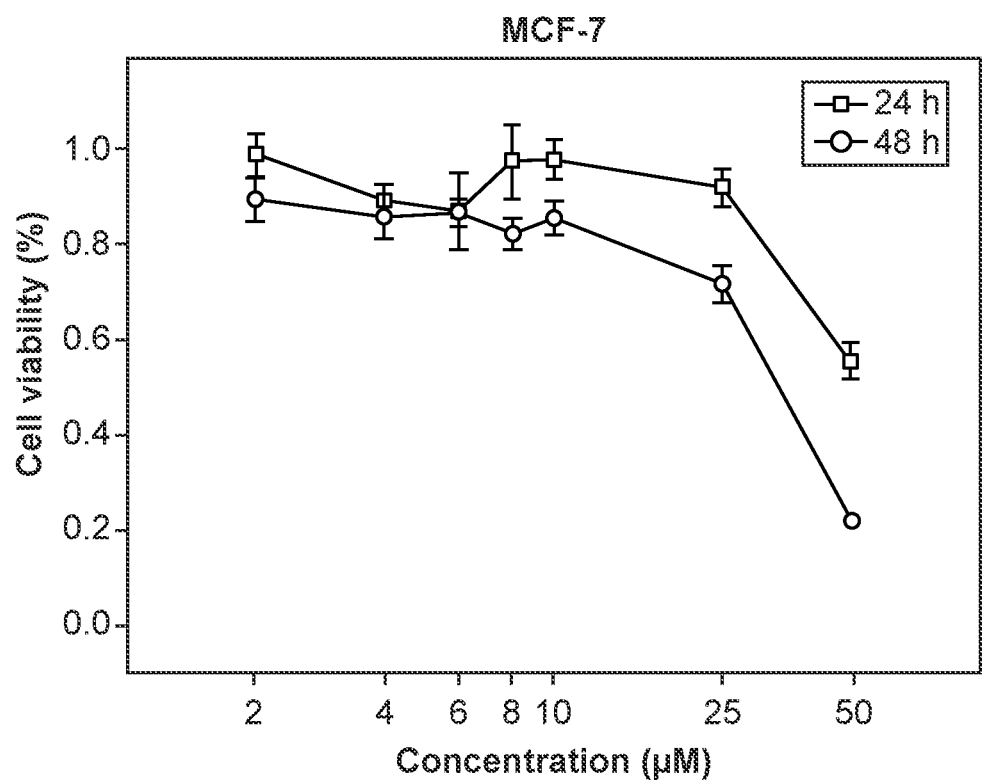

In another particular embodiment, the method may include following general human dosing, where the method may include: administering the compound of Formula (I) as described herein in any embodiment, or a pharmaceutically acceptable salt and/or solvate thereof, at a concentration (i.e., activity) ranging from about 0.01 to about 5 mCi, and mass that is less than about 100 mmol (e.g., 100 mg), is injected intra-tumorally or in relevant fatty tissue prior to, or during, a PET scan, where the imaging is for lymphatic system mapping. Co-injected, residual $[^{18/19}F]$—$BF_2$ agent (i.e., a compound of Formula (I), or a pharmaceutically acceptable salt and/or solvate thereof) may be visible under the PET scanner from 0 min to about 8 hours post-injection and may be used to visualize dynamic, lymphatic flow. For example, in any embodiment herein, the co-injected or residual $[^{18/19}F]$—$BF_2$ may be Curcumin-$BF_2$ $[^{18}F]$. In any embodiment herein, the Curcumin-$BF_2$ may be visible in the lymph nodes in vivo or ex vivo for at least 24 hours post-injection. FIGS. 9A-9C shows imaging according to an exemplary embodiment of the methods described herein labeling MCF7 breast cancer cells with curcumin (FIG. 9A), Cur-$BF_2$ (FIG. 9B), or DAPI nuclear stain (FIG. 9C).

In a related aspect, the present technology provides a method for inhibiting the proliferation of one or more cancer cells, where the method includes contacting the one or more cancer cells with a compound of Formula (I) as described herein in any embodiment, or a pharmaceutically acceptable salt and/or solvate thereof. For example, in any embodiment herein, the compound of Formula (I), or a pharmaceutically acceptable salt and/or solvate thereof, may be Curcumin-$BF_2$. In any embodiment herein, the method may include contacting the one or more cancer cells with a pharmaceutical composition as described herein in any embodiment.

In any embodiment herein, the one or more cancer cells may include, but are not limited to, lung cancer cells (e.g., A549), HeLa cells, colon cancer cells (e.g., HCT116 cells), MDA-MB-231 cells, breast cancer cells (e.g., MCF-7 cells), or a combination of any two or more thereof. For example, the method may include contacting a compound of Formula (I) as described herein in any embodiment, or a pharmaceutically acceptable salt and/or solvate thereof, with one or more cancers cells that include A549, HeLa, HCT116, MDA-MB-231, MCF-7, or any combination of two or more thereof.

In yet another aspect, the present technology provides a method for treating cancer in a subject, wherein the method includes administering to the subject in need thereof a therapeutically effective amount of a compound of Formula (I) as described herein in any embodiment, or a pharmaceutically acceptable salt and/or solvate thereof. In any embodiment herein, the compound of Formula (I) as described herein in any embodiment, or a pharmaceutically acceptable salt and/or solvate thereof, may be Curcumin-$BF_2$. In any embodiment herein, the method may include administering to the subject in need thereof a pharmaceutical composition, as described herein in any embodiment, that includes the compound of Formula (I) as described herein in any embodiment, or a pharmaceutically acceptable salt and/or solvate thereof, and a pharmaceutically acceptable carrier.

In any embodiment herein, the method may include treating cancer in a subject in need thereof, where the subject may be suffering from a cancer as defined herein in any embodiment. For example, in any embodiment herein, the subject may be suffering from colon cancer, breast cancer, or lung cancer.

As used in this disclosure, the term "therapeutically effective" amounts of the compound of Formula (I) as described herein in any embodiment, or a pharmaceutically acceptable salt and/or solvate thereof, refers to amounts that may include, but are not limited, about 0.1 mCi per dose to about 100 mCi per dose. For example, in any aspect or embodiment herein, the therapeutically effective amount may be from about 0.1 mCi per dose to about 0.5 mCi per dose, from about 0.5 mCi per dose to about 1.0 mCi per dose, from about 1.0 mCi per dose to about 2.5 mCi per dose, from about 2.5 mCi per dose to about 5.0 mCi per dose, from about 5.0 mCi per dose to about 7.5 mCi per dose, from about 7.5 mCi per dose to about 10.0 mCi per dose, from about 10.0 mCi per dose to about 12.5 mCi per dose, from about 12.5 mCi per dose to about 15 mCi per dose, from about 15 mCi per dose to about 20 mCi per dose, from about 20 mCi per dose to about 50 mCi per dose, from about 50 mCi per dose to about 100 mCi per dose, or any range including and/or in between any two of the preceding values.

Suitable therapeutically effective amounts of the compound of Formula (I) as described herein in any embodiment, or a pharmaceutically acceptable salt and/or solvate thereof, may include about 0.1 mCi per dose, about 0.5 mCi per dose, about 1.0 mCi per dose, about 2.5 mCi per dose, about 5.0 mCi per dose, about 7.5 mCi per dose, about 10.0 mCi per dose, about 12.5 mCi per dose, about 15 mCi per dose, about 20 mCi per dose, about 50 mCi per dose, about 100 mCi per dose, or any range including and/or in between any two of the preceding values.

In any embodiment herein, the method of treating cancer in a subject in need thereof may include a dosing regimen for administering the compound of Formula (I) as described herein in any embodiment, or a pharmaceutically acceptable salt and/or solvate thereof. In any embodiment herein, the dosing regimen may include, but is not limited to, a dosing interval from about one week to about three months. Suitable dosing intervals may include about 1 week, about 2 weeks, about 3 weeks, about 1 month, about 1.5 months, about 2 months, about 2.5 months, about 3 months, or any range including and/or in between any two of the preceding values. In any embodiment herein, the dosing regimen may include dosage amounts totaling 1 dose, 2 doses, 3 doses, 4 doses, 5 doses, 6 doses, 7 doses, 8 doses, 9 doses, 10 doses, 11 doses, 12 doses, or any range including and/or in between these values.

In any embodiment herein, the method of treating cancer in a subject in need thereof may further include performing the method in conjunction with the method of administering an effective amount of the compound of Formula (I), or a pharmaceutically acceptable salt and/or solvate thereof, or a pharmaceutical composition as described herein in any embodiment for imaging the cancer. For example, in any embodiment herein, the compound of Formula (I), or a pharmaceutically acceptable salt and/or solvate thereof, or a pharmaceutical composition as described herein may be administered intravenously, orally or intra-tumorally to a subject, wherein the subject may be undergoing imaging via a PET/CT or PET/MR imaging platform during and/or post-administration.

In any embodiment herein, the combined methods may include administration of the compound of Formula (I), or a pharmaceutically acceptable salt and/or solvate thereof, as described herein in any embodiment may include dosage concentrations from about 0.01 to about 10 mCi. Suitable concentrations may include about 0.01 mCi, about 0.02 mCi, about 0.03 mCi, about 0.04 mCi, about 0.05 mCi, about 0.06 mCi, about 0.07 mCi, about 0.08 mCi, about 0.09 mCi, about 0.1 mCi, about 0.2 mCi, about 0.3 mCi, about 0.4 mCi, about 0.5 mCi, about 0.6 mCi, about 0.7 mCi, about 0.8 mCi, about 0.9 mCi, about 1.0 mCi, about 1.5 mCi, about 2.0 mCi, about 2.5 mCi, about 3.0 mCi, about 3.5 mCi, about 4.0 mCi, about 4.5 mCi, about 5.0 mCi, about 5.5 mCi, about 6.0 mCi, about 6.5 mCi, about 7.0 mCi, about 7.5 mCi, about 8.0 mCi, about 8.5 mCi, about 9.0 mCi, about 9.5 mCi, about 10.0 mCi, or any range including and/or in between any two of the preceding values. For example, in any embodiment herein, the concentration may be from about 0.01 mCi to about 5 mCi, about 0.1 mCi to about 5 mCi, about 0.5 mCi to about 5 mCi, about 1 mCi to about 5 mCi, about 1 mCi to about 10 mCi, about 5 mCi to about 10 mCi, or any range including and/or in between any two of the preceding values.

In any embodiment herein, the combined methods may include administration of a dosage that includes a mass of about 0.1 µg to about 500 µg of the compound of Formula (I) as described herein in any embodiment, or a pharmaceutically acceptable salt and/or solvate thereof. Suitable dosages may include a mass of about 0.1 µg, about 0.5 µg, about 1 µg, about 5 µg, about 10 µg, about 20 g, about 30 µg, about 40 µg, about 50 µg, about 60 µg, about 70 µg, about 80 µg, about 90 µg, about 100 µg, about 125 µg, about 150 µg, about 175 µg, about 200 µg, about 225 µg, about 250 µg, about 275 µg, about 300 µg, about 325 µg, about 350 µg, about 375 µg, about 400 µg, about 425 µg, about 450 µg, about 475 µg, about 500 µg, or any range including and/or in between any two or more of the preceding values, of the compound of Formula (I) as described herein in any embodiment, or a pharmaceutically acceptable salt and/or solvate thereof.

In any embodiment herein, the combined methods may include administration of a dosage in a volume from about 1 mL to about 250 mL at a rate of about 0.1 to about 1 mL/min initiated during a PET scan. Suitable volumes may include, but are not limited to, about 1 mL, about 10 mL, about 25 mL, about 50 mL about 75 mL, about 100 mL, about 125 mL, about 150 mL, about 175 mL, about 200 mL, about 225 mL, about 250 mL, or any range including and/or in between any two of the preceding values. Suitable rates may include, but are not limited to, about 0.1 mL/min, 0.2 mL/min, about 0.3 mL/min, about 0.4 mL/min, about 0.5 mL/min, about 0.6 mL/min, about 0.7 mL/min, about 0.8 mL/min, about 0.9 mL/min, about 1 mL/min, or any range including and/or in between any two of the preceding values. In any embodiment herein, a delay may be introduced between the PET scan start and administration of the dosage to ensure initial delivery is captured. For example, in any embodiment herein, administration of doses may range from about 0.01 to about 1 mCi and may have a mass of less than about 0.1 g to about 500 mg of the compound of Formula (I) as described herein in any embodiment, or a pharmaceutically acceptable salt and/or solvate thereof, would be performed as needed. Here, CT or MR imaging may be performed weekly or monthly following image-guided delivery, and tumor progression (e.g., volume) would be tracked and monitored as a function of variables associated with PET image-guided drug delivery (e.g., activity of drug delivered to the tumor, saturation of drug delivery to a tumor volume, and/or rate of drug clearance from the delivery site).

Kits

In a further related aspect, the present technology provides a kit for imaging of cancer, inhibiting proliferation of cancer cells, and/or treating cancer in a subject in need thereof, that includes a compound according to Formula (Ia):

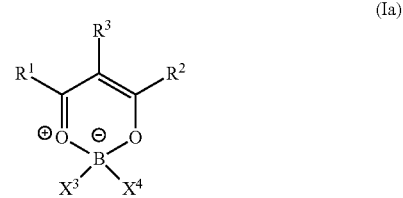

(Ia)

or a pharmaceutically acceptable salt and/or solvate thereof, wherein $X^3$ and $X^4$ are each independently $^{19}F$; and $R^1$, $R^2$, and $R^3$ are defined as described herein in any embodiment regarding Formula (I).

Optionally, the above described components of the kits of the present technology may be packed in suitable containers and labeled for imaging of cancer, inhibiting proliferation of cancer cells, and/or treating cancer in a subject in need thereof.

The above-mentioned components may be stored in unit or multi-dose containers, for example, sealed ampoules, vials, bottles, syringes, and test tubes, as an aqueous, preferably sterile, solution or as a lyophilized, preferably sterile, formulation for reconstitution. The kit may further include a second container that holds a diluent suitable for diluting the composition of Formula (Ia), or a pharmaceutically acceptable salt and/or solvate thereof, towards a higher volume. Suitable diluents include, but are not limited to, dry polar aprotic solvents. Polar aprotic solvents as used herein may include, but are not limited to, ethers (e.g., tetrahydrofuran (THF), 2-methyltetrahydrofuran (2Me-THF), dimethoxyethane (DME), dioxane), esters (e.g., ethyl acetate, isopropyl acetate), ketones (e.g., acetone, methylethyl ketone, methyl isobutyl ketone), carbonates (e.g., ethylene carbonate, propylene carbonate, trimethylene carbonate), amides (e.g., dimethylformamide (DMF), dimethylacetamide (DMA)), nitriles (e.g., acetonitrile ($CH_3CN$), propionitrile ($CH_3CH_2CN$), benzonitrile (PhCN)), sulfoxides (e.g., dimethyl sulfoxide), sulfones (e.g., sulfolane), or a mixture of any two or more thereof. In any embodiment herein, the dry solvent may be dry acetonitrile. As used herein, the term "dry" refers to solvents that are anhydrous (i.e., do not contain water).

In any embodiment herein, the kit may further include a third container that includes a precursor solution of a transition metal halide (i.e., transition metal halide solution). Suitable transition metal halide solutions may include solutions containing a soluble halide of tin (IV), or other fluorophilic transition metal or metal-complex.

The kit of any embodiment herein may include instructions for imaging of cancer, inhibiting proliferation of cancer cells, and/or treating cancer in a subject in need thereof. The kit of any embodiment herein may include instructions describing a method of any aspect or embodiment of the present disclosure. Furthermore, the kit may comprise instructions for diluting the composition of Formula (Ia), or a pharmaceutically acceptable salt and/or solvate thereof, and/or instructions for administering the composition of Formulae (I) or (Ia), or a pharmaceutically acceptable salt and/or solvate thereof, whether diluted or not. The containers may be formed from a variety of materials such as glass or plastic and may have a sterile access port (for example, the container may be an intravenous solution bag or a vial having a stopper which may be pierced by a hypodermic injection needle). The kit may further include more containers that include a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. The kits may optionally include instructions customarily included in commercial packages of therapeutic or diagnostic products, that contain information about, for example, the indications, usage, dosage, manufacture, administration, contraindications and/or warnings concerning the use of such therapeutic or diagnostic products.

The kit may further include, e.g., a buffering agent, a preservative or a stabilizing agent. The kit may also include a control sample or a series of control samples, which may be assayed and compared to the test sample. Each component of the kit can be enclosed within an individual container and all of the various containers may be within a single package, along with instructions for preparing the $^{18}$F-exchanged radiolabeled compound of Formula (I), or a pharmaceutically acceptable salt and/or solvate thereof, and administering said $^{18}$F compounds using the kit. The kits of the present technology may contain a written product on or in the kit container. The written product describes how to use the reagents contained in the kit. In certain embodiments, the use of the reagents can be according to the methods of the present technology. The kit may further include a purification cartridge to purify compositions that include the $^{18}$F exchange radiolabeled compound of Formula (I), or a pharmaceutically acceptable salt and/or solvate thereof, prior to administering to a subject according to the methods of the present technology.

In any embodiment herein, the kits of the present technology generally include a $^{19}$F-bearing or boronic ester fluorescent precursor as a targeted biological agent (i.e., the compound of Formula (Ia)) or a NHS ester for general reaction. In any embodiment herein, the kit may include a pharmaceutical composition that includes the compound of Formula (Ia), or a pharmaceutically acceptable salt and/or solvate thereof, and a diluent. Aliquots of these compositions would be mixed with $^{18}$F-containing acidic water to give a $^{18}$F-bearing PET-visible compound of Formula (I), or a pharmaceutically acceptable salt and/or solvate thereof. The composition may then be passed over a commercial column to remove contaminating fluoride ions prior to administration to a subject (e.g., via injection).

Examples of kit-based preparations include, but are not limited to, protocols described in the following, which are incorporated herein by reference: (i) (preparation from a boronic ester)—Wang, Y., An, F., Chan, M., Friedman, B., Rodriguez, E. A., Tsien, R. Y., Aras, O., and Ting, R. (2017) "18F-positron-emitting/fluorescent labeled erythrocytes allow imaging of internal hemorrhage in a murine intracranial hemorrhage model." J. Cerebral Blood Flow and Metabolism., 37(3), 776-786. PMID: 28054494; (ii) (preparation from a 19F-bearing molecule)—Kommidi, H., Guo, H. Nurili, F., Vedvyas, Y., Jin, M. M., McClure, T., D., Ehdaie, B., Sayman, H., Akin O., Aras, O., Ting, R. (2018) "18F-positron emitting/trimethine cyanine-fluorescent contrast for image-guided prostate cancer management." J. Med. Chem. 61, 4256-4262; and Konunidi, H., Guo, H., Chen, N., Kim, D., He, B., Wu, A. P., Aras, O, Ting, R. (2017) "A [18F]-positron-emitting, fluorescent, cerebrospinal fluid probe for imaging damage to the brain and spine." Theranostics. 7, 2377-2391. (Cover article) PMID: 28744321.

In any embodiment herein, the kit may be a Curcumin-$BF_2$ kit that includes (a) dry Curcumin-$BF_2$, (b) a solution of tin(IV) chloride, and (c) dry acetonitrile (e.g., HPLC grade). In any embodiment herein, the kit may include instructions for a user, where the user would provide their own $^{18}$F-fluoride ion (e.g., obtained from a cyclotron). Following drying the $^{18}$F-fluoride, the user would mix all reagents. For Curcumin-$BF_2$, no purification cartridge may be needed, however, the Curcumin-$BF_2$ may be purified as described herein. Herein, the user would simply precipitate out Curcumin-$BF_2$ with water, wash a few times with water to remove all fluoride ion, then resuspend Curcumin-$BF_2$ in a PBS-buffered DMSO solution that would be passed over a 0.22 μm filter for Curcumin-$BF_2$ for administering (e.g., intra-tumorally).

The present technology, thus generally described, will be understood more readily by reference to the following examples, which are provided by way of illustration and are not intended to be limiting of the present technology.

EXAMPLES

The difluoro-dioxaborinins of the present disclosure were synthesized from α,γ-diketones as shown in Scheme 1a and the procedures outlined in Example 1. The difluoro-dioxaborinins were subsequently radiolabeled as shown in Scheme 1b, according the procedures of Example 2. Finally the pseudo [$H_2O$]-dependent first order solvolysis of the radiolabeled difluoro-dioxaborinins underwent first order solvolysis as shown in Scheme 1c and discussed in Example 3 with half-lives ($t_{1/2}$) ranging from 3-130 hours.

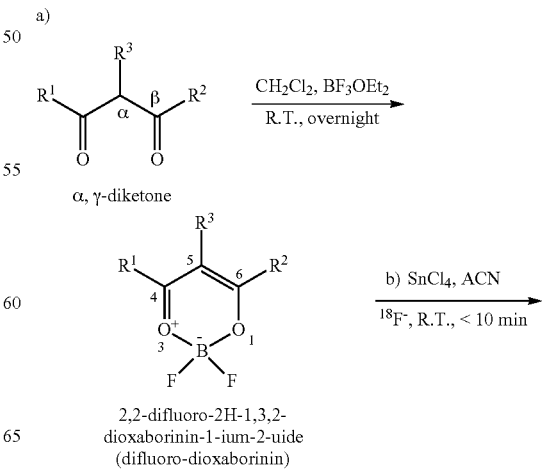

Scheme 1

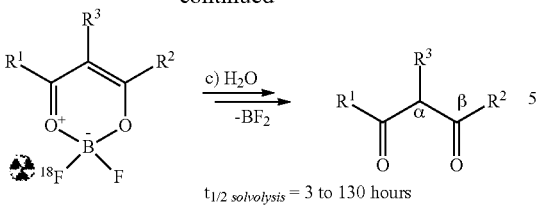

$t_{1/2\ solvolysis}$ = 3 to 130 hours

Example 1: Synthesis of Difluoro-Dioxaborinins from α,γ-Diketones

General synthesis and characterization parameters: Chemicals were purchased from Oakwood Chemical, Aldrich, Combi-blocks, Strem, and Alfa Aesar. Analytical, reverse phase UPLC were performed on a Waters Acquity H class HPLC/SQD2 mass spectrometer and a Phenomenex Kinetex 1.7 μm C18 100 Å, 50 cm×2.1 mm I.D. Column (00B-4475-AN), with a 1.5 min, a 10-90% H₂O:acetonitrile (ACN) (0.05% TFA) gradient and a flow rate of 0.6 mL/min (unless stated otherwise). Preparative HPLC was performed on an Agilent 1200 Series HPLC equipped on a Phenomenex Luna C18(2) 100 Å, 250 cm×21.20 mm I.D. 10 m reverse phase column (00G-4253-P0 AX), with a 20 min, a 10-90% H₂O:ACN (0.05% TFA) gradient and a flow rate of 12 mL/min. ¹H NMR were performed on a 500 MHz Bruker spectrometer. Yields for all compounds are 50-70%.

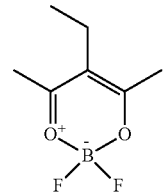

DK-1

General 2,2-difluoro-2H-1,3,2-dioxaborinin-1-ium-2-uide synthesis: The general synthesis of 2,2-difluoro-2H-1,3,2-dioxaborinin-1-ium-2-uide was performed as follows: 1,3-diketoalkane (3 mmol) was dissolved in 10 mL of dry CH₂Cl₂. BF₃·(OEt)₂ (6 mmol) was added to the solution dropwise, under magnetic stirring at room temperature. After two hours of reaction, 5 mL of deionized water was added to quench the reaction. The mixture was dried by rotary evaporation. Dried material was re-dissolved in DMF and purified by C18 reverse phase preparative chromatography. ¹H NMR (500 MHz, d6-DMSO, 21° C., TMS): δ 6.40 (s, 1H), 2.34 (s, 6H); ¹³C NMR (125 MHz, d6-DMSO, 21° C., TMS): δ 193.32, 102.72, 24.19; ¹⁹F NMR (470 MHz, d6-DMSO, 21° C., CFCl₃): [¹⁰B]—BF₂: δ −137.968 (18.8%), [¹¹B]—BF₂: δ −138.030 (81.2%); HRMS (ESI) calc'd for [M]=[C₅H₇BF₂O₂]: 148.0507, [M-H]−= [C₅H₆BF₂O₂]−: 147.0429, found [M-H]−: 147.0435.

DK-2

DK-2 was prepared according to the general synthesis for DK-1 above. ¹H NMR (500 MHz, d6-DMSO, 21° C., TMS): δ 2.36 (s, 6H), 1.90 (s, 3H); ¹³C NMR (125 MHz, d6-DMSO, 21° C., TMS): δ 191.18, 108.07, 23.25, 11.93; ¹⁹F NMR (470 MHz, d6-DMSO, 21° C., CFCl₃): [¹⁰B]—BF₂: δ −139.053 (18.3%), [¹¹B]—BF₂: δ −139.116 (81.7%); HRMS (ESI) calc'd for [M]=[C₆H₉BF₂O₂]: 162.0664, [M-H]−=[C₆H₈BF₂O₂]−: 161.0585, found [M-H]−: 161.0590.

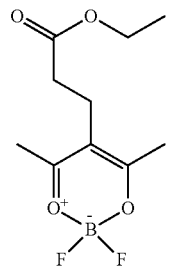

DK-3

DK-3 was prepared according to the general synthesis for DK-1 above. ¹H NMR (500 MHz, d6-DMSO, 21° C., TMS): δ 2.39 (J=1.7 Hz, 6H), 2.36 (J=7.5 and 1.7 Hz, 2H), 1.04 (J=7.5 Hz, 3H); ¹³C NMR (125 MHz, d6-DMSO, 21° C., TMS): δ 191.52, 114.08, 22.63, 19.56, 13.95; ¹⁹F NMR (470 MHz, d6-DMSO, 21° C., CFCl₃): [¹⁰B]—BF₂: δ −138.365 (18.9%), [¹¹B]—BF₂: δ −138.427 (81.1%); HRMS (ESI) calc'd for [M]=[C₇H₁₁BF₂O₂]: 176.0820, calc'd for [M-H]−=[C₇H₁₀BF₂O₂]−: 175.0742, found [M-H]−: 175.0748.

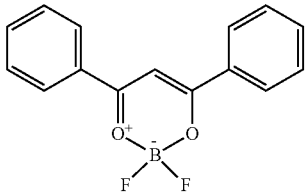

DK-6

DK-6 was prepared according to the general synthesis for DK-1 above. ¹H NMR (500 MHz, d6-DMSO, 21° C., TMS): δ 4.09 (q, J=7.1 Hz, 2H), 2.64 (t, J=7.8 Hz, 2H), 2.53 (t, J=7.8 Hz, 2H), 2.42 (s, 6H), 1.20 (t, J=7.1, 3H); ¹³C NMR (125 MHz, d6-DMSO, 21° C., TMS): δ 191.99, 172.51, 111.41, 60.51, 33.07, 32.98, 21.68, 14.52; ¹⁹F NMR (470 MHz, d6-DMSO, 21° C., CFCl₃): [¹⁰B]—BF₂: δ −138.494 (20.1%), [¹¹B]—BF₂: δ −138.556 (79.9%); HRMS (ESI) calc'd for [M]=[C₁₀H₁₆BF₂O₄]: 248.1031, calc'd for [M-H]−=[C₁₀H₁₅BF₂O₄]−: 247.0953, found [M-H]−: 247.0958.

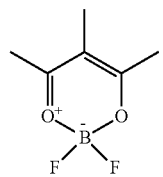

DK-13

DK-13 was prepared according to the general synthesis for DK-1 above. ¹H NMR (500 MHz, d6-DMSO, 21° C., TMS): δ 8.40 (d, J=7.7 Hz, 4H), 7.97 (s, 1H), 7.84 (t, J=7.4 Hz, 2H), 7.68 (t, J=7.7 Hz, 4H); ¹³C NMR (125 MHz, d6-DMSO, 21° C., TMS): δ 183.19, 136.39, 131.75, 129.89, 129.84, 95.02; ¹⁹F NMR (470 MHz, d6-DMSO, 21° C., CFCl₃): [¹⁰B]—BF₂: δ −139.304 (19.9%), [¹¹B]—BF₂: δ −139.367 (80.1%); HRMS (ESI) calc'd for [M]= [C₁₅H₁₁BF₂O₂]: 272.0820, found [M]−: 272.0823.

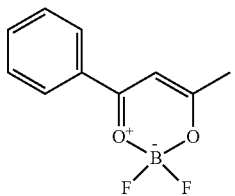

DK-14

DK-14 was prepared according to the general synthesis for DK-1 above. $^1$H NMR (500 MHz, d6-DMSO, 21° C., TMS): δ 8.19 (d, J=8.1 Hz, 2H), 7.82 (t, J=7.4 Hz, 1H), 7.66 (t, J=7.7 Hz, 2H), 7.29 (s, 1H), 2.49 (s, 3H); $^{13}$C NMR (125 MHz, d6-DMSO, 21° C., TMS): δ 194.96, 181.72, 136.27, 131.12, 129.98, 129.43, 98.78, 24.97; $^{19}$F NMR (470 MHz, d6-DMSO, 21° C., CFCl$_3$): [$^{10}$B]—BF$_2$: δ −138.460 (20.4%), [$^{11}$B]—BF$_2$: δ −138.523 (79.6%); HRMS (ESI) calc'd for [M]=[C$_{10}$H$_9$BF$_2$O$_2$]: 210.0664, calc'd for [M-H]—=[C$_{10}$H$_8$BF$_2$O$_2$]−: 209.0585, found [M-H]−: 209.0591.

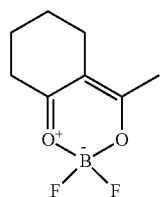

DK-15

DK-15 was prepared according to the general synthesis for DK-1 above. $^1$H NMR (500 MHz, d6-DMSO, 21° C., TMS): δ 2.57 (t, J=6.0 Hz, 2H), 2.37 (t, J=5.9 Hz, 2H), 2.34 (s, 3H), 1.72-1.65 (m, 4H); $^{13}$C NMR (125 MHz, d6-DMSO, 21° C., TMS): δ 193.23, 189.77, 109.60, 32.26, 22.76, 22.71, 21.73, 20.91; $^{19}$F NMR (470 MHz, d6-DMSO, 21° C., CFCl$_3$): [$^{10}$B]—BF$_2$: δ −138.361 (19.2%), [$^{11}$B]—BF$_2$: δ −138.423 (80.8%); HRMS (ESI) calc'd for [M]= [C$_8$H$_{11}$BF$_2$O$_2$]: 188.0820, calc'd for [M-H]−= [C$_8$H$_{10}$BF$_2$O$_2$]−: 187.0742, found [M-H]−: 187.0748.

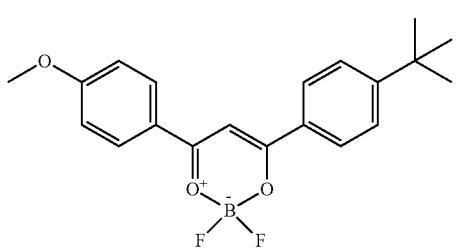

DK-16

DK-16 was prepared according to the general synthesis for DK-1 above. $^1$H NMR (500 MHz, d6-DMSO, 21° C., TMS): δ 8.39 (d, J=9.1 Hz, 2H), 8.29 (d, J=8.7 Hz, 2H), 7.81 (s, 1H), 7.67 (d, J=8.7 Hz, 2H), 7.21 (d, J=9.1 Hz, 2H), 3.94 (s, 3H), 1.34 (s, 9H); $^{13}$C NMR (125 MHz, d6-DMSO, 21° C., TMS): δ 181.78, 181.03, 166.18, 159.44, 132.62, 129.49, 129.44, 126.69, 123.95, 115.48, 93.68, 56.51, 35.68, 31.13; $^{19}$F NMR (470 MHz, d6-DMSO, 21° C., CFCl$_3$): [$^{10}$B]—BF$_2$: δ −140.117 (20.3%), [$^{11}$B]—BF$_2$: δ −140.179 (79.7%). HRMS (ESI) calc'd for [M]=[C$_{20}$H$_{21}$BF$_2$O$_3$]: 358.1552, found [M]−: 358.1549.

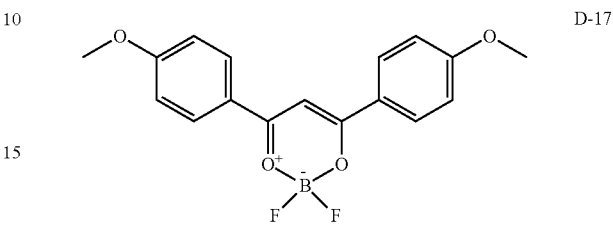

D-17

DK-17 was prepared according to the general synthesis for DK-1 above. $^1$H NMR (500 MHz, d6-DMSO, 21° C., TMS): δ 8.37 (d, J=9 Hz, 4H), 7.76 (s, 1H), 7.20 (d, J=9 Hz, 4H), 3.94 (s, 6H); $^{13}$C NMR (125 MHz, d6-DMSO, 21° C., TMS): δ 180.56, 165.81, 132.25, 124.17, 115.35, 92.87, 56.44; $^{19}$F NMR (470 MHz, d6-DMSO, 21° C., CFCl$_3$): [$^{10}$B]—BF$_2$: δ −140.493 (20.0%), [$^{11}$B]—BF$_2$: δ −140.556 (80.0%); HRMS (ESI) calc'd for [M]=[C$_{17}$H$_5$BF$_2$O$_4$]: 332.1031, found [M]−: 332.1031.

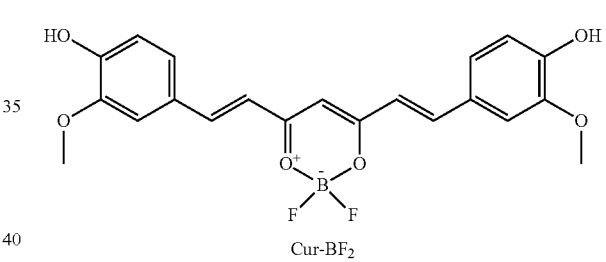

Cur-BF$_2$

Cur-BF$_2$ was prepared according to the general synthesis for DK-1 above. $^1$H NMR (500 MHz, d6-DMSO, 21° C., TMS): δ 10.10 (s, 2H), 7.92 (d, J=15.6 Hz, 2H, isomer, trans), 7.73 (d, J=8.6 Hz, 2H, isomer, cis), 7.47 (d, J=1.8 Hz, 2H), 7.34 (dd, J=8.3 Hz, 2H), 7.02 (d, J=15.6 Hz, 2H), 6.88 (d, J=8.2 Hz, 2H), 6.45 (s, 1H), 3.85 (s, 6H); $^{13}$C NMR (125 MHz, d6-DMSO, 21° C., TMS): δ 179.19, 151.81, 148.64, 147.42, 126.45, 125.70, 118.33, 116.42, 112.89, 101.55, 56.23; $^{19}$F NMR (470 MHz, d6-DMSO, 21° C., CFCl$_3$): δ A major product (A) and a minor isomer (B) are observed. (A) [$^{10}$B]—BF$_2$: δ −140.361 (34.7%), [$^{11}$B]—BF$_2$: δ −140.423 (65.3%) (Δ 0.062 ppm), (B) [$^{10}$B]—BF$_2$: δ −140.230 (16.7%), [$^{11}$B]—BF$_2$: δ −140.295 (83.3%) (Δ 0.065 ppm); HRMS (ESI) calc'd for [M]=[C$_{21}$H$_{19}$BF$_2$O$_6$]: 416.1243, calc'd for [M-H]—=[C$_{21}$H$_{18}$BF$_2$O$_6$]−: 415.1165, found [M-H]−: 415.1164. UPLC characterization: A 2 min, a 10-90 linear gradient (solvent A (0.05% TFA in H$_2$O) and solvent B (0.05% TFA in acetonitrile) were used to characterize Cur-BF$_2$. UV-Vis absorbance at 500 nm was used to monitor Cur-BF$_2$ elution. A major Cur-BF$_2$ isomer elutes at 2.35 min. A minor isomer is observed (arrow) as a shoulder peak.

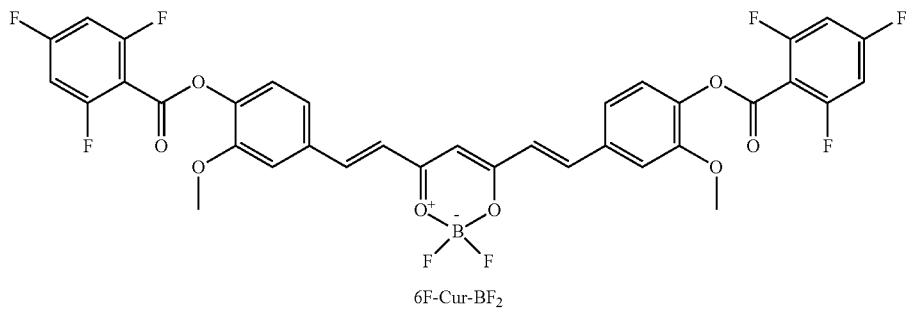

6F-Cur-BF$_2$ (6F-Cur-BF$_2$) Synthesis of 6F-Cur-BF$_2$ for Sentinel node mapping: Cur-BF$_2$ (12.5 mg, 0.03 mmol), 2,4,6-Trifluorobenzoic acid (15.8 mg, 0.09 mmol), HOBt hydrate (12.2 mg, 0.09 mmol), EDC hydrochloride (57.6 mg, 0.3 mmol) and 20 μL pyridine were dissolved in 1 mL DMF (HPLC) in a 1.5 mL Eppendorf tube. The reaction, shielded from light, was left at room temperature overnight. A color change from weak orange-red to bright green is visible under 365 nm UV lamp illumination indicating reaction. The product was isolated by C18 reverse phase, preparative chromatography. $^1$H NMR (500 MHz, d6-DMSO, 21° C., TMS): δ 8.10 (d, J=15.8 Hz, 2H, isomer, trans), 8.02 (d, J=8.4 Hz, 2H, isomer, cis), 7.76 (s, 2H), 7.57 (d, J=8.15 Hz, 2H), 7.48 (t, J=9.25 Hz, 4H), 7.39 (d, J=8.15 Hz, 2H), 7.34 (d, J=15.75 Hz, 2H), 6.68 (s, 1H), 3.90 (s, 6H); $^{13}$C NMR (125 MHz, d6-DMSO, 21° C., TMS): δ 180.62, 164.15, 162.98, 162.91, 162.85, 162.78, 160.93, 160.86, 160.80, 160.73, 158.25, 151.52, 146.67, 141.83, 134.24, 131.66, 123.85, 123.38, 122.58, 114.13, 106.25, 106.22, 102.98, 102.95, 102.77, 102.74, 102.56, 102.53, 56.80; $^{19}$F NMR (470 MHz, d6-DMSO, 21° C., CFCl$_3$): δ -102.030 (t, J=10.25 Hz, 2F), -107.581 (t, J=10 Hz, 4F), -139.407 (2F, A major product (A) and a minor isomer (B) are observed. (A) [$^{10}$B]—BF$_2$: δ -139.445 (30.6%), [$^{11}$B]—BF$_2$: δ -139.508 (69.4%) (Δ 0.063 ppm), (B) [$^{10}$B]—BF$_2$: δ -139.296 (11.1%), [$^{11}$B]—BF$_2$: δ -139.369 (88.9%) (Δ 0.073 ppm)); HRMS (ESI) calc'd for [M]=[C$_{35}$H$_{21}$BF$_8$O$_8$]: 732.1202, found [M]−: 732.1185. UPLC characterization: A 2 min, a 10-90 linear gradient (0.05% TFA) was used to characterize 6F-Cur-BF$_2$. UV-Vis absorbance at 455 nm was used to monitor 6F-Cur-BF$_2$ elution. A major 6F-Cur-BF$_2$ isomer elutes at 3.178 min along with a minor isomer indicated by a red arrow.

Synthesis of Cur-BF$_2$-2Mal: Cur-BF$_2$ (12.5 mg, 0.03 mmol), 3-Maleimidopropionic acid (15.2 mg, 0.09 mmol), HOBt hydrate (12.2 mg, 0.09 mmol), EDC hydrochloride (57.6 mg, 0.3 mmol) and 20 μL pyridine were dissolved in 1 mL DMF (HPLC) in a 1.5 mL Eppendorf tube. The reaction, shielded from light, was left at room temperature overnight. A color change from weak orange-red to bright green visible under 365 nm UV lamp illumination indicates reaction. The product was isolated by C18 reverse phase, preparative chromatography. $^1$H NMR (500 MHz, d6-DMSO, 21° C., TMS): δ 8.06 (d, J=15.7 Hz, 2H, isomer, trans), 7.95 (d, J=8.5 Hz, 2H, isomer, cis), 7.66 (s, 2H), 7.51 (d, J=7.55 Hz, 2H), 7.29 (d, J=15.8 Hz, 2H), 7.22 (d, J=8.2 Hz, 2H), 7.07 (d, J=3.0 Hz, 4H), 6.65 (s, 1H), 3.83 (s, 6H), 3.78 (t, J=7.0 Hz, 4H), 2.91 (t, J=7.0 Hz, 4H); $^{13}$C NMR (125 MHz, d6-DMSO, 21° C., TMS): δ 180.53, 171.27, 171.21, 168.99, 151.65, 146.79, 142.40, 135.17, 133.67, 123.94, 123.29, 123.13, 122.26, 113.78, 102.67, 56.63, 56.60, 33.66, 32.57; $^{19}$F NMR (470 MHz, d6-DMSO, 21° C., CFCl$_3$): A major product (A) and a minor isomer (B) are observed. (A) [$^{10}$B]—BF$_2$: δ -139.550 (30.1%), [$^{11}$B]—BF$_2$: δ -139.614 (69.9%) (Δ 0.063 ppm), (B) [$^{10}$B]—BF$_2$: δ -139.418 (15.4%), [$^{11}$B]—BF$_2$: δ -139.483 (84.6%) (Δ 0.065 ppm). HRMS (ESI) calc'd for [M]=[C$_{35}$H$_{29}$BF$_2$N$_2$O$_{12}$]: 718.1782, found [M]−: 718.1759. UPLC characterization for Cur-BF$_2$-2Mal. A 2 min, a 10-90 linear gradient (0.05% TFA) was used to characterize Cur-BF$_2$-2Mal. UV-Vis absorbance at 455 nm was used to monitor Cur-BF$_2$-2Mal elution. A major Cur-BF$_2$-2Mal isomer elutes at 2.627 min along with a minor isomer.

Example 2: One-Step, Fast, $^{18}$F-$^{19}$F Isotopic Exchange Radiolabeling of Difluorodioxaborinins: Substituent Effect on the Design of Stable, Fluorescent $^{18}$F-Positron Emitting Contrast Agents Abstract: Electron rich β-diketones react with boron trifluoride to give difluoro-2H-1,3,2-dioxaborinin-1-ium-2-

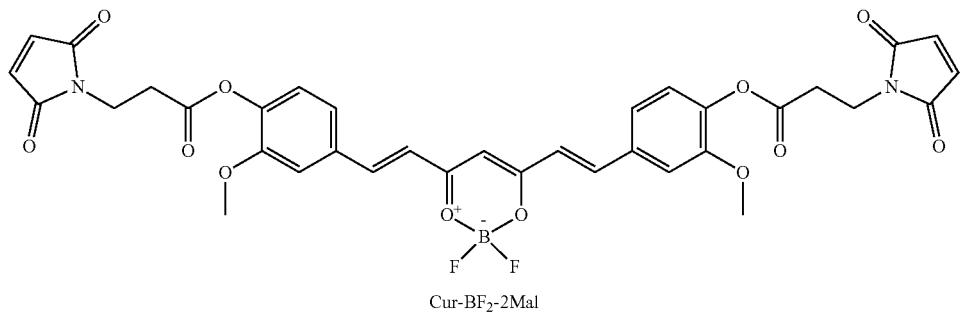

Cur-BF$_2$-2Mal uides with red-shifted optical properties (difluoro-dioxaborinins). This Example shows that these difluoro-dioxaborinins can be generally radiolabeled (>1 Ci/μmol) in a rapid (<10 min), one-step, room temperature, SnCl$_4$-mediated, isotopic fluoride-exchange reaction, in anhydrous, $^{18}$F-fluoride-ion-containing acetonitrile. Not all [$^{18}$F]-difluoro-dioxaborinins are suitable for in vivo 18F-PET imaging. All tested difluoro-dioxaborinins undergo solvolysis in aqueous solution. This rate of solvolysis is highly sensitive to neighboring group chemistry, and that difluoro-dioxaborinins solvolytic stability can be tuned to range between a period of a few hours to hundreds of hours. In studies with a preliminary library of difluorodioxaborinins, three strategies are found to retard solvolysis; 1) reducing water content, 2) increasing dioxaborinin electronegativity through C—H o-bond hyperconjugation, and 3) increasing dioxaborinin electronegativity through extended, electron-rich (position 4, 5, and 6) π-conjugation. Conversely, extended π-conjugations that decrease dioxaborinin electronegativity promote faster solvolysis. To demonstrate translational potential, identified solvolytic retardation strategies are exploited in vivo, where [$^{18}$F]-difluoro-dioxaborinin is used to map sentinel nodes in mice and rabbits specimens by positron emission tomography (PET). This work impacts the design of small-molecule, fluorescent radiotracers, and describes general formulae for transforming β-diketone containing pharmaceuticals and natural products into $^{18}$F-PET contrast agents.

INTRODUCTION: The β-diketone is a common moiety found in many pharmaceuticals and natural products, such as doxorubicin and curcumin. β-Diketones react with boron trifluoride to give difluoro-2H-1,3,2-dioxaborinin-1-ium-2-uides (difluorodioxaborinins, Scheme 1a). In certain cases, this reaction is reversible, and the difluoroboryloxy moiety can be used in p-diketone protective strategies.[1] Dioxaborinins are of interest to biophysical chemists because of tailorable, ultraviolet to near-infrared, red-shifted optical properties that are conveyed onto β-diketone and β-keto esters.[1-3] Molecular agents with near-infrared, fluorescent properties are desired by the medical imaging community, as near-infrared light allows for deeper penetration through tissue.[4-7]

The modification of naturally occurring β-diketones with BF$_2$ represents an, arguably, minimal structural change to the β-diketone. Resulting difluoro-dioxaborinins can be fluorescent[1-3] and have a molecular structure that is different from isobenzofuran (fluorescein) and polymethine cyanines, two popular classes of organic fluorescent probes.

Isotopic, fluoride-exchange radiochemistry is becoming a popular method for preparing positron emitting contrast agents for positron emission tomography (PET) medical imaging.[8-9] Difluoro-dioxaborinins are close structural analogs of the dipyrromethene class of fluorescent dyes (BODIPY), and recent chemistry describes direct dipyrromethene radiolabeling in a one-step, SnCl$_4$-catalyzed isotopic, fluorideexchange reaction.[10-11] This radiochemistry is significant because it is rapid, proceeds at room temperature, and affords stable, fluoride-18 labeled fluorophores at radiochemical yields suitable for medical PET imaging. The close structural similarity between difluoro-dioxaborinins and dipyrromethenes has prompted Applicant to explore the translational potential of SnCl$_4$-catalyzed isotopic-exchange radiolabeling on difluoro-dioxaborinins.

In certain compositions, fluoride-18 radiolabeling of a difluoro-dioxaborinin would add PET utility to a pharmaceutically useful fluorescent probe.[5, 12-13] A general strategy for $^{18}$F-PET labeling β-diketones would allow many β-diketone bearing pharmaceuticals and natural products to be transformed into $^{18}$F-PET contrast. The in vivo PET and fluorescent imaging of bioactive difluoro-dioxaborinins would provide imaging data that may be used to design agents with superior absorption, distribution, metabolism, excretion, and toxicity properties.

Herein, difluoro-dioxaborinins with tailorable fluorescent optical properties spanning from ultraviolent to orange wavelengths are provided. These difluoro-dioxaborinins can be generally radiolabeled (>1 Ci/μmol) in a rapid (<10 min), one-step, room temperature, SnCl$_4$-mediated isotopic fluoride exchange reaction. A detailed study investigates substituent effect on the design of stable, fluorescent $^{18}$F-PET difluoro-dioxaborinins. This work impacts the design of small-molecule, fluorescent radiotracers, and describes general formulae for transforming β-diketone containing pharmaceuticals and natural products into $^{18}$F-PET contrast agents.

RESULTS: Trifluoroborates, dipyrromethenes, and difluorodioxaborinins all bear boron-fluoride bonds. Many trifluoroborates and dipyrromethenes have been thoroughly evaluated for their utility as prosthetic groups in PET imaging.[9,14-15] This experimental precedent is used to gauge the utility of the difluoro-dioxaborinins in PET.

Dipyrromethenes are solvolytically stable; however, current reported compositions are generally large and hydrophobic.[10-11, 16] Alternatively, certain low-molecular weight aryl trifluoroborates undergo very rapid solvolysis (<4 min), 14 where defluoridation results in fluoride ion production and large background in the bone in vivo. To transform aryl/alkyl trifluoroborates into agents that are suitable for PET imaging, aryl/alkyl trifluoroborate solvolysis rates are strategically retarded using electron-poor neighboring groups.[11, 14] Like the aryl/alkyl trifluoroborate, difluorodioxaborinins are expected to undergo a degree of solvolysis, based on prior studies where difluoroboryloxy moieties can be removed from difluoro-dioxaborinin using basic (high pH) strategies.[1] As was demonstrated with the aryl/alkyltrifluoroborate,[11, 14] it is expected that difluorodioxaborinin solvolysis can be retarded by exploiting neighboring group functionality.

In all difluoro-dioxaborinin $^1$H NMR, a significantly deshielded proton at dioxaborinin position 5, equivalent to the enolate proton in parent β-diketone, presents between 6-8 ppm. This downfield shift, combined with published crystal data,[1] suggests that difluoro-dioxaborinins have aromatic character, and that difluoro-dioxaborinins may substitute for aromatic rings in cation-pi, biological interactions. All isolated difluoro-dioxaborinins show two fluoride atoms bound to boron in F NMR and high-resolution mass spectrometry (HRMS).

Cur-BF$_2$-2Mal was synthesized with the intent that it may be readily conjugated to acetonitrile-stable, thiol-bearing peptides, nucleic acids, polymers, and nanoparticles for future direct fluoride-18 radiolabeling.

General radio labeling procedure: [$^{18}$F]-fluoride ion obtained from a cyclotron was concentrated to dryness with 30 psi nitrogen flow, over a 15 min period, without heating, in a 5 mL borosilicate conical vial. A 2% solution of SnCl$_4$ (20 μL, neat) in anhydrous acetonitrile (1 mL) was used to resuspend dry [$^{18}$F]-fluoride-ion. This suspension was immediately added to 0.5 mg of dry, powdered difluorodioxaborinin. In radiosynthesis involving 0.5 mg of difluoro-dioxaborinin and 0.6 mCi of activity, RCYs were measured for Table 1 difluoro-dioxaborinins after 30 min of radiolabeling. Generally, radiochemical yields (RCYs) are >90% as determined by high performance liquid chromatography (HPLC) equipped with UV-vis and radio detector by injecting 10 μL of the crude reaction (DK-1, with the exception of: DK-16: ~88%, 6F-Cur-BF$_2$: ~75%, and Cur-BF$_2$-2Mal: ~80%, see HPLC characterization of difluoro dioxaborinin $^{18}$F-radiolabeling, below). RCYs were corroborated by silica TLC using pure methanol as the mobile phase. Deionized water may be used as the mobile phase for resolving DK-1, DK-2, DK-3, DK-6 and DK-15, but may not be used to resolve more hydrophobic difluoro-dioxaborinins (see HPLC characterization of radiolabeling procedures below). RCYs calculated by TLC were lower, 61%-74% (Table 1). Note that TLC measurements underestimate RCY, as minor quantities of radiolabeled difluoro-dioxaborinin are retained at the baseline and are calculated as [18F]-fluoride ion, which does not move from the baseline (see FIGS. 1A and 1B). Note that HPLC calculations overestimate RCY, as some [18F]-fluoride ion is retained by and not eluted from silica backed columns.

of ~7.4 Ci/gmol (decay uncorrected) was achieved by using 16.4 mCi dry [18F]-fluoride ion and 0.5 nmol DK-1 for radiolabeling (see Specific activity determination with prototype difluoro-dioxaborinin DK-1, below). The recommended specific activity for [18F]-FDG clinical application is ~1 Ci/gmol, and the dose of [18F]-FDG administrated to an adult is 5-15 mCi.[18] A similar specific activity (>1 Ci/μmol, DK-1) was achieved using a relatively safe dose of [18F]-fluoride ion.

[18]F-Autoradiographic TLC characterization of difluoro dioxaborinin radiolabeling for compounds DK-1, DK-2, DK-3, DK-6, DK-13, DK-14, DK-15, DK-16, DK-17 and Cur-BF$_2$: Radiochemical yields (RCYs) determined by silica TLC: Dioxaborinins were incubated with dry [18F]-fluoride ion in acetonitrile containing 2% SnCl$_4$ for 30 min

TABLE 1

| Composition | Abs (nm) | Em (nm) | Extinction Coefficient (cm$^{-1}$M$^{-1}$) | Quantum yield (%, Methanol) | Stokes Shift (nm) | RCY (%) by HPLC | RCY (%) by silica TLC | Stability ($t_{1/2}$, hours) 90% H$_2$O/10% DMSO | Stability ($t_{1/2}$, hours) 10% H$_2$O/90% DMSO | Fold increase in stability (90% → 10% H$_2$O) |
|---|---|---|---|---|---|---|---|---|---|---|
| DK-1 | 279 | 305 | 9,180 | * | 26 | 99 | 61.6 | 2.73 ± 0.02 | 7.63 ± 0.18 | 2.8 |
| DK-2 | 303 | 307 | 12,200 | * | 4 | 97 | 67.0 | 17.1 ± 0.7 | 53.9 ± 1.1 | 3.2 |
| DK-3 | 303 | 306 | 12,000 | * | 3 | 97 | 69.9 | 15.2 ± 0.5 | 53.9 ± 1.5 | 3.5 |
| DK-6 | 301 | 307 | 12,600 | * | 6 | 99 | 68.5 | 5.19 ± 0.15 | 24.6 ± 0.5 | 4.7 |
| DK-13 | 363 | 413 | 38,000 | 11.2 | 50 | 98 | 68.0 | — | 10.7 ± 1.8 | |
| 13 | 343 | 390 | 29,000 | * | 47 | | | | | |
| DK-14 | 325 | 328 | 19,800 | * | 3 | 98 | 67.5 | — | 4.46 ± 0.05 | |
| DK-15 | 303 | 307 | 12,000 | * | 4 | 98 | 66.0 | 6.75 ± 0.19 | 33.7 ± 1.1 | 5.0 |
| DK-16 | 400 | 439 | 62,000 | 67.3 | 39 | 88 | 67.2 | — | 118 ± 12 | |
| 16 | 358 | 388 | 44,400 | * | 30 | | | | | |
| DK-17 | 408 | 438 | 63,600 | 65.8 | 30 | 92 | 73.8 | — | 122 ± 3 | |
| 17 | 363 | 391 | 33,800 | * | 28 | | | | | |
| Cur-BF$_2$ | 500 | 571 | 73,000 | 1.3 | 71 | 93 | 64.1 | — | 391 ± 4 | |
| Curcumin | 434 | 535 | 56,500 | 2.4 | 101 | | | | | |
| 6F-Cur-BF$_2$ | 430 | 512 | 50,800 | 3.0 | 82 | 75 | 61.6 | — | 11.9 ± 0.4 | |
| Cur-BF$_2$-2Mal | 434 | 509 | 54,000 | 3.1 | 75 | 80 | 64.4 | — | 16.0 ± 0.2 | |
| [18F]-Fluoride ion | | | | | | | | 1.8 | 1.8 | |

Figure 1B:
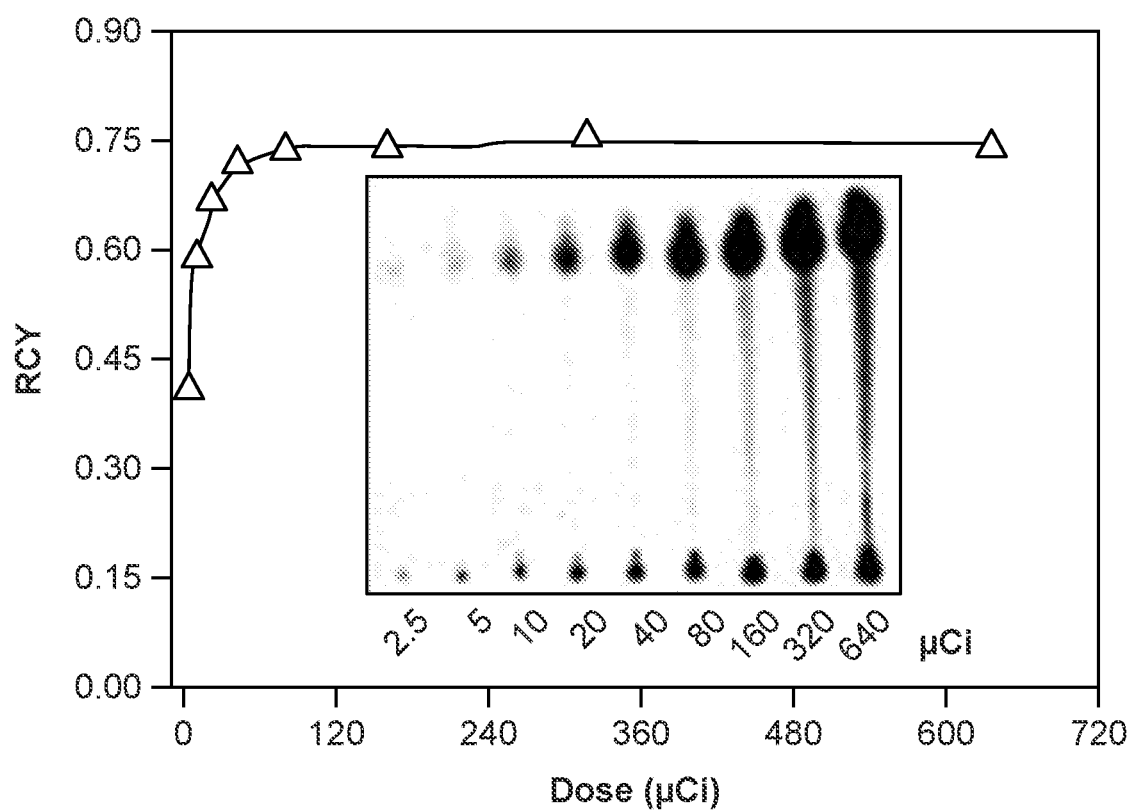

Results: Full solubility was observed. Difluorodioxaborinin isotopic exchange proceeds rapidly, upon mixing (FIG. 1A), at room temperature, and majority conversion is observed at or before 10 min (FIG. 1A). The radiolabeling of DK-1, a prototype difluoro-dioxaborinin, proceeds quickly at room temperature with >50% radiochemical yield (RCY) observed after 5 min (FIG. 1A). Contaminating carrier fluoride ion from acetonitrile, tin chloride, the isotopic exchange reaction, or untreated, cyclotron-bombarded water, did not greatly affect radiolabeling. RCYs that are greater than >50% may be achieved with >5.0 μCi of activity (FIG. 1B).

Figure 1C:
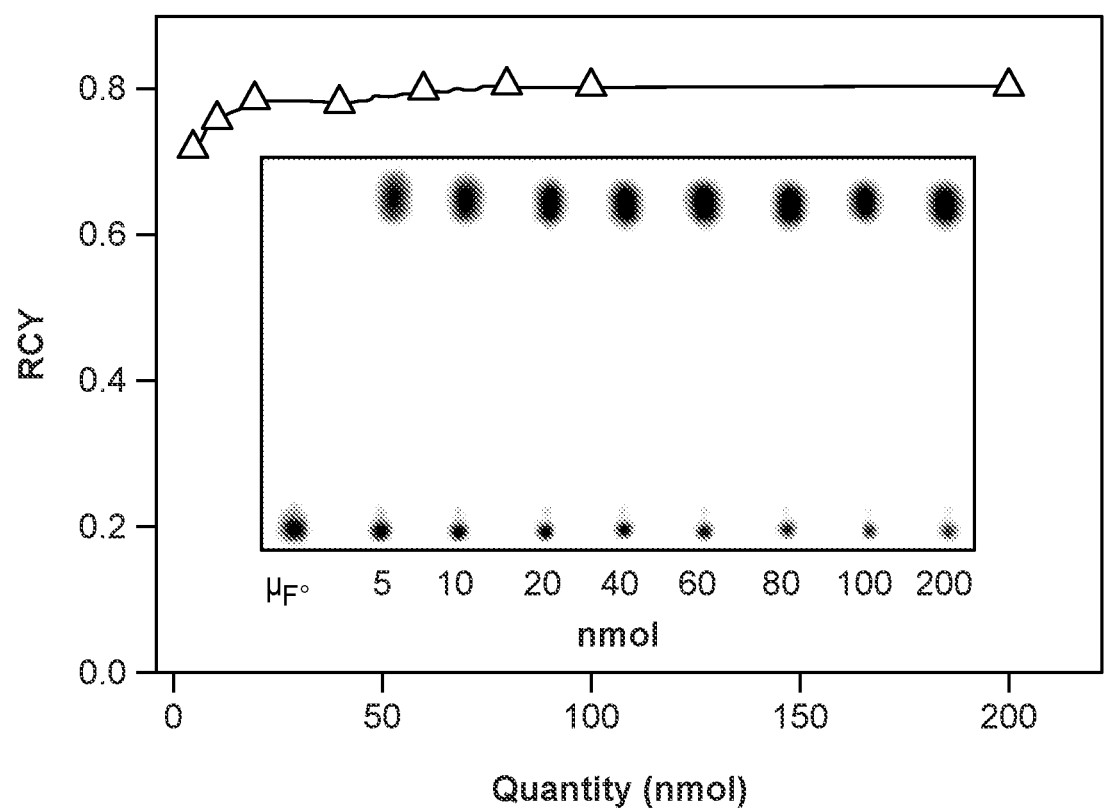

Low specific activity radiolabeling of DK-1: Specific activity was determined in radiolabeling of DK-1 (FIG. 1C). Different quantities of DK-1, were suspended with 0.32 mCi of dry [18F]-fluoride-ion in SnCl$_4$-containing anhydrous acetonitrile. After 30 min, all samples were plated on thin layer chromatography (TLC) and RCYs were determined. The maximum specific activity radiolabeled was 37.8 mCi/gmol (decay uncorrected, FIG. 1C, See [18]F-Autoradiographic TLC characterization below).

High specific activity radiolabeling of DK-1: Encouraged by near-quantitative RCYs produced with low activities of dry [18F]-fluoride ion, DK-1 was labeled with higher activities of dry [18F]-fluoride ion to achieve a higher specific activity. A specific activity of ~1.4 Ci/μmol (decay uncorrected) was achieved when 16.4 mCi of dry [18F]-fluoride ion was used to radiolabel 5 nmol DK-1. A specific activity for radiolabeling (See Scheme 1b above). At defined time points, 0.2 μL aliquots of the crude reaction mixture was dropped on silica TLC. Methanol was used as the mobile phase (10-15 min). The silica plate was allowed to dry naturally in the air before a phosphorimaging screen was used to expose TLC plates for 5 min. Exposed film was scanned by phosphorimager. The figure was further analyzed with ImageJ software: The free [18F]-fluoride ion stays at the baseline (drop point) and the [18F]-fluoride ion labeled on the chemical runs to the frontier. A shape enclosing the point on the solvent front, baseline, and a blank control (background) were analyzed with ImageJ for respective mean intensities.

TLC radiolabeling of 6F-Cur-BF$_2$ and Cur-BF$_2$-2Mal with methanol as the mobile phase: A phosphorimaging screen was used to expose TLC plates for 5 min. Exposed film was scanned by phosphorimager.

TLC radiolabeling of DK-1, DK-2, DK-3, DK-6, DK-13, DK-14, DK-15, DK-16, DK-17 and Cur-BF$_2$ with water as the mobile phase: Only water-soluble dioxaborinins move with the water solvent front. A phosphorimaging screen was used to expose TLC plates for 5 min. Exposed film was scanned by phosphorimager.

Specific activity determination with prototype difluoro-dioxaborinin DK-1: TLC radiolabeling of 5 or 0.5 nmol DK-1 after 30 min incubation with 16.4 mCi dry [18F]-fluoride ion in acetonitrile containing 2% SnCl$_4$. 0.2 μL [18F]-fluoride ion in acetonitrile containing 2% SnCl$_4$ and 0.2 µL radiolabeling solution was dropped on the silica TLC and methanol was used as the mobile phase. A phosphorimaging screen was used to expose TLC plates for 2 min. Exposed film was scanned by phosphorimager. The figure was further analyzed with ImageJ software and obtained a specific activity of ~1.4 Ci/µmol for 5 nmol DK-1 and 7.4 Ci/µmol for 0.5 nmol DK-1 (decay uncorrected).

Fluorescent analysis of radiolabeled difluoro dioxaborinins: The TLC plate run as discussed above for DK-1, DK-2, DK-3, DK-6, DK-13, DK-14, DK-15, DK-16, DK-17, and Cur-BF$_2$ with methanol as the mobile phase was irradiated with 365 nm light irradiation to show that some difluoro dioxaborinins are fluorescent.

HPLC characterization of difluoro dioxaborinin $^{18}$F radiolabeling: General radiolabeling: Fresh SnCl$_4$ catalyst was prepared by dissolving 20 µL SnCl$_4$ (Sigma, 99.995% trace metals basis, #217913) in 1 mL dry acetonitrile (HPLC, Sigma, product of USA). 1 mL of this solution was added to a dry agilent v-vial containing fluoride-18, which was concentrated to dryness with nitrogen flow in a 1 mL borosilicate Agilent screw top micro sampling vial (Agilent, #5184-3550). The vial was mixed with a pipette. 0.1 mL (10%) of this solution containing SnCl$_4$ and fluoride-18 was added to dry Difluoro dioxaborinin powder (~0.5 mg of each sample). Reactions are generally complete after 5 min; however, in the reaction traces below, reactions may have been left for up to 30 min at room temperature (~21° C.) before they are run on HPLC. The samples were submitted on an aging Varian HPLC equipped with a radioactivity detector to confirm reaction by injecting ~10 µL of the solution containing 2% SnCl$_4$, [$^{18}$F]-fluoride ion and the radiolabeled Difluoro dioxaborinin boron chemicals. Analytical HPLC was carried out with a Hamilton PRP—C18 analytical column (5 m, 4.6×50 mm column, #79675, 2 mL/min). UV-Vis absorbance and a radioactivity detector were used to monitor difluoro dioxaborinin elution. In all cases, absorbance and radioactive traces correlate.

Procedures for Analytical HPLC of Radiolabeling Reaction by Compound

Figure 1D:
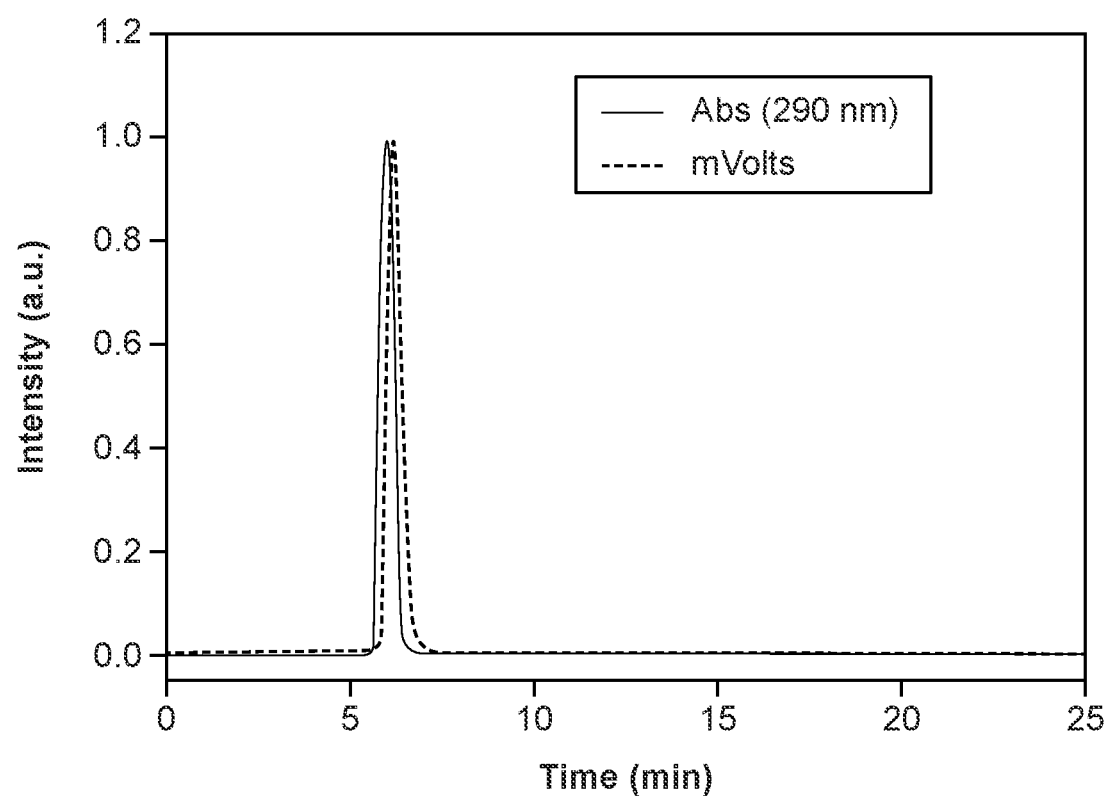

Analytical HPLC was performed on reactions of DK-1. A 20 min, 10-60 linear gradient (90% solvent A (0.05% TFA in H$_2$O) and 10% solvent B (0.05% TFA in acetonitrile) to 40% solvent A (0.05% TFA in H$_2$O) and 60% solvent B (0.05% TFA in acetonitrile)) was used to characterize DK-1 labeling. UV-Vis absorbance at 290 nm was used to monitor DK-1 elution. DK-1 elutes at 6.0766 min, and correlates with the radioactivity trace (FIG. 1D).

Analytical HPLC DK-2: A 20 min, 10-70 linear gradient (90% solvent A (0.05% TFA in H$_2$O) and 10% solvent B (0.05% TFA in acetonitrile) to 30% solvent A (0.05% TFA in H$_2$O) and 70% solvent B (0.05% TFA in acetonitrile)) was used to characterize DK-2 labeling. UV-Vis absorbance at 300 nm was used to monitor DK-2 elution. DK-2 elutes at 5.8843 min, and correlates with the radioactivity trace. A DK-2 aggregate or injection artifact bearing both 300 nm absorbance and activity is visible at 12.2 min.

Analytical HPLC DK-3: A 20 min, 10-70 linear gradient was used to characterize DK-3 radiolabeling. UV-Vis absorbance at 300 nm was used to monitor DK-3 elution. DK-3 elutes at 8.8841 min, and correlates with the radioactivity trace. A DK-3 aggregate or injection artifact bearing both 300 nm absorbance and activity is visible at 15 min.

Analytical HPLC DK-6: A 20 min, 10-90 linear gradient was used to characterize DK-6 radiolabeling. UV-Vis absorbance at 290 nm was used to monitor DK-6 elution. DK-6 elutes at 10.8255 min and correlates with the radioactivity trace.

Analytical HPLC DK-13: A 20 min, 10-90 linear gradient was used to characterize DK-13 radiolabeling. UV-Vis absorbance at 360 nm was used to monitor DK-13 elution. DK-13 elutes at 13.6427 min and correlates with the radioactivity trace. A DK-13 aggregate or injection artifact bearing both 300 nm absorbance and activity is visible at 20 min.

Analytical HPLC DK-14: A 20 min, a 10-90 linear gradient was used to characterize DK-14 radiolabeling. UV-Vis absorbance at 310 nm was used to monitor DK-14 elution. DK-14 elutes at 11.5559 min and correlates with the radioactivity trace.

Analytical HPLC DK-15: A 20 min, 10-90 linear gradient was used to characterize DK-15 radiolabeling. UV-Vis absorbance at 300 nm was used to monitor DK-15 elution. DK-15 elutes at 8.5300 min and correlates with the radioactivity trace. A DK-15 aggregate or injection artifact bearing both 300 nm absorbance and activity is visible at 13.5 min.

Analytical HPLC DK-16: A 20 min, 10-90 linear gradient was used to characterize DK-16 radiolabeling. UV-Vis absorbance at 400 nm was used to monitor DK-16 elution. DK-16 elutes at 17.0375 min, and correlates with the radioactivity trace. A DK-16 aggregate or injection artifact bearing both 400 nm absorbance and activity is visible at 22 min. Unreacted, contaminating fluoride-18 ion is visible at 1 min in the radiotrace.

Analytical HPLC DK-17: A 20 min, a 10-90 linear gradient was used to characterize DK-17 radiolabeling. UV-Vis absorbance at 410 nm was used to monitor DK-17 elution. DK-17 elutes at 14.2166 min, and correlates with the radioactivity trace. A DK-17 aggregate or injection artifact bearing both 410 nm absorbance and activity is visible at 19.5 min. Unreacted, contaminating fluoride-18 ion is visible at 1 min in the radiotrace.

Analytical HPLC Cur-BF$_2$: A 20 min, a 10-90 linear gradient was used to characterize Cur-BF$_2$ radiolabeling. UV-Vis absorbance at 500 nm was used to monitor Cur-BF$_2$ elution. Cur-BF$_2$ elutes at 12.5986 and correlates with the radioactivity trace. Unreacted, contaminating fluoride-18 ion is visible at 1 min in the radiotrace.

Analytical HPLC 6F-Cur-BF$_2$: A 10 min, 30-100 linear gradient was used to characterize 6F-Cur-BF$_2$ radiolabeling. UV-Vis absorbance at 420 nm was used to monitor 6F-Cur-BF$_2$ elution. 6F-Cur-BF$_2$ elutes at 10.7511 min and correlates with the radioactivity trace. Due to the presence of isomer confirmed by the UPLC at 420 nm wavelength, another peak is visible at 12.5 min. Unreacted, contaminating fluoride-18 ion is visible at 1 min in the radiotrace. Fluoride-18 ion may be removed through precipitation by adding water to the reaction solution.

Analytical HPLC Cur-BF$_2$-2Mal: A 10 min, 30-100 linear gradient was used to characterize Cur-BF$_2$-2Mal radiolabeling. UV-Vis absorbance at 420 nm was used to monitor Cur-BF$_2$-2Mal elution. Cur-BF$_2$-2Mal elutes at 7.1820 min and correlates with the radioactivity trace. Due to the presence of isomer confirmed by the UPLC at 420 nm wavelength, another peak is visible at 9.0 min. Unreacted, contaminating fluoride-18 ion is visible at 1 min in the radiotrace.

Example 3: Difluoro-Dioxaborinin Solvolytic Stability Determination

General procedure: A solution containing 2% SnCl$_4$, acetonitrile and trace [$^{18}$F]-fluoride ion was used to dissolve solid, powdered difluoro-dioxaborinin. 30 min later, 45 µL of this acetonitrile mixture was mixed with 5 µL of 1×PBS (pH 7.4) to form solutions containing 10% water. 0.2 μL aliquots of this solution were transferred onto silica thin layer chromatography (Silica TLC) plates at 0h, 1h, 2 h, 3h, 4 h, 5 h and 6 h. After the final time point, dry Silica TLC were run with methanol and exposed to phosphorimaging film. The exposed films were scanned with a Perkin Elmer Storage Phosphor System and analyzed with ImageJ software to quantify the percentages of fluoride-18 in the radiolabeled chemicals.

Discussion: [$^{18}$F]-difluoro-dioxaborinins should have a solvolytic stability that is much greater than the nuclear stability of fluoride-18 ($t_{1/2}$=1.8 hours) to be more useful as clinical $^{18}$F-PET contrast. Radioactive TLC and 1I/$^{19}$F NMR studies were used to determine the solvolytic stability of difluoro-dioxaborinins. Estimations of difluoro-dioxaborinin solvolysis by $^{19}$F-TLC measurement was less accurate (i.e. coefficient of determination are poor) vs. $^{19}$F NMR analyses for two reasons: 1) $^{18}$F decays rapidly, and therefore TLC phosphorimaging is generally not useful for kinetic measurements that are >24 hours; and 2) $^{19}$F NMR indicates that one of two difluoro-dioxaborinin solvolysis products carries $^{18}$F and does not resolve from parent [$^{18}$F]-DK-1 by TLC. For these two reasons, $^{19}$F NMR is the preferred technique for measuring difluoro-dioxaborinin solvolysis. $^{18}$F TLC data for difluoro-dioxaborinins demonstrated stability (also supporting clinical utility) over a 6 hour period, a typical time range for patient $^{18}$F-PET contrast injection and scanning. All difluoro-dioxaborinins tested are solvolytically more stable than fluoride-18 nuclear decay (i.e. $t_{1/2}$ difluoro-dioxaborinin solvolysis >$t_{1/2}$ decay of atomic $^{18}$F >1.8 hours).

Figure 2A:
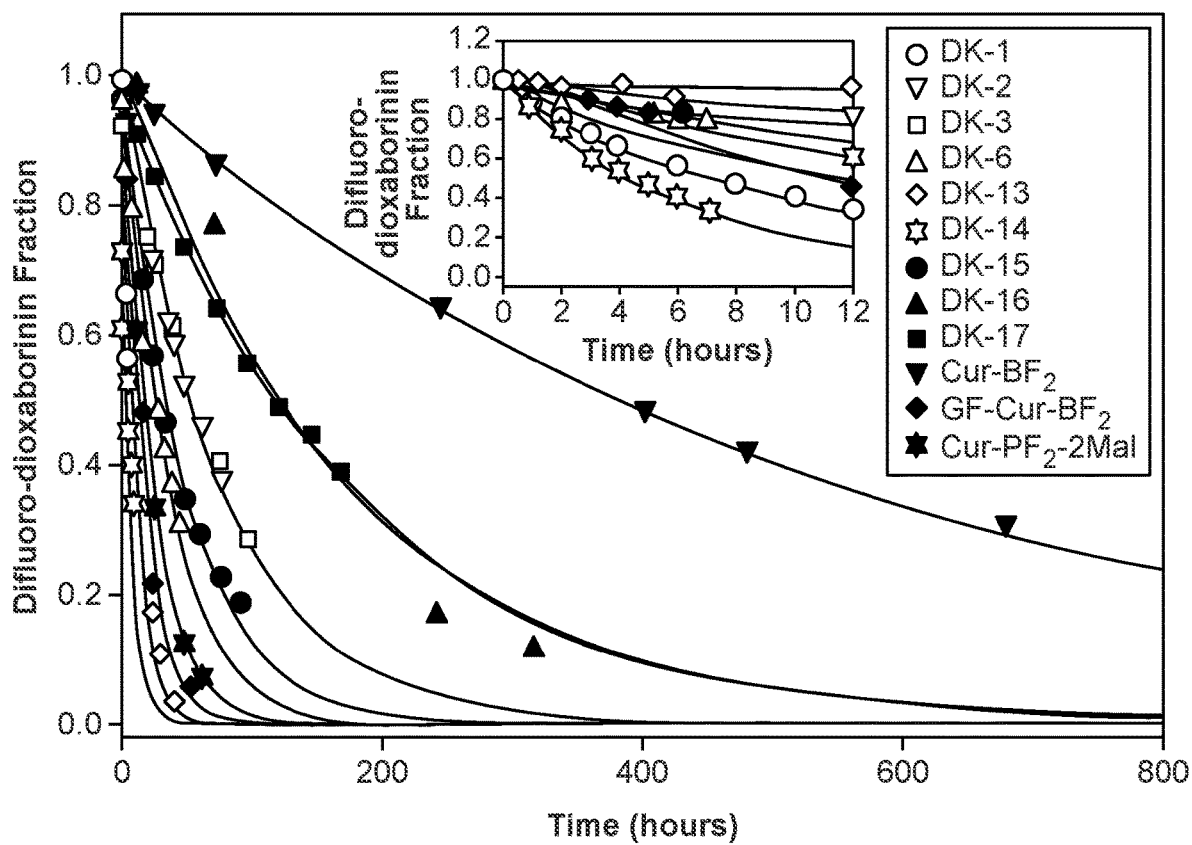
FIG. 2A provides a plot of $^{19}$F NMR solvolytic data for exemplary embodiments of difluoro-dioxaborinin compounds of the present technology (provided in Table 1 herein), with first order decay fits, performed in 10% water/90% DMSO.
Figure 2B:
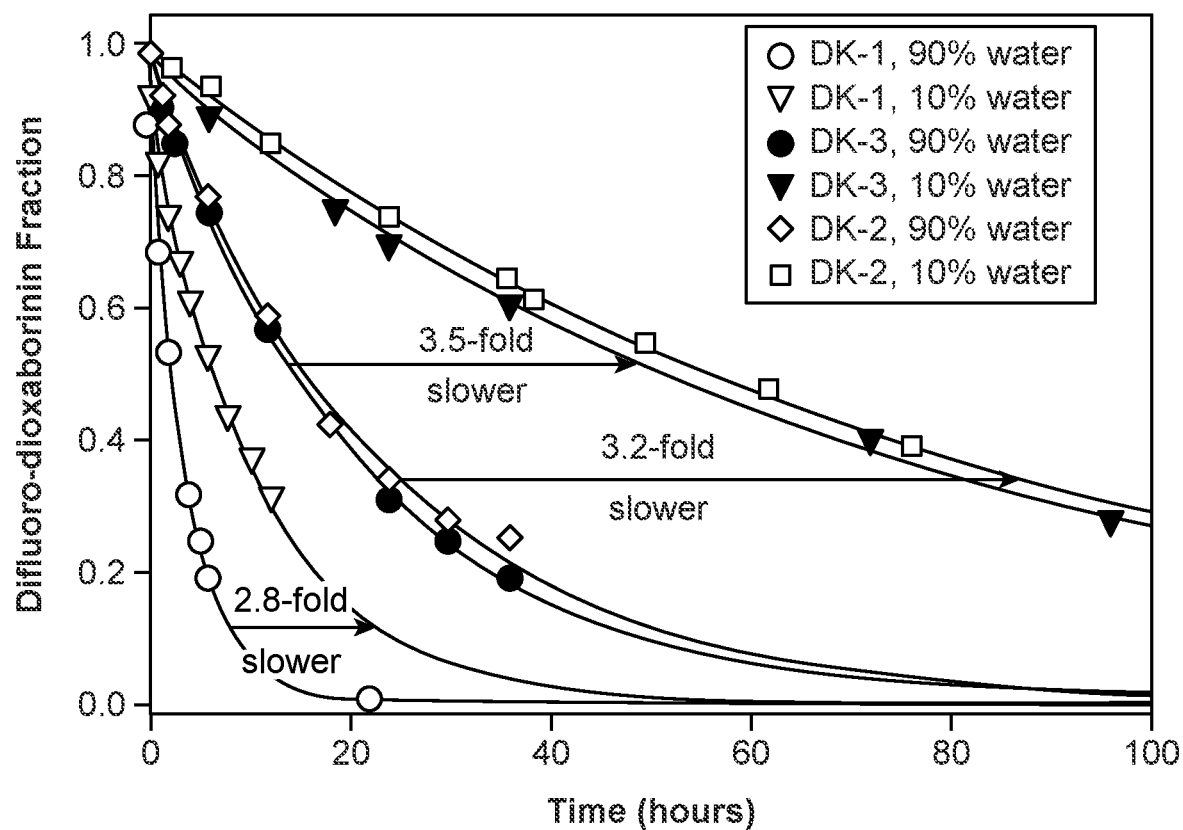
FIG. 2B provides a plot of $^{19}$F NMR solvolytic data of compounds that are soluble in both 90% water/10% DMSO (50 M H$_2$O) and 10% water/90% DMSO (5.55 M H$_2$O). Reducing the molarity of water 10-fold generally retards difluoro-dioxaborinin solvolysis 3-5 fold. Difluoro-dioxaborinin solvolysis is not observed in pure DMSO solution.

Some difluoro-dioxaborinins are insoluble in water; therefore, solvolytic studies on these compounds were determined in 10% $H_2O$/90% DMSO (5.55 M $H_2O$, deionized). To relate the effect of water concentration to solvolysis, solvolytic studies on all water-soluble difluoro-dioxaborinins (DK-1, DK-2, DK-3, DK-6 and DK-15) were performed twice: once in 10% $H_2O$/90% DMSO (5.55 M $H_2O$) (FIG. 2A), and again in 90% $H_2O$/10% DMSO (50 M $H_2O$) (FIG. 2B). Studies performed in 50 M $H_2O$ reflect physiologically appropriate conditions, and allow comparison to literature aryl/alkyl trifluoroborate and dipyrromethene solvolytic stability measurements.[11, 14] Characterization in solutions with reduced water content, 5.55 M $H_2O$, allows comparison of solvolytic rate constants to those of less-soluble difluoro-dioxaborinins. Difluorodioxaborinins solvolysis is not observed in pure (100%) DMSO.

The coefficient of determination ($R^2$) in all $^{19}$F NMR solvolysis data closely follows single, 2 parameter exponential decay regression (f=a*exp(-k*x), R2 >0.99 in 88% of experiments). This close correlation suggests that aqueous [$^{18}$F]-difluoro-dioxaborinin solvolysis is irreversible, and that solvolysis is dependent on a single, rate-determining, pseudo first-order reaction.

Figure 8A:
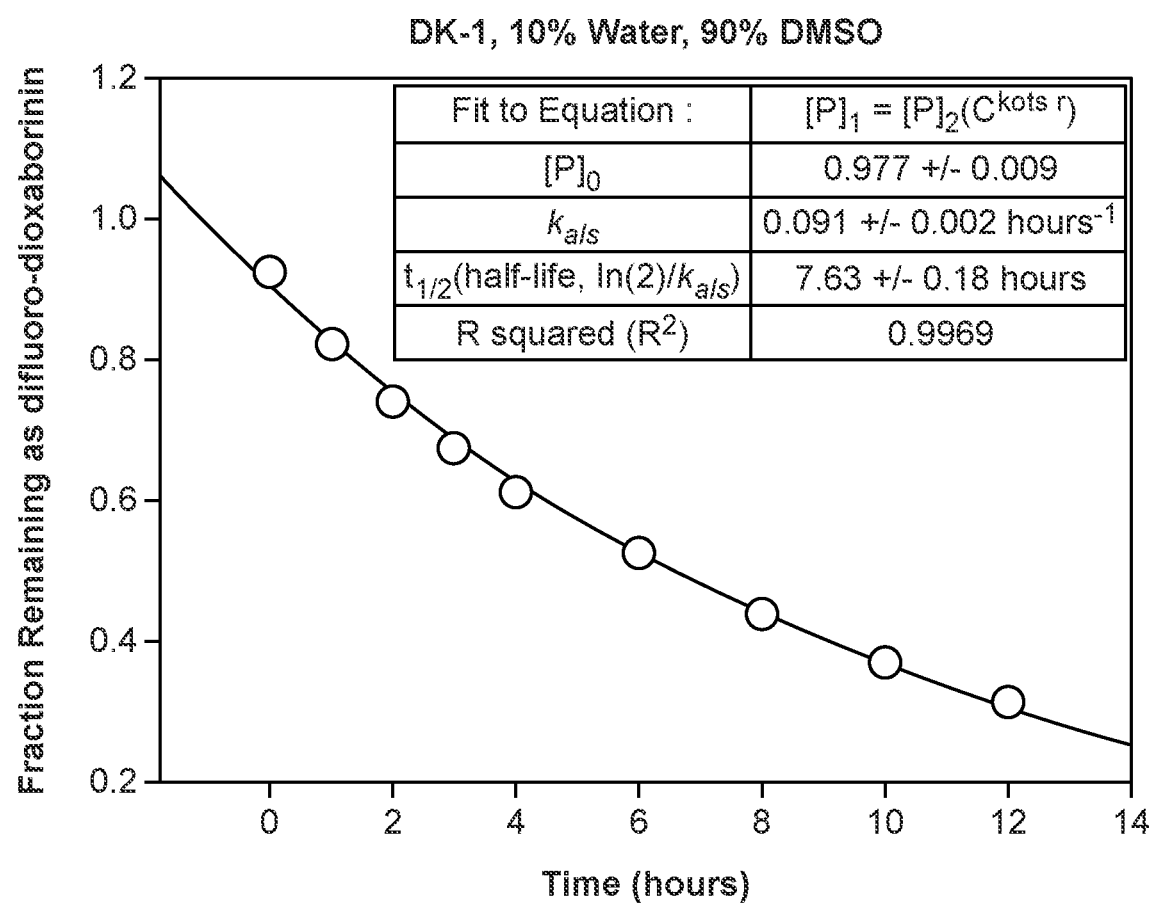
FIGS. 8A-Q provide first order exponential decay fits with rate constant $k_{obs}$ for compounds of the present disclosure in water/DMSO: DK-1 (10% water, FIG. 8A; 90% water FIG. 8B), DK-2 (10% water, FIG. 8C; 90% water, FIG. 8D), DK-3 (10% water, FIG. 8E; 90% water, FIG. 8F), DK-6 (10% water, FIG. 8G; 90% water, FIG. 8H), DK-13 (10% water, FIG. 8I), DK-14 (10% water, FIG. 8J), DK-15 (10% water, FIG. 8K; 90% water, FIG. 8L), DK-16 (10% water, FIG. 8M), DK-17 (10% water, FIG. 8N), Cur-BF$_2$ (10% water, FIG. 8O), 6F-Cur-BF$_2$ (10% water, FIG. 8P), and Cur-BF$_2$-2Mal (10% water, FIG. 8Q).
Figure 8B:
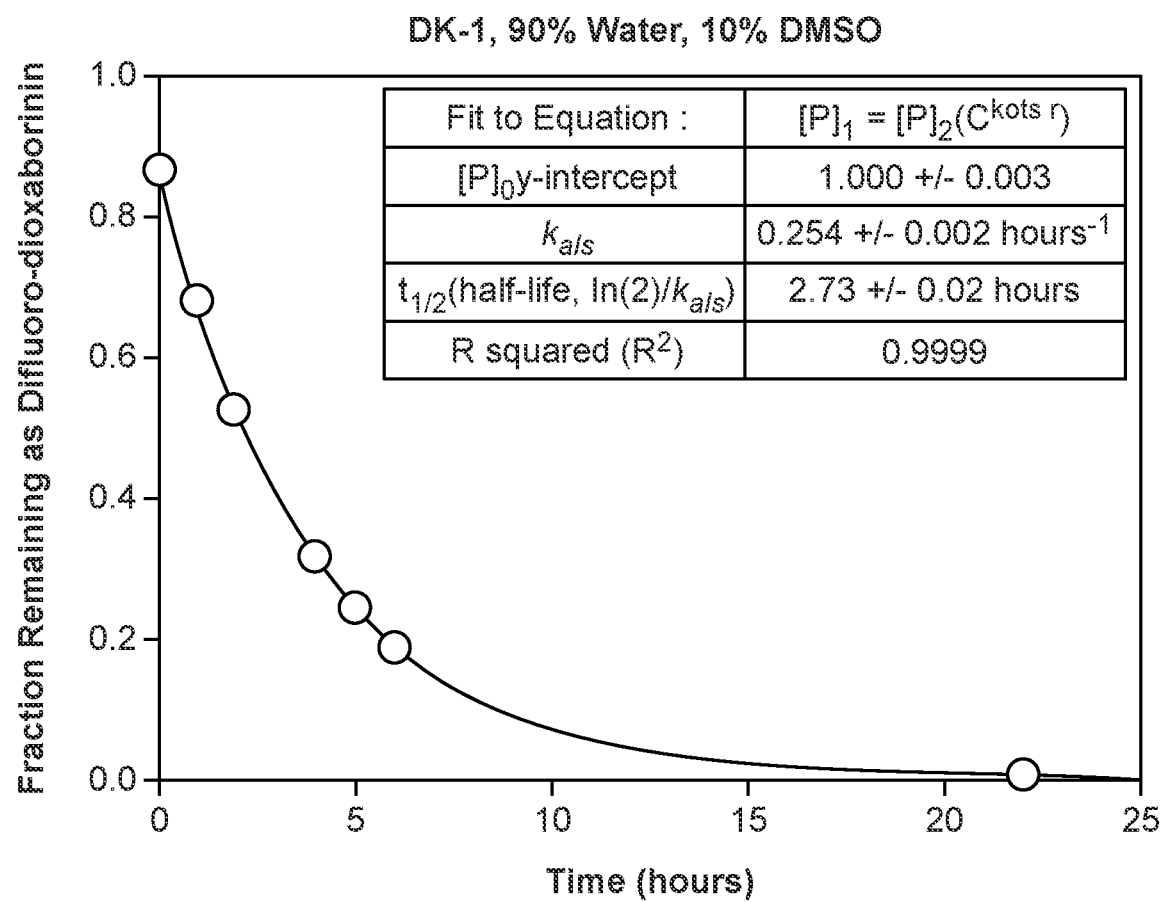
Figure 8C:
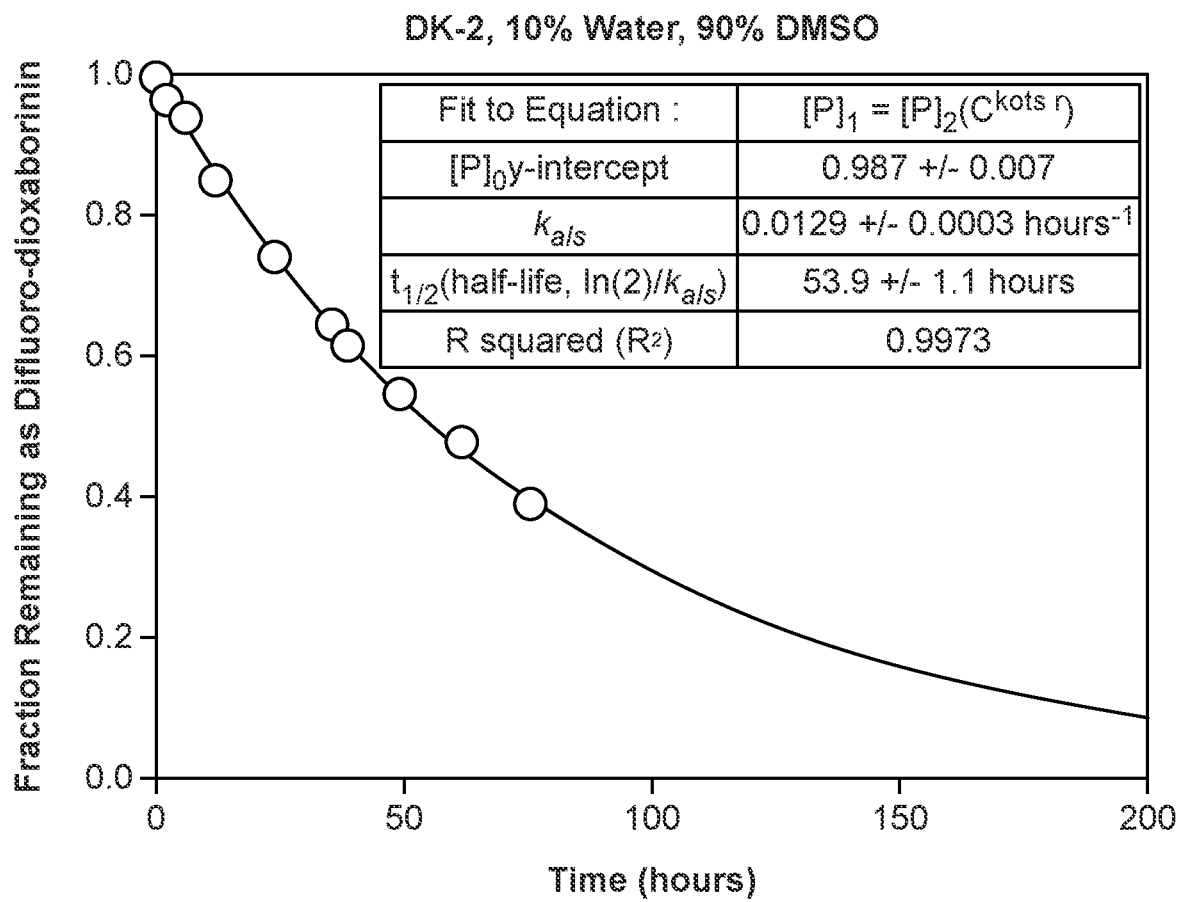
Figure 8D:
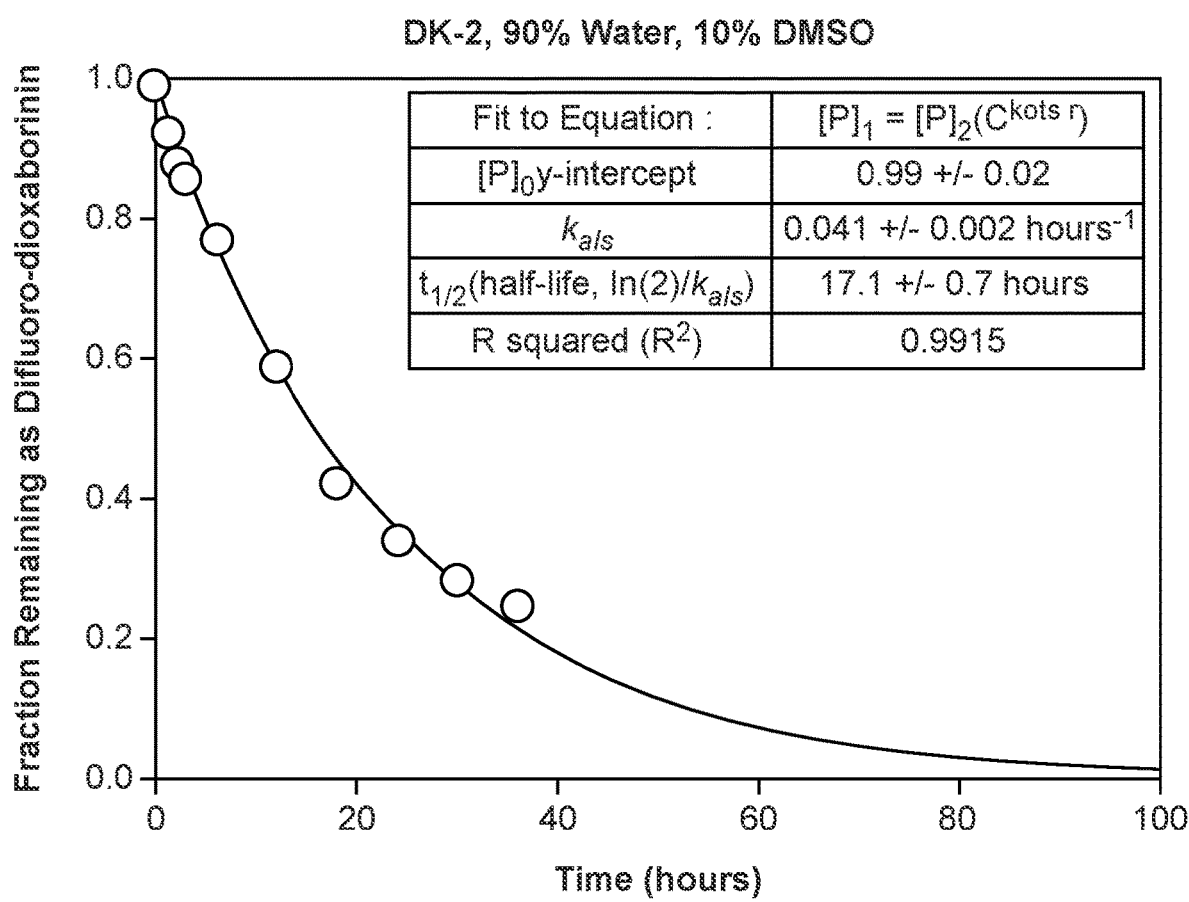
Figure 8E:
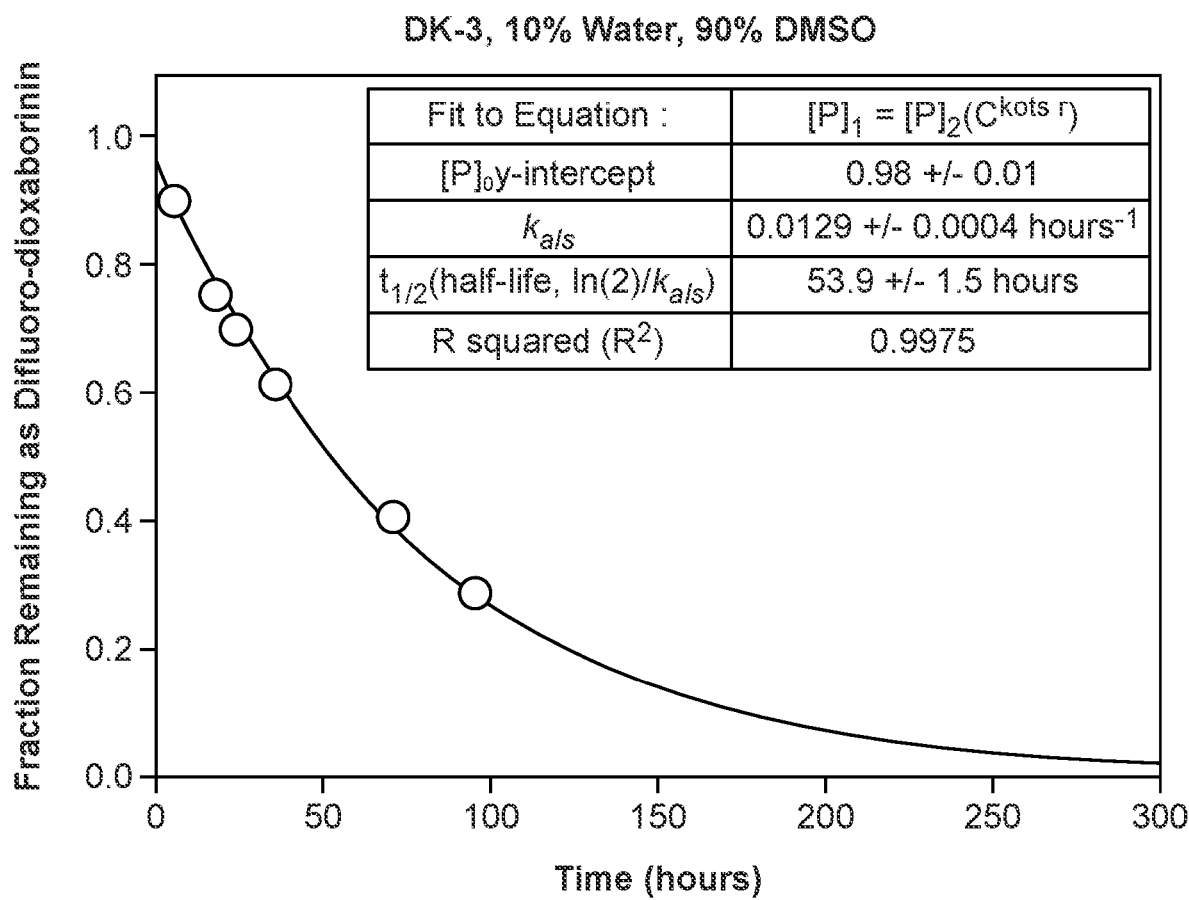
Figure 8F:
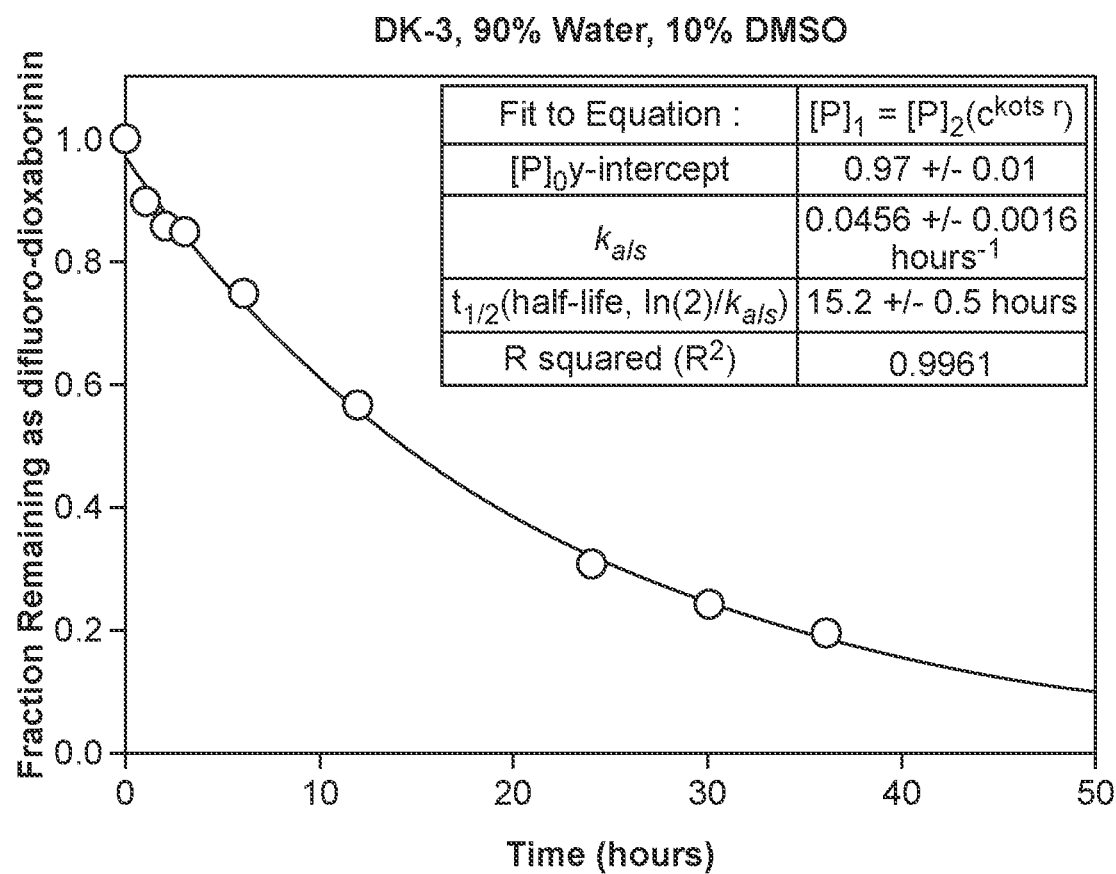
Figure 8G:
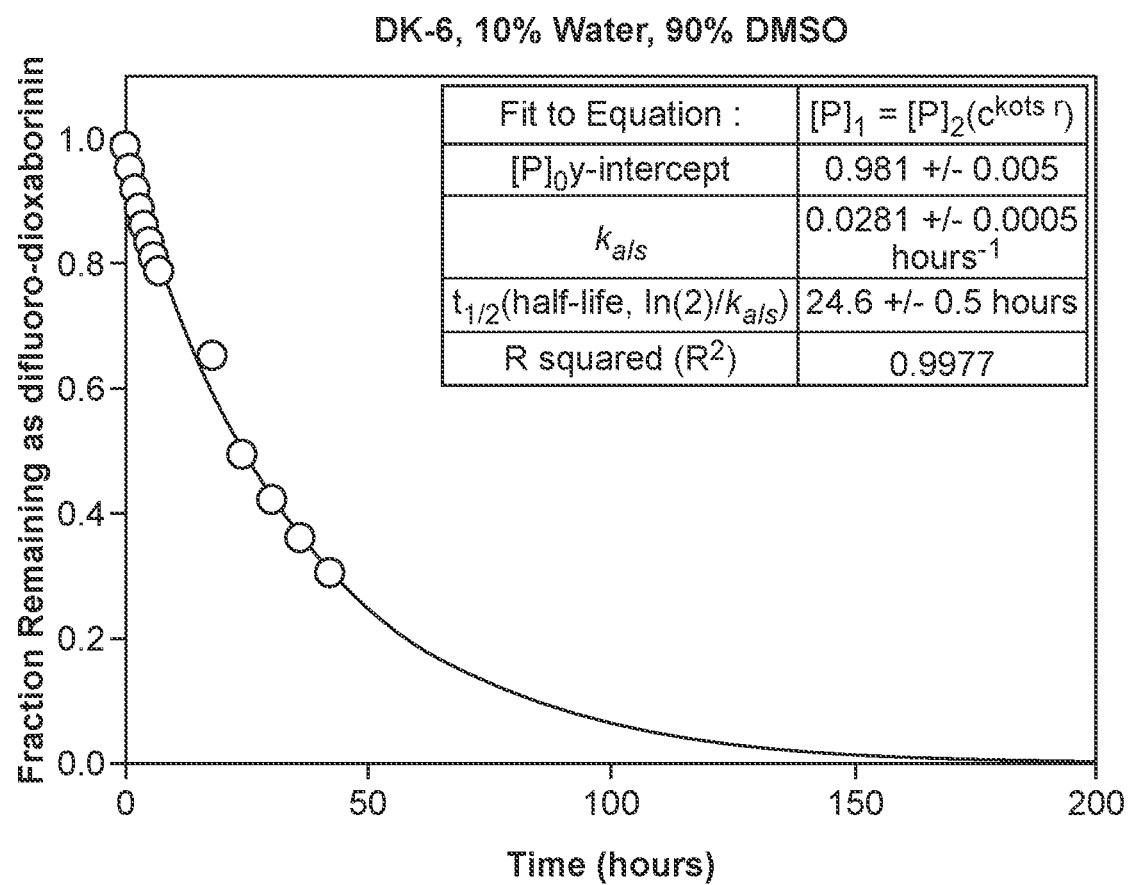
Figure 8H:
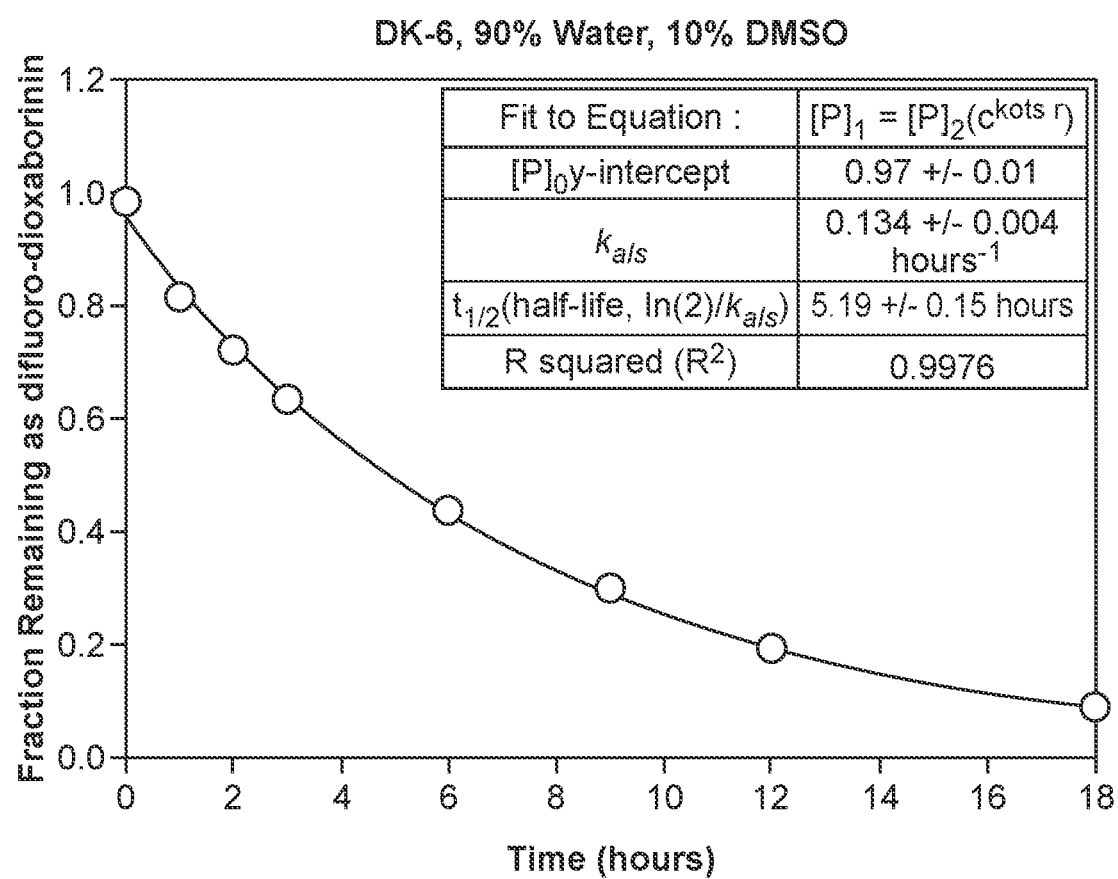
Figure 8I:
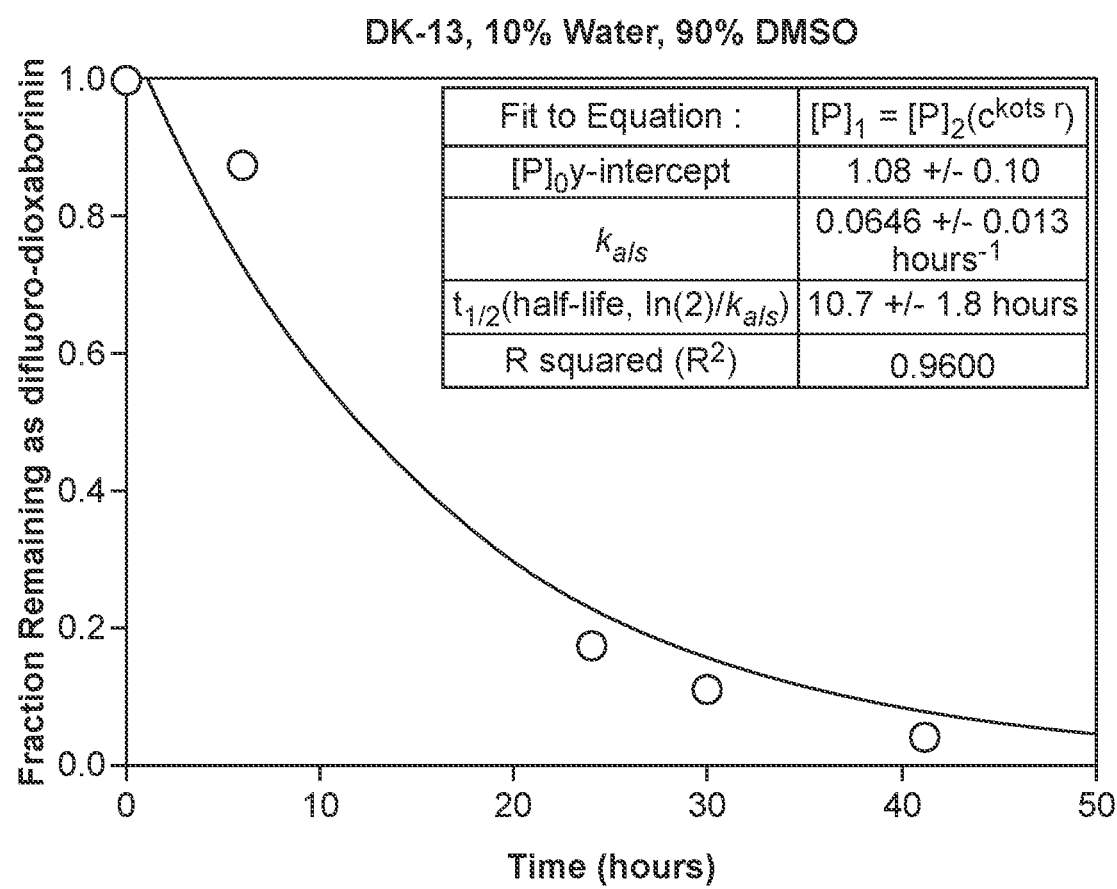
Figure 8J:
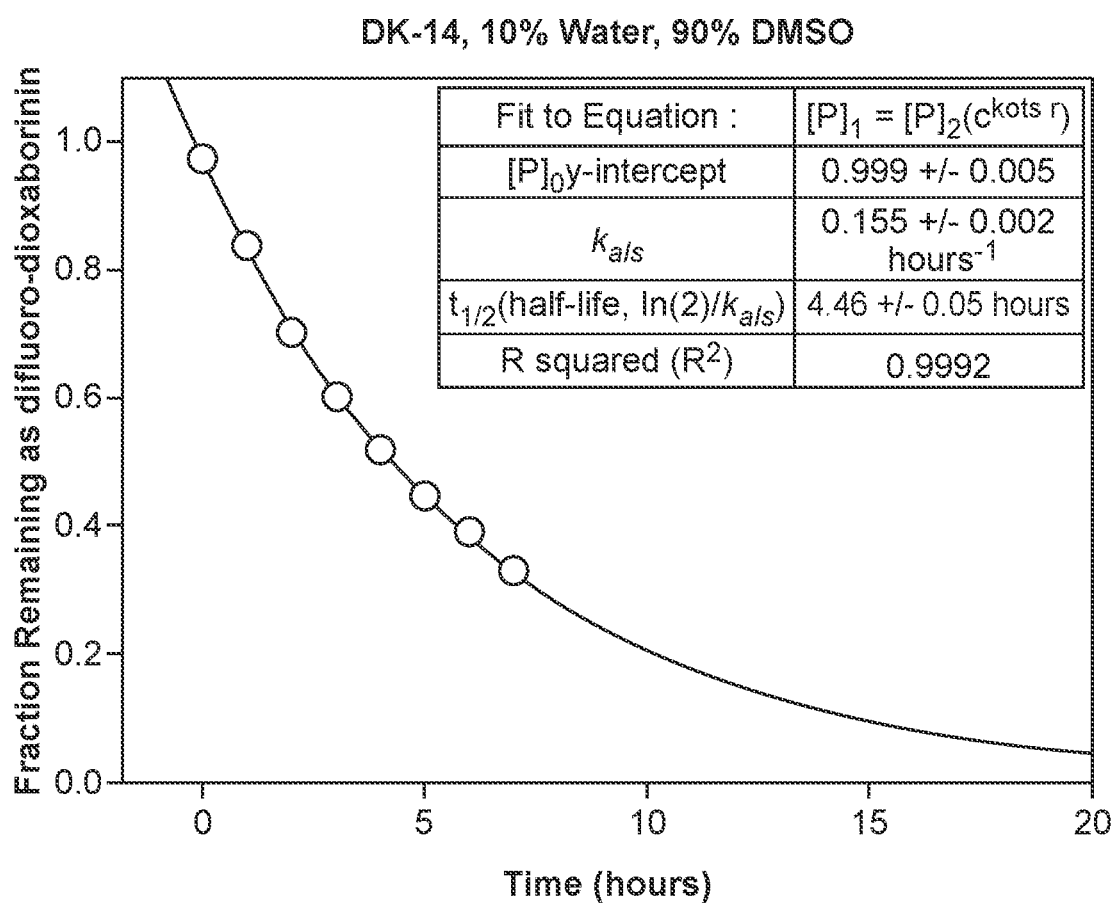
Figure 8K:
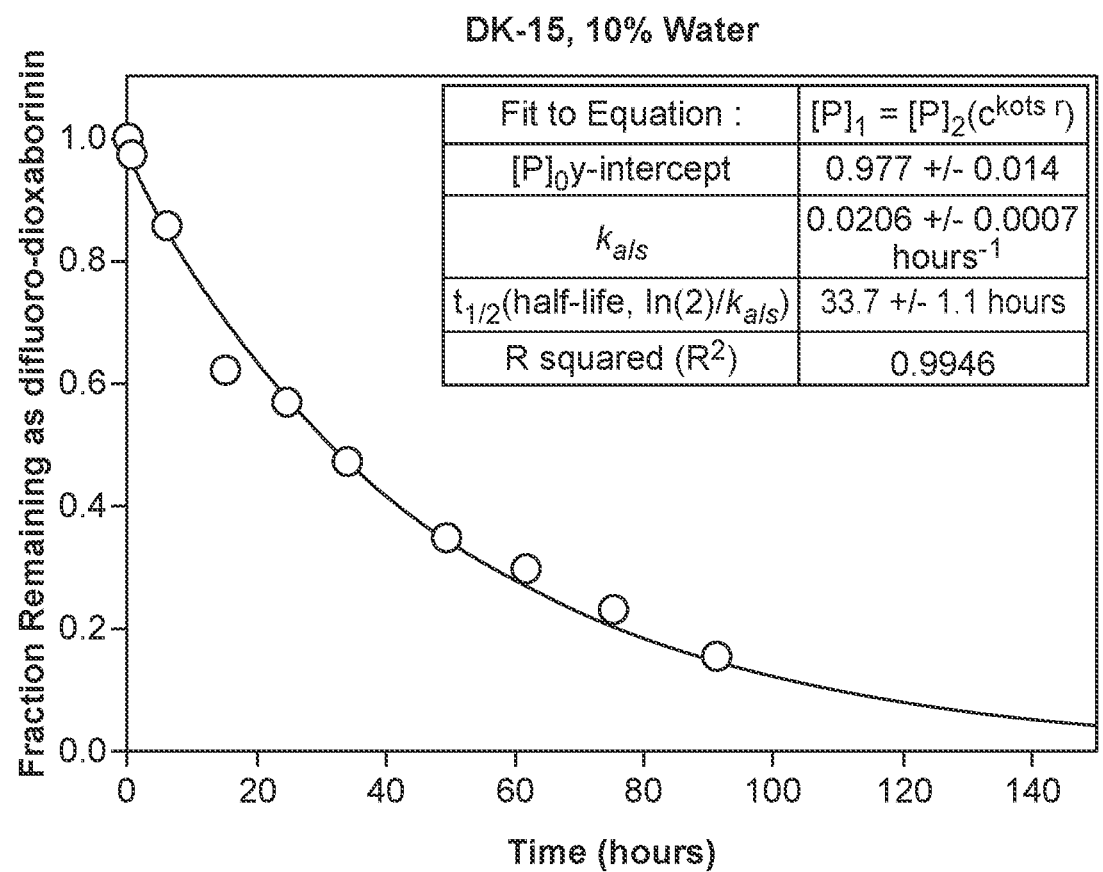
Figure 8L:
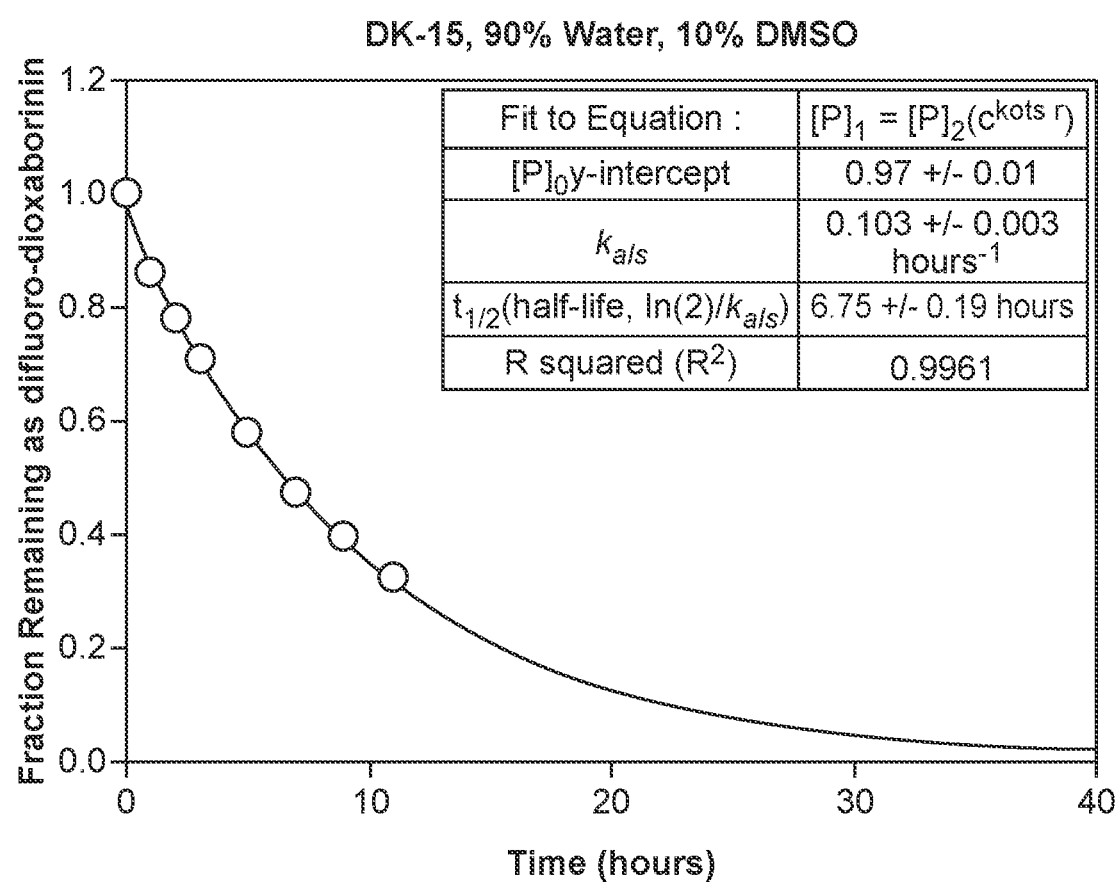
Figure 8M:
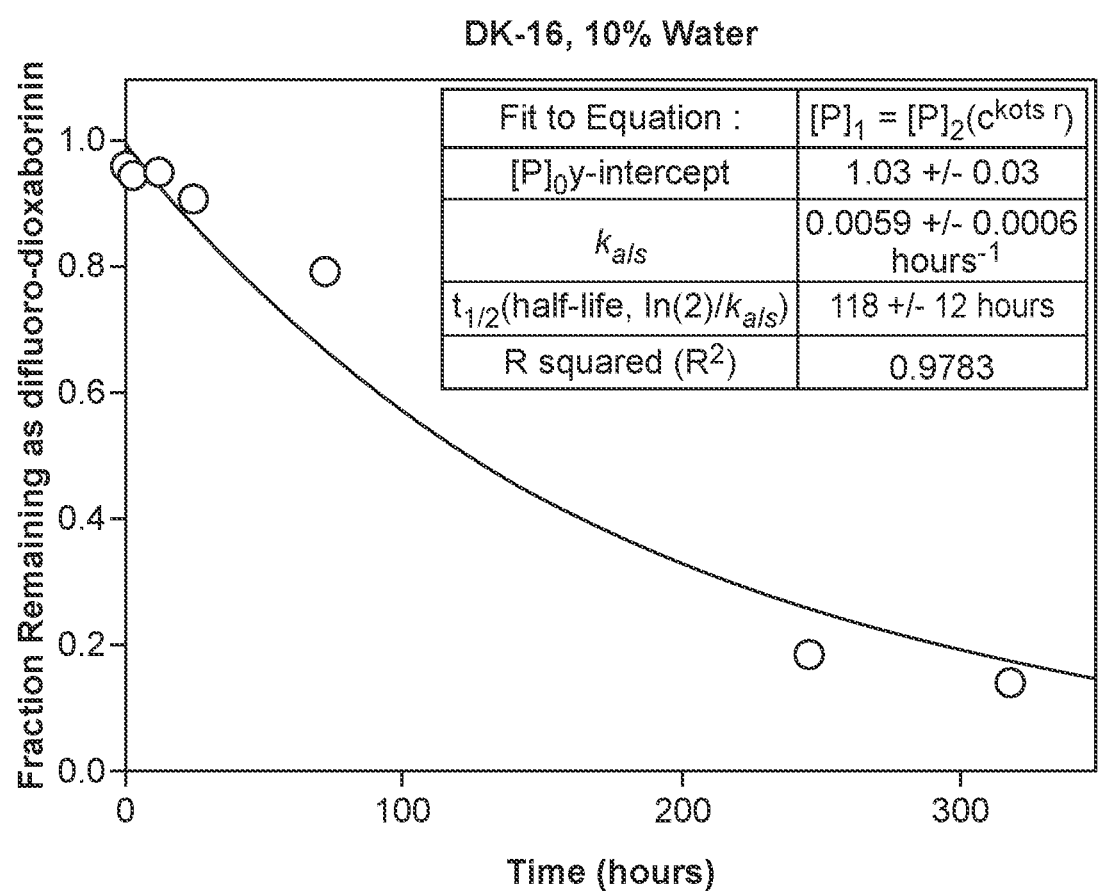
Figure 8N:
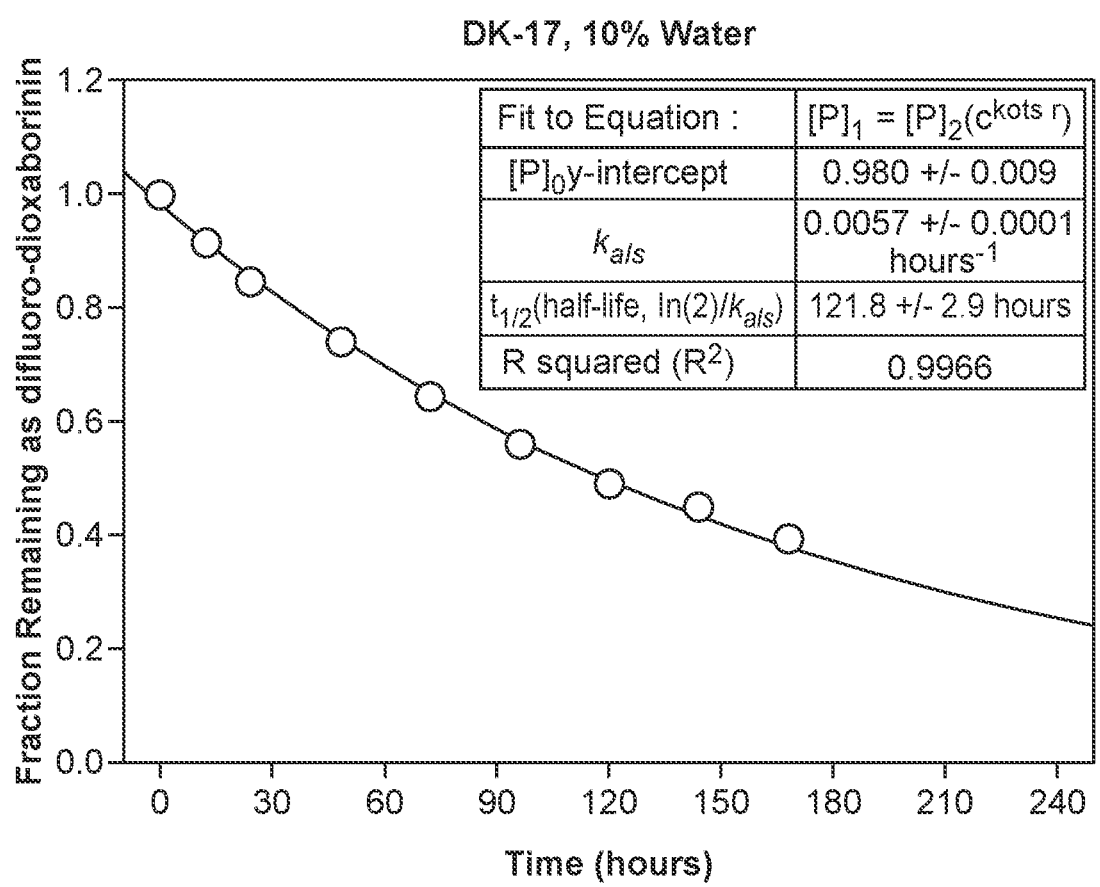
Figure 8O:
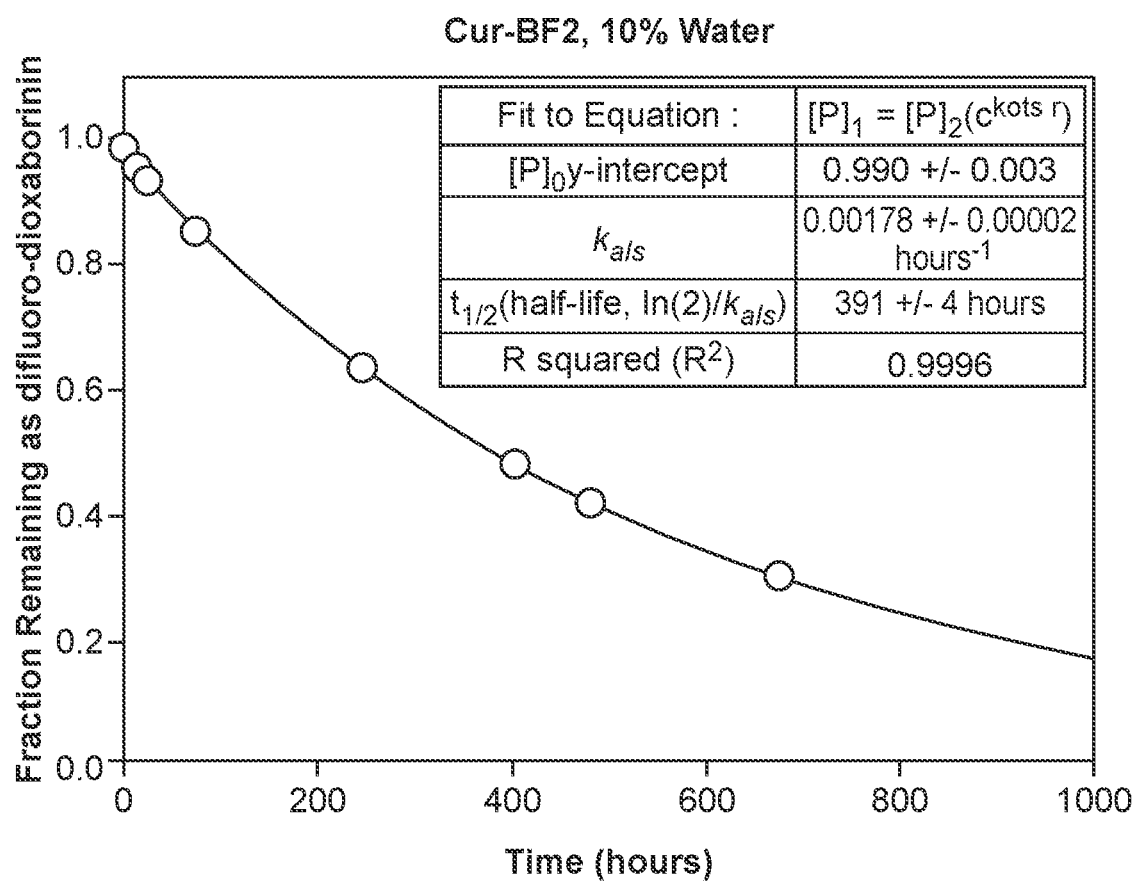
Figure 8P:
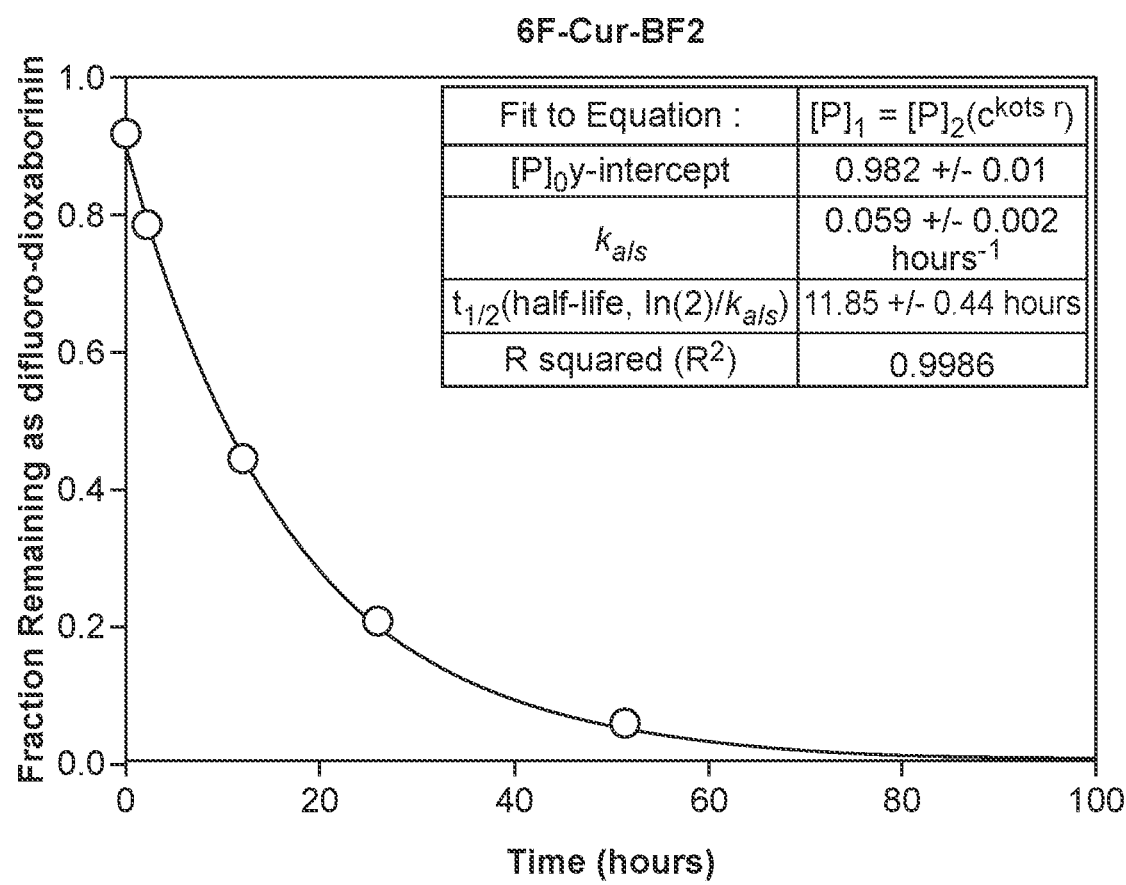
Figure 8Q:
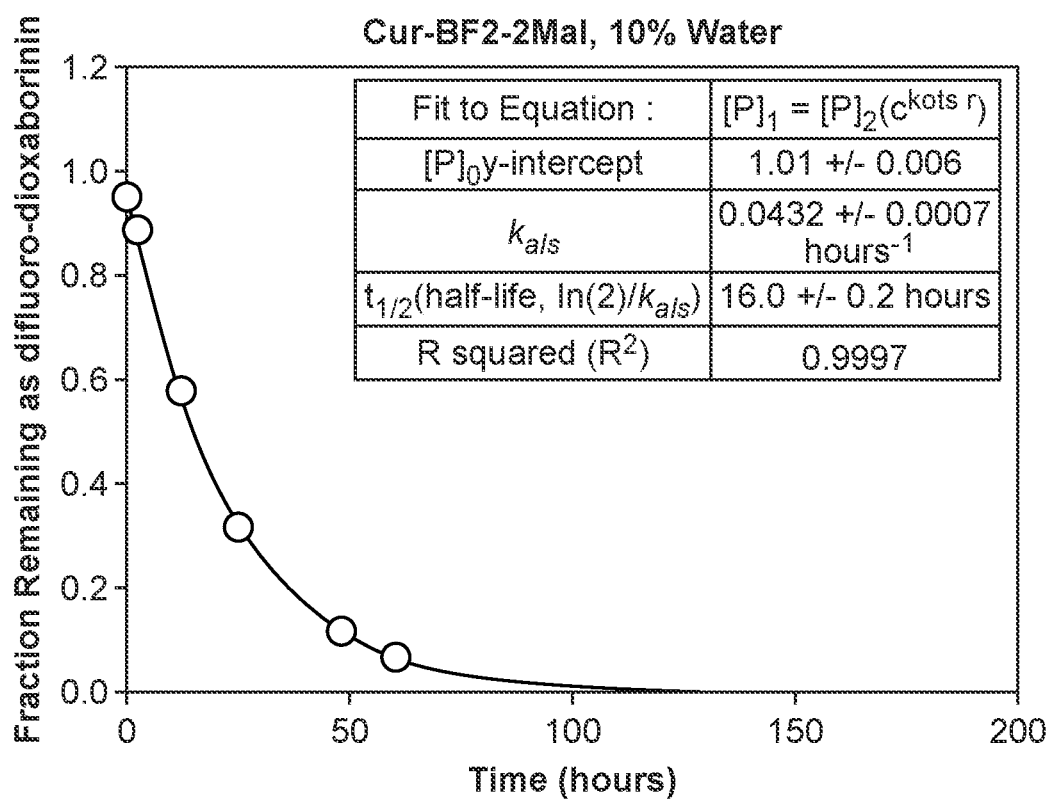

Solvolysis of prototype difluoro-dioxaborinin, DK-1: DK-1 is the lowest MW compound, and the second least-stable compound to solvolysis. DK-1 undergoes rapid solvolysis in aqueous solution. In 50 M $H_2O$ (90% water, 10% DMSO), DK-1 undergoes solvolysis with a rate constant, k, of 0.254±0.002 h$^{-1}$. DK-1's solvolytic half-life, $t_{1/2}$, is 2.73 ±0.02 hours (see Table 1 for solvolytic half-lives and FIGS. 8A-8Q for rate constants). DK-1 solvolysis is dependent on [$H_2O$]: in the absence of water (100% DMSO) DK-1 solvolysis is not observed, and in 5.55 M $H_2O$ (10-fold less water, 10% $H_2O$, 90% DMSO), solvolysis is slowed ~2.8-fold. A 9-fold reduction in [$H_2O$] results in a 2.8-fold reduction on the DK-1 solvolysis rate. Hydrolysis was also confirmed by hydrolyzing DK-1 for 15 days and analyzing via $^1$H NMR, and comparison to the $^1$H NMR of a commercially available standard.

These data suggest that DK-1 is less useful in PET imaging, as it would decompose at a half-life that is nearly on par with the decay of fluoride-18. According to the measured rate constant, 37% of DK-1 will have decomposed 1.8 hours (one fluoride-18 half-life) into a PET scan (i.e. 63% of injected DK-1 would remain intact, assuming in vitro solvolysis constants directly translate in vivo).

Solvolysis can be retarded through 6-hyperconjugation (DK-2, DK-3, DK-6, and DK-15): DK-2 and DK-3 were synthesized and evaluated in an attempt to design a more stable [$^{18}$F]-difluoro-dioxaborinin, with a retarded solvolysis rate. DK-2, DK-3, DK-6, and DK-15 all bear substituents with a C—H σ-bond at dioxaborinin position 5. This bond may stabilize the 4, 5, 6-dioxaborinin π-system through hyperconjugation; alternatively, these substituents are slightly more hydrophobic and may repel water attack on the dioxaborinin. Position 5 modification is mildly successful in stabilizing the difluoro dioxaborinin to solvolysis. Position 5 methylated (DK-2), ethylated (DK-3), proprionated (ethyl ester, DK-6), or cyclohexylated (DK-15) difluoro-dioxaborinins, are 6.2, 5.6, 1.9, and 2.5 times more resistant to solvolysis than DK-1 in 50 M $H_2O$ respectively. Like DK-1, the solvolysis of DK-2, DK-3, DK-6, and DK-15 is dependent on [$H_2O$] and DK-2, DK-3, DK-6, and DK-15 solvolysis rates are retarded 3.2-, 3.5-, 4.7-, and 5.0-fold respectively in 5.5 M $H_2O$ vs. 50 M $H_2O$ (10% water/DMSO vs. 90% water/DMSO).

These data suggest that DK-2, DK-3, DK-6, and DK-15 are more suited for $^{18}$F-PET imaging than DK-1 due to a slower solvolysis rate. Assuming rate constants at 50 M $H_2O$ translate in vivo, in a hypothetical PET imaging experiment visualized at 1.8 hours (one $^{18}$F-half-life) post-injection, 93.0±0.2% of DK-2, 92.1±0.2% of DK-3, 78.6±0.4% of DK-6, and 83.1±0.3% of DK-15 would remain intact in vivo.

Solvolysis is promoted by extending difluorodioxaborinin π-conjugation using moderately electron poor or electron-neutral substituents (DK-13 and DK-14). To evaluate the effect of extending the difluoro-dioxaborinin 4,5,6 π-system on solvolysis, compounds that bear extended π-conjugation through the difluoro-dioxaborinin moiety (positions 4, 5, and 6) were synthesized. $^{19}$F NMR solvolytic measurements were performed only in 5.55 M $H_2O$, as DK-13 and DK-14 are insoluble in 50 M $H_2O$.

DK-13 and DK-14 bear moderately electron-poor, π-substituents at the $R^1$ and $R^2$ positions and undergo more rapid solvolysis relative to DK-2. In 5.55 M $H_2O$, DK-14 undergoes solvolysis 1.7-fold more rapidly than DK-1 and is the least stable to solvolysis (of tested compounds). DK-13 undergoes solvolysis 1.4 times more slowly than DK-1, but 5.0 times more rapidly than DK-2. In summary, DK-14 is the least suitable candidate for PET contrast because it will solvolyze very quickly.

Solvolysis can be retarded through extended electron rich π-conjugation (DK-16, DK-17 and Cur-BF$_2$). Difluoro-dioxaborinins with electron-rich, extended difluoro-dioxaborinin 4, 5, 6 π-systems prove to be the most solvolytically stable. DK-16, DK-17 and Cur-BF$_2$ bear paraphenolic alcohols and ether functionality, allowing resonance structures to be contemplated showing electron donation through the positions 4, 5, and 6 of the dioxaborinin.

DK-16, DK-17, and Cur-BF$_2$ solvolysis were performed in 5.55 M $H_2O$ because they are insoluble in 50 M $H_2O$. DK-16, DK-17 and Cur-BF$_2$ undergo solvolysis 15-, 16-, and 51-times more slowly than DK-1, and 2.2-, 2.3-, and 7.3-fold more slowly than DK-2 respectively.

Chemical correlation demonstrates that electron-rich π-conjugation retards solvolysis. Of Table 1 compounds, Cur-BF$_2$ is most resistant to solvolysis. Applicant hypothesized that the pendant phenol-alcohols on Cur-BF$_2$ contribute electron density into the π-conjugated 4,5,6-difluoro-dioxaborinin π-system, thus retarding solvolytic decomposition. Applicant believes that the hypothesis may be addressed in chemical correlation experiments, where Cur-BF$_2$ phenolic alcohols are protected as esters (Cur-BF$_2$-2Mal, and 6F-Cur-BF$_2$). These compositions have a reduced ability to stabilize the 4, 5, 6 dioxaborinin π-system vs. Cur-BF$_2$. Ester functionality is less electron donating than a phenolic alcohol functionality.

As hypothesized, 6F-Cur-BF$_2$ and Cur-BF$_2$-2Mal undergo solvolysis more rapidly than Cur-BF$_2$. In 5.55 M H$_2$O, 6F-Cur-BF$_2$ and Cur-BF$_2$-2Mal undergo solvolysis 33- and 24-fold more rapidly than Cur-BF$_2$. Despite more rapid solvolysis relative to Cur-BF$_2$, 6F-Cur-BF$_2$ and Cur-BF$_2$-2Mal are solvolytically more stable than DK-1 (1.6- and 2.1-fold, respectively).

Difluoro-dioxaborinin fluorescent properties. Difluoro-dioxaborinins have expected red-shifted optical (fluorescence and absorbent) properties1-2 vs. β-diketone starting materials (Table 1). Difluorodioxaborinins are electronegative structures, and placing electropositive functionality at the R$^1$ and R$^2$ positions forms a donor-acceptor structure to induce red-shifted optical properties.[19] This donor-acceptor-pair-induced-redshift is visible even in compositions of Cur-BF$_2$; where phenolic positions are esterified. An ester is a weaker electron donor group vs. the phenol in Cur-BF$_2$, therefore, 6F-Cur-BF$_2$ and Cur-BF$_2$-2Mal show blue-shifted absorption and emission properties vs. Cur-BF$_2$ (Table 1). The difluoro-dioxaborinins presented in this research have fluorescent emissions that do not exceed 600 nm, the near-infrared region of the visible spectrum. The literature reports Cur-BF$_2$-backbone-bearing derivatives with emission wavelengths exceeding 700 nm.[3] Accordingly, the present technology provides for the transformation of literature near-infrared, optical-imaging probes that are specific for amyloid-beta deposits[5] and brown adipose tissue monitoring[12] into near-infrared optical/$^{18}$F-PET dual modality contrast.

Example 4: PET Imaging Studies

General procedure for preparation and formulation of [$^{18}$F]-6F-Cur-BF$_2$ for in vivo sentinel node mapping. 100 μL quantity of radiolabeled [$^{18}$F]-6F-Cur-BF$_2$ in a 1.5 mL Eppendorf tube was washed with 1.4 mL of pure water. The mixed solution was centrifuged at 15000 rpm for 1 min. The supernatant was removed, and these wash steps were repeated 3 more times. The purified precipitate was fully dissolved in 50 μL DMSO and analyzed with Varian HPLC equipped with a UV-Vis and radioactivity detector to confirm purity. Immediately prior to injection, DMSO solution was diluted with sterile 1 mL 1×PBS (pH 7.4). A 20 μL of the solution was subcutaneously injected into the right foot fat-pad of mice. Mice were imaged by micro-PET/CT 2 hours and 4 hours post injection.

Discussion

Clinically suitable PET-[$^{18}$F]-difluoro-dioxaborinin radiochemistry. Cur-BF$_2$ is the most solvolytically stable difluorodioxaborinin. Theoretically, [$^{18}$F]-Cur-BF$_2$ would be the most reasonable agent to translate in vivo. In practice, [$^{18}$F]-Cur-BF$_2$ proved difficult to isolate from [$^{18}$F]-fluoride ion without the use of acetonitrile-based preparative HPLC. Preparative HPLC is not compatible with rapid [$^{18}$F]-radiotracer preparation. Alternatively, cartridge-(Sep-pak) based C-18 or silica strategies for isolating [$^{18}$F]-Cur-BF$_2$ would infrequently and unpredictably result in minute [$^{18}$F]-fluoride ion contamination (1-5%). In prototype PET studies, this infrequent contamination is unacceptable, as contaminating [$^{18}$F]-fluoride ion during purification may be inadvertently mistaken for defluoridation/solvolysis in vivo.

Applicant recently published methodology describing rapid, precipitation-based removal of [$^{18}$F]-fluoride ion from [$^{18}$F]-labeled drugs.[20] This chromatography strategy is simple, rapid, and infallible. Unfortunately, [$^{18}$F]-Cur-BF$_2$ could not be purified through precipitation, as [$^{18}$F]-Cur-BF$_2$ was too hydrophilic to isolate using this methodology. Instead, [$^{18}$F]-6FCur-BF$_2$'s hydrophobic properties made it more amenable to precipitative isolation from [$^{18}$F]-fluoride ion. For this reason, [$^{18}$F]-6F-Cur-BF$_2$ was used in in vivo application.

[$^{18}$F]-difluoro-dioxaborinin PET imaging. Many publications describe the use of PET contrast in sentinel node mapping.[21-26] Radiotracers are often injected immediately prior to surgical primary tumor removal to illuminate sentinel lymph nodes for targeted resection by surgeons. Histopathologic analysis of sentinel lymph nodes is important in cancer staging. Micrometastases are likely to be present in sentinel nodes that serve the tumor, are too small to be detected by 2-fluorodeoxyglucose-PET and are exponentially less likely to be present in the nodes that do not directly serve the primary tumor (distal nodes). There are many lymph nodes in a patient, and confusing non-sentinel nodes with sentinel nodes may occur. This confusion may result in an incorrect cancer-free micrometastases diagnosis and/or immunity impairment post-surgery.[27] Intra-tumorally injected contrast is used to clearly delineate sentinel nodes for resection during surgery.[28-29]

Figure 3:
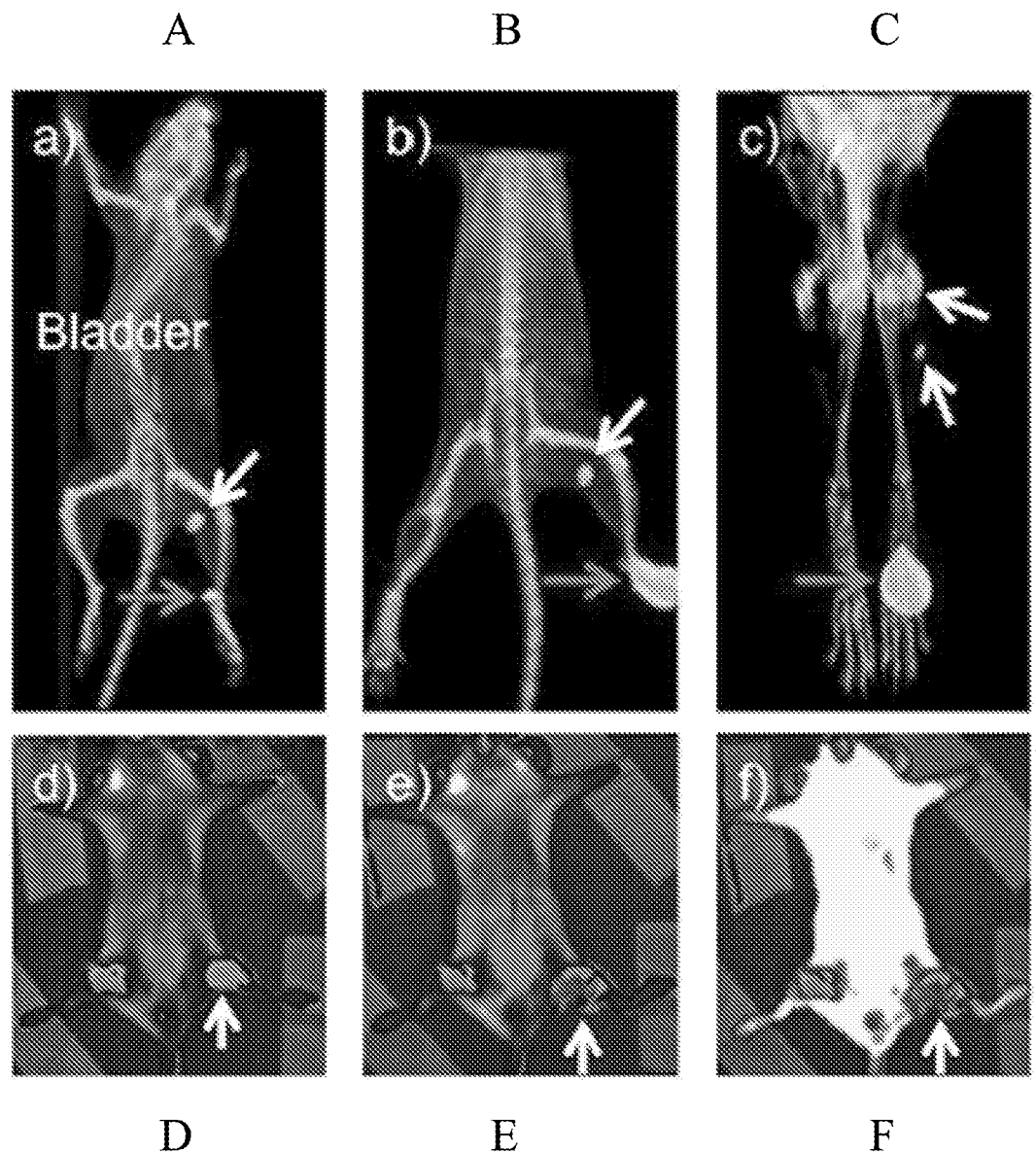
FIGS. 3A-F: Sentinel lymph node imaging using [$^{18}$F]-6F-Cur-BF$_2$ according to the working examples. The injection site (bottom arrow), sentinel lymph node (popliteal, middle arrow), and bladder (upper arrow) are visible at 2 hours, shown in FIG. 3A. After 4 hours, the bladder has evacuated and only the injection site and sentinel (popliteal) lymph node are visible in FIG. 3B. Distal lymph nodes (lumbar, iliac lymph nodes[30]) are not observed.
Figure 4:
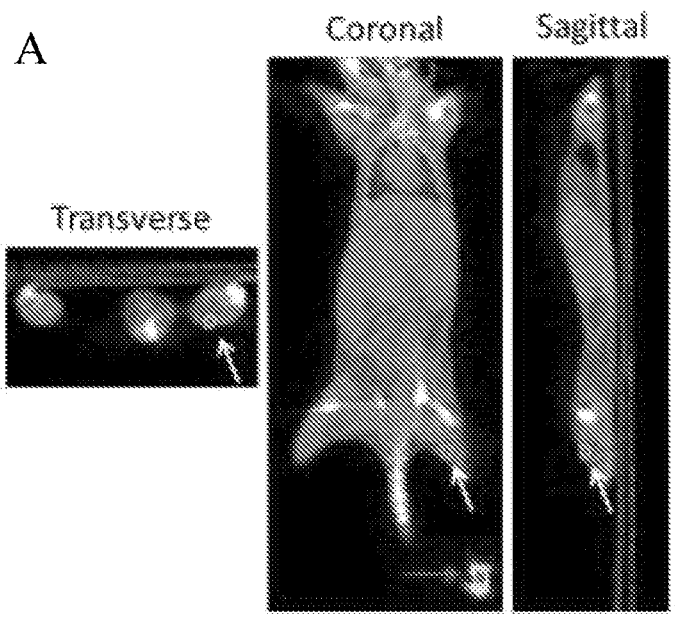
FIGS. 4A-B provide Horizontal, Coronal, and Sagittal analysis of the sentinel lymph node shown in the mouse in FIG. 3. PET tomographic sections were taken at (FIG. 4A) 2 hours and (FIG. 4B) 4 hours post injection into the right, rear footpad. The injection site (rear foot fat pad) is indicated by a bottom arrow. The sentinel lymph node (popliteal lymph node) is indicated with a white arrow.
Figure 4:
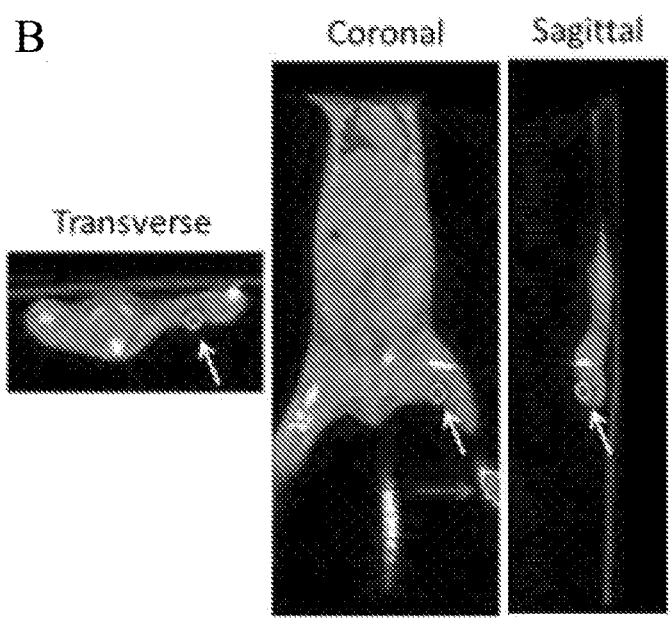
Figure 5:
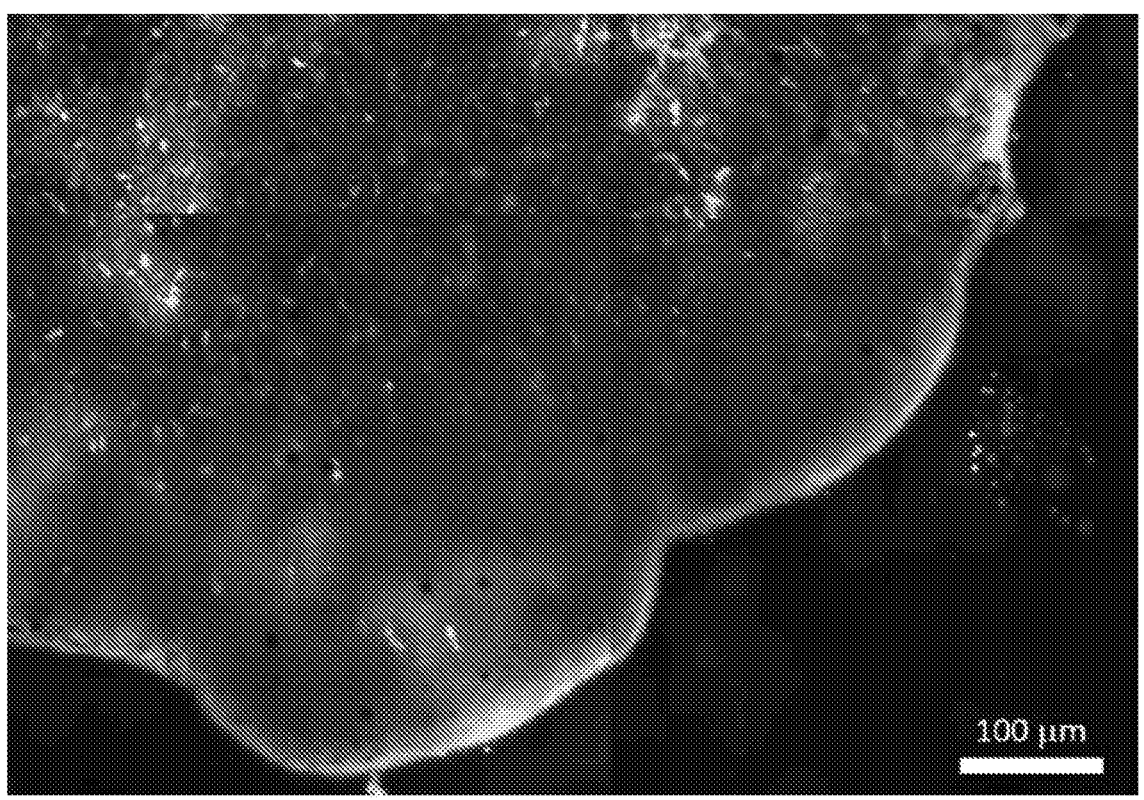
FIG. 5 provides the histology of the collected lymph node from the mouse in FIG. 4A. The mouse lymph node was collected at 2 hours post injection into the right, rear footpad. The collected lymph node was frozen with OCT Gel and cut with a thickness of 10 m. The slice was, imaged with fluorescence microscope at the channel of 6F-Cur-BF$_2$. The fluorescence of 6F-Cur-BF$_2$ was observed in the lymph node, which confirmed the deposition of 6F-Cur-BF$_2$ in the lymph node.
Figure 6:
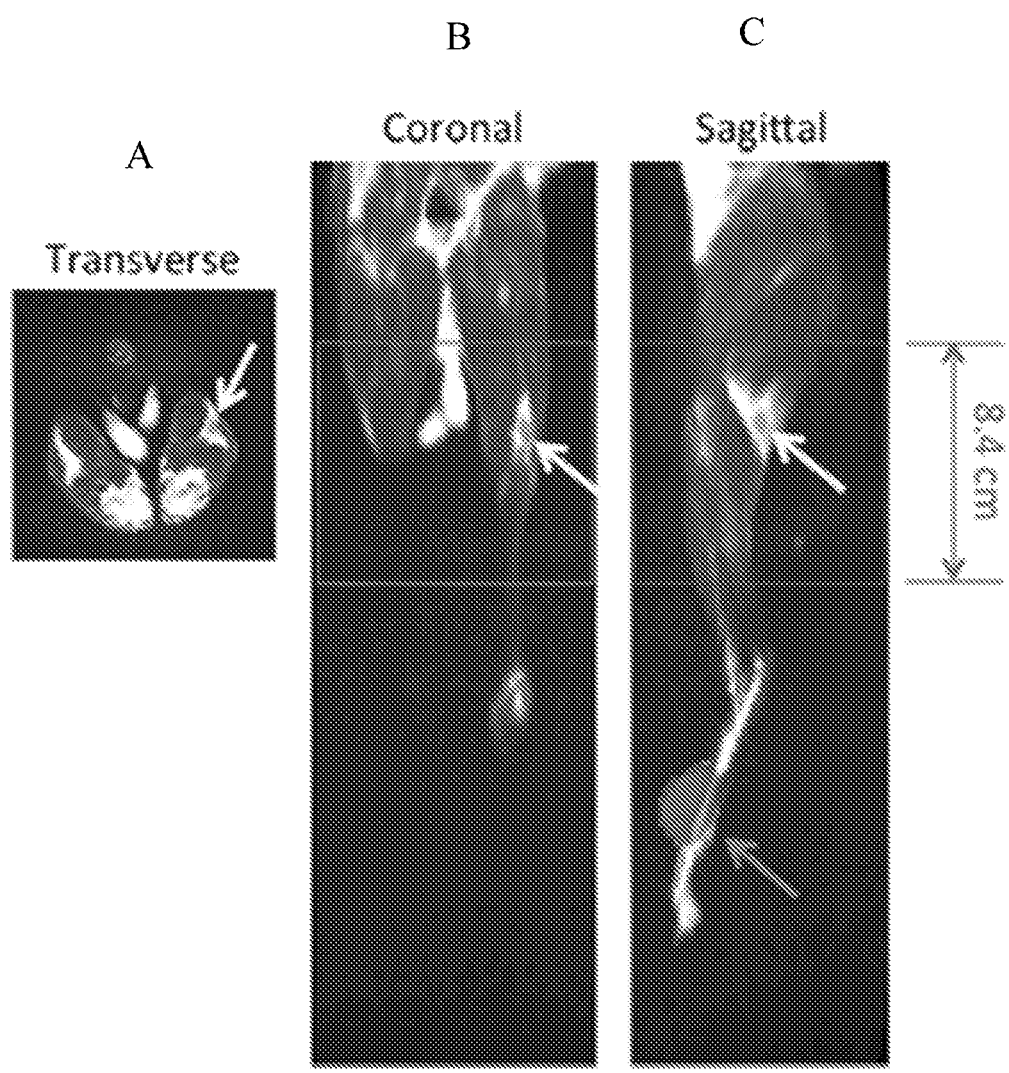
FIGS. 6A-C: A rabbit was injected with a 200 μCi dose of [$^{18}$F]-6F-Cur-BF$_2$ Magnevist (MRI contrast agent) in the right rear paw, according to the working examples. The rabbit was placed in a GE PET/MR and scanned at 5 min post injection. Horizontal (FIG. 6A), Coronal (FIG. 6B), and Sagittal (FIG. 6C) analysis of the sentinel lymph node shown in FIG. 3C. The injection site (right rear paw) is indicated by an arrow in FIG. 6C. The sentinel lymph node (popliteal lymph node) is indicated with a white arrow in each figure.

Applicant explored the utility of [$^{18}$F]-6F-Cur-BF$_2$ in sentinel node mapping (FIGS. 3A-3C). [$^{18}$F]-6F-Cur-[0218] BF$_2$ was injected as a 2% DMSO/98% 1×PBS solution into the right foot fat pad of mice.

[$^{18}$F]-6F-Cur-BF$_2$ contrast imaging of sentinel nodes was performed in mice and in rabbits (FIGS. 4A, 4B, 5, and 6A-6C). In both cases, only the sentinel nodes (and not distal nodes) are delineated by PET. Sentinel lymph nodes and tracks are visible in rabbits. Flow through to distal (lumbar) nodes are not observed. In the unobserved case that flow-through to non-sentinel nodes is observed, dynamic PET imaging (not shown) would also delineate sentinel node status.

[$^{18}$F]-6F-Cur-BF$_2$ contrast is superior to indocyanine green (ICG) and lymphazurin (isosulfan blue) non-targeted fluorescent contrasts,[31] which travel through sentinel nodes to delineate multiple non-sentinel nodes, and do not allow for PET imaging.

Applicant attempted sentinel lymph node imaging with [$^{18}$F]-6FCur-BF$_2$ by fluorescence with 430 nm excitation and 520 nm emission filters. Unfortunately, the skin of the mouse has a high degree of autofluorescence, and the sentinel node is difficult to visualize through the skin with 6F-Cur-BF$_2$ (fluorescence, FIG. 3D). The removal of the skin is necessary for fluorescent node visualization (FIG. 3E, and overexposed image shown in FIG. 3F). The collected lymph node is confirmed in histology. Fluorescence signal is visible in histology (FIG. 5), which confirms [$^{18}$F]-6F-Cur-BF$_2$ deposition at the lymph node in PET images.

Rabbit [$^{18}$F]-6F-Cur-BF$_2$ contrast imaging of sentinel nodes procedure: The imaging shown in FIG. 6 was obtained as follows. Two New Zealand white strain rabbits (Animal One: 3.2 kg; Animal Two: 2.8 kg) were used in this experiment. In animal One: a 0.6 ml mixture of 0.4 ml (400 µCi) of [18F]-6F-Cur-BF$_2$ and 0.8 ml of Magnevist (MRI contrast agent) were injected subdermally in the rear right pawn of the lower extremity. Applicant did not apply any message (Procedure routinely is being done after injection for Lymphography imaging). Imaging was performed using 3 d spoiled gradient echosequence LAVA-Flex (DIXON) with 28 seconds scan time. Scan was performed with an eight-channel body array coil. The acquisition was started at 5 min. Applicant was able to see lymph node at 10 min as seen in images. Animal Two: 0.6 ml mixture of 0.4 ml (1200 Ci) of [18F]-6F-Cur-BF$_2$ and 0.8 ml of Magnevist (MRI contrast agent) was injected subdermally in the rear right pawn of the lower extremity. Same procedures were applied as animal one.

Figure 7:
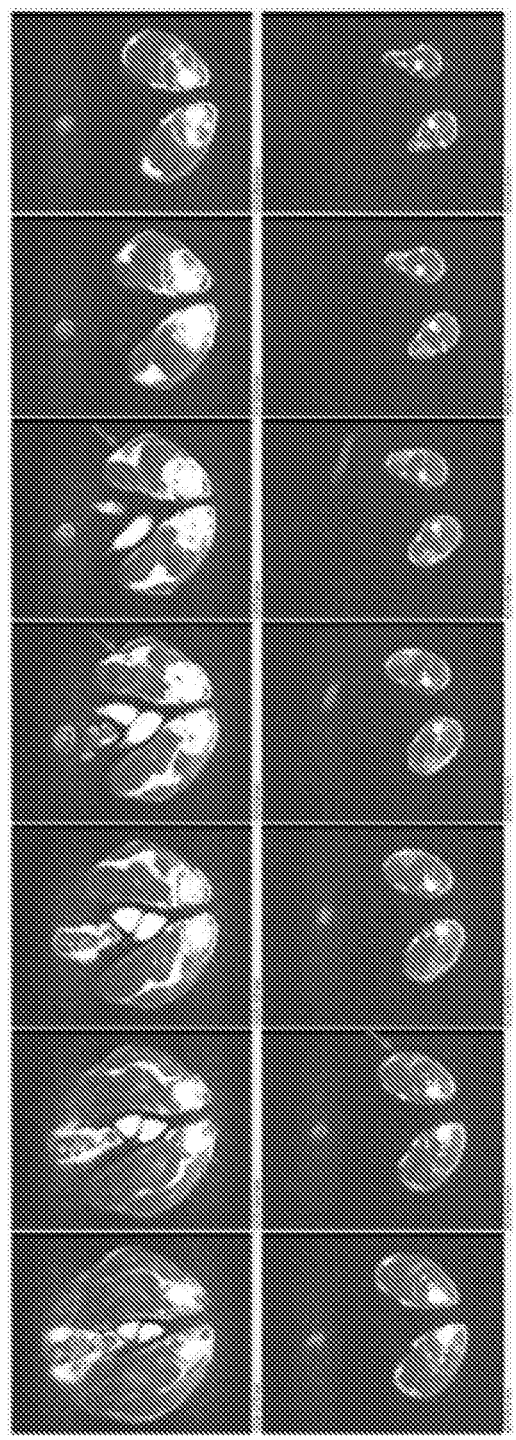
FIG. 7 provides PET coronal scans of rabbit according to the procedure in Example 4. The arrows indicate two sentinel lymph nodes. The slices of these images were extracted from the rectangle of FIG. 6 with a thickness of 6 mm.

The PET scans of FIG. 7 were obtained as follows. A rabbit was injected with a 200 µCi dose of [$^{18}$F]-6F-Cur-BF$_2$ Magnevist (MRI contrast agent) in the right rear paw. The rabbit was placed in a GE PET/MR and scanned at 5 min post injection. Two sentinel lymph nodes (popliteal, arrow) are visible at 5 min in imaging of 0.6 cm coronal section through the knee. PET (NIH color table)/MR (grey) coronal images are shown. The slices (planes along the x-axis, were extracted from the red rectangle in FIG. 6 with thickness of 6 mm.

Example 5: Effect on Cancer Cell Proliferation

| Cell Line | Time | Curcumin-BF$_2$ IC$_{50}$ (µM) | Curcumin IC$_{50}$ (µM) | Fold Increase in Potency |
|---|---|---|---|---|
| A549 | 24 h | 27 ± 3 | 50 ± 4 | 1.8 x |
|  | 48 h | 5.5 ± 0.3 | 25 ± 1 | 4.5 x |
| HeLa | 24 h | 5.4 ± 0.4 | 16 ± 3 | 3.2x |
|  | 48 h | 4.2 ± 0.2 | 19 ± 6 | 4.5 x |
| HCT116 | 24 h | 3.31 ± 0.04 | 27 ± 5 | 8.2 x |
|  | 48 h | 4.3 ± 0.2 | 16 ± 2 | 3.7 x |
| MDA-MB-231 | 24 h | 11 ± 1 | 32 ± 13 | 2.9 x |
|  | 48 h | 6 ± 1 | 26 ± 6 | 4.3 x |
| MCF-7 | 24 h | 10 ± 4 | 27 ± 8 | 2.7 x |
|  | 48 h | 4.8 ± 0.2 | 35 ± 3 | 7.2 x |

FIGS. 10A-10E show the inhibition of cell proliferation for the cell lines in Example 5 above over 24 and 48 h periods, respectively. As shown in FIGS. 11A-11E, cell viability as a function of Curcumin-BF$_2$ concentration was evaluated for each of the cell lines in Example 5, showing the compounds of the present technology are effective in inhibiting cancer cell proliferation.

REFERENCES

1. Weiss, H.; Reichel, J.; Gorls, H.; Schneider, K. R. A.; Micheel, M.; Prohl, M.; Gottschaldt, M.; Dietzek, B.; Weigand, W. Beilstein J. Org. Chem. 2017, 13, 2264-2272.
2. Stefane, B. Org. Lett. 2010, 12, 2900-2903.
3. Zhang, X.; Tian, Y.; Zhang, C.; Tian, X.; Ross, A. W.; Moir, R. D.; Sun, H.; Tanzi, R. E.; Moore, A.; Ran, C. Proc. Natl. Acad. Sci. U.S.A 2015, 112, 9734-9739.
4. Weissleder, R.; Ntziachristos, V. Nat. Med. 2003, 9, 123-128.
5. Ran, C.; Xu, X.; Raymond, S. B.; Ferrara, B. J.; Neal, K.; Bacskai, B. J.; Medarova, Z.; Moore, A. J. Am. Chem. Soc. 2009, 131, 15257-15261.
6. An, F.-F.; Chan, M.; Kommidi, H.; Ting, R. Am. J. Roentgenol. 2016, 207, 266-273.
7. Hong, G.; Antaris, A. L.; Dai, H. Nat. Biomed. Eng. 2017, 1, 0010.
8. Kostikov, A. P.; Chin, J.; Orchowski, K.; Schirrmacher, E.; Niedermoser, S.; Jurkschat, K.; Iovkova-Berends, L.; Wangler, C.; Wangler, B.; Schirrmacher, R. Nat. Protoc. 2012, 7, 1956-1963.
9. Perrin, D. M. Acc. Chem. Res. 2016, 49, 1333-1343.
10. Liu, S.; Lin, T.-P.; Li, D.; Leamer, L.; Shan, H.; Li, Z.; Gabbai, F. P.; Conti, P. S. Theranostics 2013, 3, 181-189.
11. Liu, Z.; Pourghiasian, M.; Radtke, M. A.; Lau, J.; Pan, J.; Dias, G. M.; Yapp, D.; Lin, K.-S.; Bénard, F.; Perrin, D. M. Angew. Chem. Int. Ed. 2014, 53, 11876-11880.
12. Zhang, X.; Tian, Y.; Zhang, H.; Kavishwar, A.; Lynes, M.; Brownell, A.-L.; Sun, H.; Tseng, Y.-H.; Moore, A.; Ran, C. Sci. Rep. 2015, 5, 13116.
13. Hendricks, J. A.; Keliher, E. J.; Wan, D.; Hilderbrand, S. A.; Weissleder, R.; Mazitschek, R. Angew. Chem. Int. Ed. 2012, 51, 4603-4606.
14. Ting, R.; Harwig, C. W.; Lo, J.; Li, Y.; Adam, M. J.; Ruth, T. J.; Perrin, D. M. J. Org. Chem. 2008, 73, 4662-70.
15. Liu, S.; Li, D.; Shan, H.; Gabbai, F. P.; Li, Z.; Conti, P. S. Nucl. Med. Biol. 2014, 41, 120-126.
16. Kowada, T.; Maeda, H.; Kikuchi, K. Chem. Soc. Rev. 2015, 44, 4953-4972.
17. Eaton, D. F. J. Photochem. Photobiol. B 1988, 2, 523-531.
18. Saha, G. B. Synthesis of PET Radiopharmaceuticals. In Basics of PET Imaging: Physics, Chemistry, and Regulations, Springer New York: New York, NY, 2010; 131-150.
19. Bauer, S. H.; Finlay, G. R.; Laubengayer, A. W. J. Am. Chem. Soc. 1943, 65, 889-895.
20. Wang, M.; Kommidi, H.; Tosi, U.; Guo, H.; Zhou, Z.; Schweitzer, M. E.; Wu, L. Y.; Singh, R.; Hou, S.; Law, B.; Ting, R.; Souweidane, M. M. Mol. Cancer Ther. 2017, 16, 2902-2912.
21. Sun, Y.; Yu, M.; Liang, S.; Zhang, Y.; Li, C.; Mou, T.; Yang, W.; Zhang, X.; Li, B.; Huang, C.; Li, F. Biomaterials 2011, 32, 2999-3007.
22. Shaffer, T. M.; Harmsen, S.; Khwaja, E.; Kircher, M. F.; Drain, C. M.; Grimm, J. Nano Lett. 2016, 16, 5601-5604.
23. Bradbury, M. S.; Pauliah, M.; Zanzonico, P.; Wiesner, U.; Patel, S. Wiley Interdiscip. Rev.: Nanomed. Nanobiotechnol. 2016, 8, 535-553.
24. Tang, L.; Yang, X.; Dobrucki, L. W.; Chaudhury, I.; Yin, Q.; Yao, C.; Lezmi, S.; Helferich, W. G.; Fan, T. M.; Cheng, J. Angew. Chem. Int. Ed. 2012, 124, 12893-12898.
25. Ni, D.; Jiang, D.; Ehlerding, E. B.; Huang, P.; Cai, W. Acc. Chem. Res. 2018, 51, 778-788.
26. Cheng, L.; Kamkaew, A.; Shen, S.; Valdovinos, H. F.; Sun, H.; Hernandez, R.; Goel, S.; Liu, T.; Thompson, C. R.; Barnhart, T. E.; Liu, Z.; Cai, W. Small 2016, 12, 5750-5758.
27. Hensler, T.; Heidecke, C.-D.; Hecker, H.; Heeg, K.; Bartels, H.; Zantl, N.; Wagner, H.; Siewert, J.-R.; Holzmann, B. J. Immunol. 1998, 161, 2655-2659.
28. Okholm, C.; Goetze, J. P.; Svendsen, L. B.; Achiam, M. P. Scand. J. Gastroenterol. 2014, 49, 1027-1034.
29. Cui, M.; Gong, C.; Jiang, B.; Yao, Z.; Chen, L.; Di, J.; Xing, J.; Yang, H.; Zhang, C.; Zhang, N.; Liu, M.; Tan, F.; Wang, Z.; Su, X. Med. Oncol. 2015, 32, 253.

30. Ting, R.; Aguilera, T. A.; Crisp, J. L.; Hall, D. J.; Eckelman, W. C.; Vera, D. R.; Tsien, R. Y. *Bioconjug. Chem.* 2010, 21, 18111819.
31. Kitai, T.; Inomoto, T.; Miwa, M.; Shikayama, T. *Breast Cancer* 2005, 12, 211-215.
32. Jacobson, O.; Kiesewetter, D. O.; Chen, X. *Bioconjug. Chem.* 2015, 26, 1-18.
33. Bhalla, R.; Levason, W.; Luthra, S. K.; McRobbie, G.; Sanderson, G.; Reid, G. *Chem. Eur. J.* 2015, 21, 4688-4694.
34. Bernard-Gauthier, V.; Lepage, M.; Waengler, B.; Bailey, J. A.; Liang, S. H.; Perrin, D.; Vasdev, N.; Schirrmacher, R. *J. Nucl. Med.* 2017. DOI: 10.2967/jnumed.117.197095.
35. Chansaenpak, K.; Vabre, B.; Gabbai, F. P. *Chem. Soc. Rev.* 2016, 45, 954-971.
36. Bhalla, R.; Darby, C.; Levason, W.; Luthra, S. K.; McRobbie, G.; Reid, G.; Sanderson, G.; Zhang, W. *Chem. Sci.* 2014, 5, 381391.
37. Keliher, E. J.; Klubnick, J. A.; Reiner, T.; Mazitschek, R.; Weissleder, R. *ChemMedChem* 2014, 9, 1368-1373.
38. Kondo, N.; Temma, T.; Deguchi, J.; Sano, K.; Ono, M.; Saji, H. *J. Control. Release* 2015, 220, 476-483.
39. Li, Z.; Lin, T.-P.; Liu, S.; Huang, C.-W.; Hudnall, T. W.; Gabbai, F. P.; Conti, P. S. *Chem. Commun.* 2011, 47, 9324-9326.
40. Liu, S.; Li, D.; Zhang, Z.; Surya Prakash, G. K.; Conti, P. S.; Li, Z. *Chem. Commun.* 2014, 50, 7371-7373.
41. Hudnall, T. W.; Gabbai, F. P. *Chem. Commun.* 2008, 44, 4596-4597.
42. Wamser, C. A. *J. Am. Chem. Soc.* 1951, 73, 409-416.
43. Luo, S.; Zhang, E.; Su, Y.; Cheng, T.; Shi, C. *Biomaterials* 2011, 32, 7127-7138.
44. Kim, H. N.; Lee, M. H.; Kim, H. J.; Kim, J. S.; Yoon, J. *Chem. Soc. Rev.* 2008, 37, 1465-1472.
45. Alford, R.; Simpson, H. M.; Duberman, J.; Hill, G. C.; Ogawa, M.; Regino, C.; Kobayashi, H.; Choyke, P. L. *Mol. Imaging* 2009, 8, 341-354.

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such claims:

A. A compound according to Formula (I)

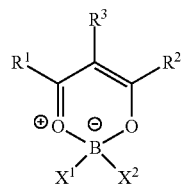
(I)

or a pharmaceutically acceptable salt and/or solvate thereof, wherein
$X^1$ and $X^2$ are each independently $^{18}F$ or $^{19}F$;
$R^1$ and $R^2$ are each independently alkyl, amine, perfluoroalkyl, alkenyl, alkynyl, aryl, or aralkenyl; and
$R^3$ is H, halo, alkyl, alkyl ester, alkenyl, alkynyl, aryl, or aralkenyl;
or wherein:
$R^1$ and $R^3$ or $R^2$ and $R^3$ join to form a 6-membered cycloalkyl or heterocyclyl; or
$R^1$ and $R^3$, $R^2$ and $R^3$, or $R^1$, $R^2$, and $R^3$ join to form a substituted or unsubstituted polycyclic ring, wherein the polycyclic ring comprises fused cycloalkyl, heterocycloalkyl, aryl, or heteroaryl rings.

B. The compound of Paragraph A, wherein $X^1$ is $^{18}F$ and $X^2$ is $^{18}F$ or $^{19}F$.
C. The compound of Paragraph A or Paragraph B, wherein each of $X^1$ and $X^2$ is $^{18}F$.
D. The compound of any one of Paragraphs A-C, wherein $R^1$ and $R^2$ are each independently alkyl, alkenyl, aryl, or —CH=CH-aryl.
E. The compound of Paragraph D, wherein the aryl of the —CH=CH-aryl is a substituted or unsubstituted phenyl.
F. The compound of Paragraph D or Paragraph E, wherein the aryl of the —CH=CH-aryl is represented by Formula (II):

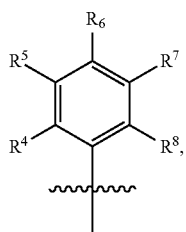
(II)

wherein:
$R^4$, $R^5$, $R^6$, $R^7$, and $R^8$ are each independently H, halo, hydroxyl, $C_1$-$C_6$ alkyl, $C_1$-$C_6$ alkoxy, or —OC(O)$R^9$, wherein $R^9$ may be substituted or unsubstituted $C_1$-$C_3$ alkyl, substituted or unsubstituted aryl, represented by a structure of Formula (III):

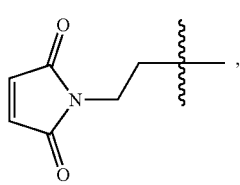
(III)

or
represented by a structure of Formula (IV):

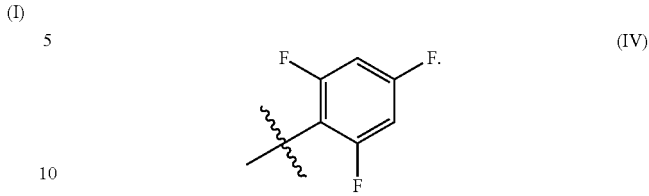
(IV)

G. The compound of Paragraph F, wherein $R^4$, $R^7$, and $R^x$ are each independently be H.
H. The compound of Paragraph F or Paragraph G, wherein $R^5$ and $R^6$ are each independently be a hydroxyl or a $C_1$-$C_6$ alkoxy.
I. The compound of any one of Paragraphs F-H, wherein $R^5$ is methoxy.
J. The compound of any one of Paragraphs F-I, wherein, $R^6$ is a —C(O)O$R^9$.
K. The compound of Paragraph J, wherein $R^9$ is a structure of Formula (III).
L. The compound of Paragraph J, wherein $R^9$ is a structure of Formula (IV).
M. The compound of any one of Paragraphs A-L, wherein $R^3$ is H.
N. The compound of any one of Paragraphs A-L, wherein $R^3$ is a $C_1$-$C_6$ alkyl.
O. The compound of any one of Paragraphs A-L, wherein $R^3$ is —CH$_2$CH$_2$C(O)OCH$_2$CH$_3$.
P. The compound of any one of Paragraphs A-O, wherein the compound of Formula (I), or a pharmaceutically acceptable salt and/or solvate thereof, is Curcumin-BF$_2$.
Q. The compound of Paragraph P, wherein each fluorine atom of Curcumin-BF$_2$ is independently $^{18}F$ or $^{19}F$.
R. The compound of any one of Paragraphs A-C, wherein $R^1$ and $R^3$ join form a 6-membered cycloalkyl or heterocyclyl.
S. The compound of any one of Paragraphs A-C, wherein $R^1$ and $R^3$ join to form a substituted or unsubstituted polycyclic ring comprising fused cycloalkyl rings, aryl rings, or combinations.
T. The compound of Paragraph S, wherein $R^2$ is an amine.
U. The compound of any one of Paragraphs A-C, wherein $R^2$ and $R^3$ join to form a substituted or unsubstituted polycyclic ring that includes fused cycloalkyl rings, aryl rings, or combinations thereof.
V. The compound of Paragraph U, wherein $R^1$ is an amine.
W. The compound of any one of Paragraphs S—V, wherein the compound of Formula (I) is tetraglycerine-BF$_2$, glycylcycline-BF$_2$, or a pharmaceutically acceptable salt and/or solvate of tetraglycerine-BF$_2$, or a pharmaceutically acceptable salt and/or solvate of glycylcycline-BF$_2$.
W. The compound of Paragraph W, wherein each fluorine atom of tetraglycerine-BF$_2$ or glycylcycline-BF$_2$ is independently $^{18}F$ or $^{19}F$.
Y. The compound of any one of Paragraphs A-C, wherein $R^1$, $R^2$, and $R^3$ may join to form a substituted or unsubstituted polycyclic ring, wherein the polycyclic ring comprises fused cycloalkyl rings, aryl rings, or combinations thereof.
Z. The compound of Paragraph Y, wherein the compound of Formula (I), or a pharmaceutically acceptable salt and/or solvate thereof, is emodin-BF$_2$, doxorubicin-BF$_2$, or daunorubicin-BF$_2$.

AA. The compound of Paragraph Y or Paragraph Z, wherein each fluorine atom of emodin-BF$_2$, doxorubicin-BF$_2$, or daunorubicin-BF$_2$ is independently $^{18}$F or $^{19}$F.

AB. The compound of any one of Paragraphs A-AA, exhibiting no greater than about 50% of detectable degradation during the first 24 hours after administration to a subject in need thereof.

AC. A pharmaceutical composition comprising the compound according to any one of Paragraphs A-AB and one or more pharmaceutically acceptable carriers.

AD. The pharmaceutical composition of Paragraph AC, further comprising a non-BF$_2$ modified counterpart to the compound of Formula (I), or a pharmaceutically acceptable salt and/or solvate thereof, wherein the non-BF$_2$ modified counterpart is represented by a structure of Formula (V):

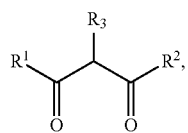

R$^1$ and R$^2$ are each independently alkyl, amine, perfluoroalkyl, alkenyl, alkynyl, aryl, or aralkenyl; and R$^3$ is H, halo, alkyl, alkyl ester, alkenyl, alkynyl, aryl, or aralkenyl;

or wherein:
R$^1$ and R$^3$ or R$^2$ and R$^3$ join to form a 6-membered cycloalkyl or heterocyclyl; or
R$^1$ and R$^3$, R$^2$ and R$^3$, or R$^1$, R$^2$, and R$^3$ join to form a substituted or unsubstituted polycyclic ring, wherein the polycyclic ring comprises fused cycloalkyl, heterocycloalkyl, aryl, or heteroaryl rings.

AE. A method comprising administering a compound of any one of Paragraphs A-AB to a subject suffering from a cancer.

AF. The method of Paragraph AE, wherein the method comprises administering a pharmaceutical composition comprising a compound of any one of Paragraphs A-AB and a pharmaceutically acceptable carrier.

AG. The method of Paragraph AE, wherein the method comprises administering an effective amount of the compound for imaging the cancer.

AH. The method of any one of Paragraphs AE-AG, further comprising, subsequent to the administering, detecting one or more of positron emission, gamma rays from positron emission and annihilation, and Cerenkov radiation due to positron emission.

AI. The method of any one of Paragraphs AE-AH, wherein the administration comprises intravenous administration.

AJ. The method of any one of Paragraphs AE-AI, further comprising performing the method for imaging cancer in conjunction with one or more additional cancer treatment processes or procedures.

AK. The method of Paragraph AJ, wherein the one or more additional cancer treatment processes or procedures comprises tissue biopsy, surgical procedures, pathology analysis, histology analysis, tumor status determinations, monitoring progress of cancer therapy, monitoring the progress of cancer surgery, or any combination of two or more thereof.

AL. The method of any one of Paragraphs AE-AK, wherein about 0.01 mCi to about 10 mCi of the compound of Formula (I), or a pharmaceutically acceptable salt and/or solvate thereof, is administered to the subject.

AM. The method of any one of Paragraphs AE-AL, wherein the administering occurs prior to, or during a PET scan.

AN. The method of any one of Paragraphs AE-AM, wherein the subject is human.

AO. The method of any one of Paragraphs AE-AN, wherein the compound is Curcumin-BF$_2$, or a pharmaceutically acceptable salt and/or solvate thereof.

AP. A method for inhibiting the proliferation of one or more cancer cells, the method comprising contacting the one or more cancer cells with a compound according to any one of Paragraphs A-AB.

AQ. The method of Paragraph AP, wherein the method comprises contacting the one or more cancer cells with a pharmaceutical composition comprising the compound and a pharmaceutically acceptable carrier.

AR. The method of Paragraph AP or Paragraph AQ, wherein the compound is Curcumin-BF$_2$ or a pharmaceutically acceptable salt and/or solvate thereof.

AS. The method of any one of Paragraphs AP-AR, wherein the cancer cells comprise lung cancer cells, HeLa cells, colon cancer cells, MDA-MB-231 cells, breast cancer cells, or a combination of any two or more thereof.

AT. A method for treating cancer in a subject comprising administering to the subject in need thereof a therapeutically effective amount of a compound according to any one of Paragraphs A-AB.

AU. A kit for imaging of cancer, inhibiting proliferation of cancer cells, and/or treating cancer in a subject in need thereof, the kit comprising a compound according to Formula (Ia):

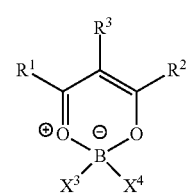

or a pharmaceutically acceptable salt and/or solvate thereof; wherein

X$^3$ and X$^4$ are each independently $^{19}$F; and

R$^1$ and R$^2$ are each independently alkyl, amine, perfluoroalkyl, alkenyl, alkynyl, aryl, or aralkenyl; and R$^3$ is H, halo, alkyl, alkyl ester, alkenyl, alkynyl, aryl, or aralkenyl;

or wherein:
R$^1$ and R$^3$ or R$^2$ and R$^3$ join to form a 6-membered cycloalkyl or heterocyclyl; or
R$^1$ and R$^3$, R$^2$ and R$^3$, or R$^1$, R$^2$, and R$^3$ join to form a substituted or unsubstituted polycyclic ring, wherein the polycyclic ring comprises fused cycloalkyl, heterocycloalkyl, aryl, or heteroaryl rings.

Other embodiments are set forth in the following claims, along with the full scope of equivalents to which such claims are entitled.

What is claimed is:

1. A compound according to Formula (I)

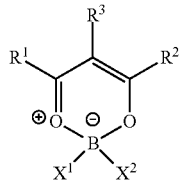

or a pharmaceutically acceptable salt and/or solvate thereof, wherein
$X^1$ and $X^2$ are each independently $^{18}F$ or $^{19}F$; and
$R^1$ and $R^3$, $R^2$ and $R^3$, or $R^1$, $R^2$, and $R^3$ join to form a substituted or unsubstituted polycyclic ring;
wherein the compound of Formula (I) or a pharmaceutically acceptable salt and/or solvate thereof is tetracycline-$BF_2$, glycylcycline-$BF_2$, emodin-$BF_2$, doxorubicin-$BF_2$, or daunorubicin-$BF_2$.

2. The compound of claim 1, wherein the compound of Formula (I) or a pharmaceutically acceptable salt and/or solvate thereof is tetracycline-$BF_2$ or glycylcycline-$BF_2$.

3. The compound of claim 2, wherein each fluorine atom of tetracycline-$BF_2$ or glycylcycline-$BF_2$ is independently $^{18}F$ or $^{19}F$.

4. The compound of claim 1, wherein the compound of Formula (I), or a pharmaceutically acceptable salt and/or solvate thereof, is emodin-$BF_2$, doxorubicin-$BF_2$, or daunorubicin-$BF_2$.

5. The compound of claim 4, wherein each fluorine atom of emodin-$BF_2$, doxorubicin-$BF_2$, or daunorubicin-$BF_2$ is independently $^{18}F$ or $^{19}F$.

6. A pharmaceutical composition comprising a compound of claim 1 and one or more pharmaceutically acceptable carriers.

7. A method comprising administering a compound of claim 1 to a subject suffering from a cancer.

8. The method of claim 7, wherein the method comprises administering an effective amount of the compound for imaging the cancer.

9. The method of claim 7, further comprising, subsequent to the administering, detecting one or more of positron emission, gamma rays from positron emission and annihilation, and Cerenkov radiation due to positron emission.

10. The method of claim 7, wherein the administration comprises intravenous administration.

11. A method for inhibiting the proliferation of one or more cancer cells, the method comprising contacting the one or more cancer cells with a compound of claim 1.

12. A method for treating cancer in a subject comprising administering to the subject in need thereof a therapeutically effective amount of a compound of claim 1.

13. The pharmaceutical composition of claim 6, wherein at least one fluorine atom of tetracycline-$BF_2$, glycylcycline-$BF_2$, emodin-$BF_2$, doxorubicin-$BF_2$, or daunorubicin-$BF_2$ is independently $^{19}F$.

14. The method of claim 7, wherein at least one fluorine atom of tetracycline-$BF_2$, glycylcycline-$BF_2$, emodin-$BF_2$, doxorubicin-$BF_2$, or daunorubicin-$BF_2$ is independently $^{19}F$.

15. The method of claim 8, wherein at least one fluorine atom of tetracycline-$BF_2$, glycylcycline-$BF_2$, emodin-$BF_2$, doxorubicin-$BF_2$, or daunorubicin-$BF_2$ is independently $^{19}F$.

16. The method of claim 9, wherein at least one fluorine atom of tetracycline-$BF_2$, glycylcycline-$BF_2$, emodin-$BF_2$, doxorubicin-$BF_2$, or daunorubicin-$BF_2$ is independently $^{19}F$.

17. The method of claim 11, wherein at least one fluorine atom of tetracycline-$BF_2$, glycylcycline-$BF_2$, emodin-$BF_2$, doxorubicin-$BF_2$, or daunorubicin-$BF_2$ is independently $^{19}F$.

18. The method of claim 12, wherein at least one fluorine atom of tetracycline-$BF_2$, glycylcycline-$BF_2$, emodin-$BF_2$, doxorubicin-$BF_2$, or daunorubicin-$BF_2$ is independently $^{19}F$.

* * * * *